US012780947B2

(12) United States Patent
Wang et al.

(10) Patent No.: US 12,780,947 B2
(45) Date of Patent: Nov. 3, 2026

(54) ANTIBODY BINDING TO CHI3L1 FOR TREATING CANCER

(71) Applicants: National Cheng Kung University, Tainan City (TW); AP Biosciences, Inc., Taipei City (TW)

(72) Inventors: Yi-Ching Wang, Tainan (TW); Chih-Peng Chang, Tainan (TW); Pei-Chia Su, Tainan (TW); I-Ying Kuo, Kaohsiung (TW); Jhong-Jhe You, Taipei City (TW); Jeng-Horng Her, San Jose, CA (US)

(73) Assignees: National Cheng Kung University, Tainan City (TW); AP Biosciences, Inc., Taipei City (TW)

( * ) Notice: Subject to any disclaimer, the term of this patent is extended or adjusted under 35 U.S.C. 154(b) by 419 days.

(21) Appl. No.: 18/698,648

(22) PCT Filed: Sep. 30, 2022

(86) PCT No.: PCT/US2022/077374
§ 371 (c)(1),
(2) Date: Apr. 4, 2024

(87) PCT Pub. No.: WO2023/076783
PCT Pub. Date: May 4, 2023

(65) Prior Publication Data

US 2024/0400717 A1 Dec. 5, 2024

Related U.S. Application Data

(60) Provisional application No. 63/272,701, filed on Oct. 28, 2021.

(51) Int. Cl.
*C07K 16/40* (2006.01)
*A61K 31/7068* (2006.01)
(Continued)

(52) U.S. Cl.
CPC .......... *C07K 16/40* (2013.01); *A61K 31/7068* (2013.01); *A61K 47/6871* (2017.08); *A61P 35/00* (2018.01); *A61K 2039/505* (2013.01)

(58) Field of Classification Search
None
See application file for complete search history.

(56) References Cited

U.S. PATENT DOCUMENTS

2014/0363440 A1 12/2014 Makler et al.
2015/0284471 A1 10/2015 Meininger et al.
(Continued)

OTHER PUBLICATIONS

Hamilton et al., How to target small cell lung cancer. Oncoscience 2015, vol. 2, No. 8, p. 684-692 (Year: 2015).*
(Continued)

*Primary Examiner* — Aurora M Fontainhas
(74) *Attorney, Agent, or Firm* — The Webb Law Firm

(57) ABSTRACT

An antibody or an antigen-binding portion thereof binding to CHI3L1 includes a heavy chain variable region and a light chain variable region. The antibody or the antigen-binding portion thereof targeting CHI3L1 not just inhibit activated AKT and ERK signals, cancer cells migration, tumor progression, tumor fibrosis, angiogenesis and cancer-induced muscle loss such as cachexia, but modulate TME toward an immunostimulatory phenotype.

19 Claims, 70 Drawing Sheets

Specification includes a Sequence Listing.

(51) Int. Cl.
*A61K 47/68* (2017.01)
*A61P 35/00* (2006.01)
*A61K 39/00* (2006.01)

(56) References Cited

U.S. PATENT DOCUMENTS

| | | | |
|---|---|---|---|
| 2016/0207996 A1 | 7/2016 | Ulrichts et al. | |
| 2019/0062457 A1 | 2/2019 | Elias et al. | |
| 2021/0002343 A1 | 1/2021 | Karow et al. | |
| 2021/0363440 A1 | 11/2021 | Yu et al. | |

OTHER PUBLICATIONS

Cohen et al., "Fibroblasts drive an immunosuppressive and growth-promoting microenvironment in breast cancer via secretion of Chitinase 3-like-1", Oncogene, 2017, pp. 4457-4468, vol. 36.
He et al., "Chitinase 3-like 1 Regulates Cellular and Tissue Responses via IL-13 Receptor α2", Cell Reports, 2013, pp. 830-841, vol. 4.
Higashiyama et al., "Chitinase 3-like 1 deficiency ameliorates liver fibrosis by promoting hepatic macrophage apoptosis", Hepatology Research, 2019, pp. 1316-1328, vol. 49.
Jodhi et al., "Colorectal Cancer Immunotherapy: Options and Strategies", Frontiers in Immunology, 2020, pp. 1-18, vol. 11, article 1624.
Kim et al., "Regulation of chitinase-3-like-1 in T cell elicits Th1 and cytotoxic responses to inhibit lung metastasis", Nature Communications, 2018, pp. 1-14, vol. 9, Issue 503.
Kim et al., "Chitinase 3-Like 1 Contributes to Food Allergy via M2 Macrophage Polarization", Allergy Asthma Immunology Research, 2020, pp. 1012-1028, vol. 12, Issue 6.
Kzhyshkowska et al., "Role of chitinase-like proteins in cancer", Biological Chemistry, 2016, pp. 231-247, vol. 397, Issue 3.
Létuvé et al., "YKL-40 is Elevated in Patients with Chronic Obstructive Pulmonary Disease and Activates Alveolar Macrophages", The Journal of Immunology, 2008, pp. 5167-5173, vol. 181, Issue 7.
Li et al., "Mitochondrial DNA stress triggers autophagy-dependent ferroptotic death", Autophagy, 2021, pp. 948-960, vol. 17, Issue 4.
Park et al., "The Chitinase-like Protein YKL-40 Is Secreted by Airway Epithelial Cells at Base Line and in Response to Compressive Mechanical Stress", The Journal of Biological Chemistry, 2010, pp. 29817-29825, vol. 285, Issue 39.
Siegel et al., "Cancer Statistics, 2021", CA Cancer J Clin., 2021, pp. 7-33, vol. 71, Issue 1.
Través et al., "Relevance of the MEK/ERK Signaling Pathway in the Metabolism of Activated Macrophages: A Metabolomic Approach", The Journal of Immunology, 2012, pp. 1402-1410, vol. 188, Issue 3.
Vergadi et al., "Akt Signaling Pathway in Macrophage Activation and M1/M2 Polarization", The Journal of Immunology, 2017, pp. 1006-1014, vol. 198, Issue 3.
Wang et al., "CHI3L1 in the pathophysiology and diagnosis of liver diseases", Biomedicine & Pharmacotherapy, 2020, pp. 1-6, vol. 131, Article 110680.
Xing et al., "Chitinase 3-like 1 secreted by peritumoral macrophages in esophageal squamous cell carcinoma is a favorable prognostic factor for survival", World Journal of Gastroenterology, 2017, pp. 7693-7704. vol. 23, Issue 43.
Yeo et al., "Roles of chitinase 3-like 1 in the development of cancer, neurodegenerative diseases, and inflammatory diseases", Pharmacology & Therapeutics, 2019, pp. 1-20, vol. 203, Issue 107394.
Zhao et al., "Chitinase-3 like-protein-1 function and its role in diseases", Signal Transduction and Targeted Therapy, 2020, pp. 1-20, vol. 5, Issue 201.

* cited by examiner

ANTIBODY BINDING TO CHI3L1 FOR TREATING CANCER

CROSS-REFERENCE TO RELATED APPLICATIONS

This application is the United States national phase of International Application No. PCT/US2022/077374, filed Sep. 30, 2022, and claims priority to U.S. Provisional Patent Application No. 63/272,701, filed Oct. 28, 2021, the disclosures of which are hereby incorporated by reference in their entireties.

The Sequence Listing associated with this application is filed in electronic format via EFS-Web and is hereby incorporated by reference into the specification in its entirety. The name of the XML file containing the Sequence Listing is NP-30914-US_SEQ_LIST.xml. The size of the XML file is 80,213 bytes, and the XML file was created on Feb. 17, 2024.

BACKGROUND OF THE INVENTION

Field of Invention

The present invention relates to an antibody. More particularly, the present invention relates to the antibody for cancer therapy.

Description of Related Art

Lung cancer is the first and colorectal cancer the third most common cause of cancer death worldwide (Johdi and Sukor 2020; Siegel et al. 2021). Despite the incidence of pancreatic cancer is not as high as lung cancer, it is one of the most aggressive cancers with very low five-year relative survival rate (Li et al. 2021; Siegel et al. 2021). Notably, largely increased non-enzymatic chitinase-3 like-protein-1 (CHI3L1) in serum and intratumoral expression correlates with tumor metastasis and poor outcome of lung, colorectal and pancreatic cancer patients (Yeo et al. 2019; Zhao et al. 2020), making it an appealing target for cancer therapy. In addition, level of CHI3L1 in serum or plasma has been proposed as a non-invasive prognostic biomarker (Kzhyshkowska et al. 2016; Wang et al. 2020).

CHI3L1 is a carbohydrate-binding lectin with no chitinase activity. CHI3L1 modulates inflammatory balance between Th1 and Th2 cells, cytokines induced inflammation, inflammatory cells apoptosis, alternative activated macrophage (M2) differentiation, AKT and extracellular signal-regulated kinase (ERK) signaling (Higashiyama et al. 2019; Kim et al. 2018); (Kim et al. 2020; Letuve et al. 2008). Within all pathways, AKT and ERK are the most widely studied signaling cascades involved in CHI3L1-induced inflammatory response (He et al. 2013). For example, activation of AKT and ERK pathways is essential for restraining pro-inflammation and M2 polarization (Traves et al. 2012; Vergadi et al. 2017).

The creation of immunosuppressive tumor microenvironment (TME) is involved in the CHI3L1-induced cancer cell promotion. CHI3L1 can be secreted by various cells, including macrophages, T cells, fibroblasts, epithelial cells and tumor cells (Cohen et al. 2017; Park et al. 2010; Xing et al. 2017).

Therefore, how to treating CHI3L1-induced cancer, the related art really needs to be improved.

SUMMARY OF THE INVENTION

The present disclosure provides an antibody or an antigen-binding portion thereof binding to CHI3L1, comprising:

a heavy chain variable (VH) region comprising a heavy chain complementarity determining region (CDR-H1), a CDR H2, and a CDR H3 and a light chain variable (VL) region comprising a light chain complementarity determining region 1 (CDR L1), a CDR L2, and a CDR L3, wherein the CDR-H1 comprises SEQ ID NO: 3, the CDR-H2 comprises SEQ ID NO: 4, and the CDR-H3 comprises SEQ ID NO: 5; and the CDR-L1 comprises SEQ ID NO: 6, the CDR-L2 comprises SEQ ID NO: 7, and the CDR-L3 comprises SEQ ID NO: 8, or wherein the CDR-H1 comprises SEQ ID NO: 11, the CDR-H2 comprises SEQ ID NO: 12, and the CDR-H3 comprises SEQ ID NO: 13; and the CDR-L1 comprises SEQ ID NO: 14, the CDR-L2 comprises SEQ ID NO: 15, and the CDR-L3 comprises SEQ ID NO: 16, or wherein the CDR-H1 comprises SEQ ID NO: 19, the CDR-H2 comprises SEQ ID NO: 20, and the CDR-H3 comprises SEQ ID NO: 21; and the CDR-L1 comprises SEQ ID NO: 22, the CDR-L2 comprises SEQ ID NO: 23, and the CDR-L3 comprises SEQ ID NO: 24, or wherein the CDR-H1 comprises SEQ ID NO: 27, the CDR-H2 comprises SEQ ID NO: 28, and the CDR-H3 comprises SEQ ID NO: 29; and the CDR-L1 comprises SEQ ID NO: 30, the CDR-L2 comprises SEQ ID NO: 31, and the CDR-L3 comprises SEQ ID NO: 32, or wherein the CDR-H1 comprises SEQ ID NO: 35, the CDR-H2 comprises SEQ ID NO: 36, and the CDR-H3 comprises SEQ ID NO: 37; and the CDR-L1 comprises SEQ ID NO: 38, the CDR-L2 comprises SEQ ID NO: 39, and the CDR-L3 comprises SEQ ID NO: 40, or wherein the CDR-H1 comprises SEQ ID NO: 43, the CDR-H2 comprises SEQ ID NO: 44, and the CDR-H3 comprises SEQ ID NO: 45; and the CDR-L1 comprises SEQ ID NO: 46, the CDR-L2 comprises SEQ ID NO: 47, and the CDR-L3 comprises SEQ ID NO: 48, or wherein the CDR-H1 comprises SEQ ID NO: 51, the CDR-H2 comprises SEQ ID NO: 52, and the CDR-H3 comprises SEQ ID NO: 53; and the CDR-L1 comprises SEQ ID NO: 54, the CDR-L2 comprises SEQ ID NO: 55, and the CDR-L3 comprises SEQ ID NO: 56, or wherein the CDR-H1 comprises SEQ ID NO: 59, the CDR-H2 comprises SEQ ID NO: 60, and the CDR-H3 comprises SEQ ID NO: 61; and the CDR-L1 comprises SEQ ID NO: 62, the CDR-L2 comprises SEQ ID NO: 63, and the CDR-L3 comprises SEQ ID NO: 64, or wherein the CDR-H1 comprises SEQ ID NO: 67, the CDR-H2 comprises SEQ ID NO: 68, and the CDR-H3 comprises SEQ ID NO: 69; and the CDR-L1 comprises SEQ ID NO: 70, the CDR-L2 comprises SEQ ID NO: 71, and the CDR-L3 comprises SEQ ID NO: 72, or wherein the CDR-H1 comprises SEQ ID NO: 75, the CDR-H2 comprises SEQ ID NO: 76, and the CDR-H3 comprises SEQ ID NO: 77; and the CDR-L1 comprises SEQ ID NO: 78, the CDR-L2 comprises SEQ ID NO: 79, and the CDR-L3 comprises SEQ ID NO: 80, or wherein the CDR-H1 comprises SEQ ID NO: 83, the CDR-H2 comprises SEQ ID NO: 84, and the CDR-H3 comprises SEQ ID NO: 85; and the CDR-L1 comprises SEQ ID NO: 86, the CDR-L2 comprises SEQ ID NO: 87, and the CDR-L3 comprises SEQ ID NO: 88.

In some embodiments, the antibody or the antigen-binding portion thereof binding to CHI3L1 further comprises the VH region comprising SEQ ID NO: 1 or a sequence having at least 90% amino acid sequence identity to SEQ ID NO: 1; and the VL region comprising SEQ ID NO: 2, or a sequence having at least 90% amino acid sequence identity to SEQ ID NO: 2; the VH region comprising SEQ ID NO: 9, or a sequence having at least 90% amino acid sequence identity to SEQ ID NO: 9; and the VL region comprising SEQ ID NO: 10, or a sequence having at least 90% amino acid sequence identity to SEQ ID NO: 10; the VH region comprising SEQ ID NO: 17, or a sequence having at least 90% amino acid sequence identity to SEQ ID NO: 17; and the VL region comprising SEQ ID NO: 18, or a sequence having at least 90% amino acid sequence identity to SEQ ID NO: 18; the VH region comprising SEQ ID NO: 25, or a sequence having at least 90% amino acid sequence identity to SEQ ID NO: 25; and the VL region comprising SEQ ID NO: 26, or a sequence having at least 90% amino acid sequence identity to SEQ ID NO: 26; the VH region comprising SEQ ID NO: 33, or a sequence having at least 90% amino acid sequence identity to SEQ ID NO: 33; and the VL region comprising SEQ ID NO: 34, or a sequence having at least 90% amino acid sequence identity to SEQ ID NO: 34; the VH region comprising SEQ ID NO: 41, or a sequence having at least 90% amino acid sequence identity to SEQ ID NO: 41; and the VL region comprising SEQ ID NO: 42, or a sequence having at least 90% amino acid sequence identity to SEQ ID NO: 42; the VH region comprising SEQ ID NO: 49, or a sequence having at least 90% amino acid sequence identity to SEQ ID NO: 49; and the VL region comprising SEQ ID NO: 50, or a sequence having at least 90% amino acid sequence identity to SEQ ID NO: 50; the VH region comprising SEQ ID NO: 57, or a sequence having at least 90% amino acid sequence identity to SEQ ID NO: 57; and the VL region comprising SEQ ID NO: 58, or a sequence having at least 90% amino acid sequence identity to SEQ ID NO: 58; the VH region comprising SEQ ID NO: 65, or a sequence having at least 90% amino acid sequence identity to SEQ ID NO: 65; and the VL region comprising SEQ ID NO: 66, or a sequence having at least 90% amino acid sequence identity to SEQ ID NO: 66; the VH region comprising SEQ ID NO: 73, or a sequence having at least 90% amino acid sequence identity to SEQ ID NO: 73; and the VL region comprising SEQ ID NO: 74, or a sequence having at least 90% amino acid sequence identity to SEQ ID NO: 74; or the VH region comprising SEQ ID NO: 81, or a sequence having at least 90% amino acid sequence identity to SEQ ID NO: 81; and the VL region comprising SEQ ID NO: 82, or a sequence having at least 90% amino acid sequence identity to SEQ ID NO: 82.

In some embodiments, the antibody is a human antibody.

In some embodiments, the antibody or the antigen-binding portion thereof is a single chain Fv (scFv), fragment-antigen binding (Fab), (Fab') 2, or (scFv') 2.

In some embodiments, the antibody is an IgG, IgE, IgM, IgD, IgA, or IgY antibody.

In some embodiments, the IgG antibody is an IgG1, IgG2, IgG3, or IgG4 antibody.

The present disclosure also provides a pharmaceutical composition, comprising the antibody or the antigen-binding portion thereof as above mentioned, and at least one pharmaceutically acceptable carrier.

In some embodiments, the pharmaceutical composition further comprises a therapeutic agent.

In some embodiments, the therapeutic agent comprises gemcitabine.

The present disclosure also provides an antibody-drug conjugate comprising a therapeutic agent; and an antibody or an antigen-binding portion thereof as above mentioned, wherein the therapeutic agent is covalently conjugated to the antibody or the antigen-binding portion thereof by a linker.

The present disclosure also provides a nucleic acid molecule encoding the antibody or the antigen-binding portion thereof as above mentioned.

The present disclosure also provides a method of treating cancer comprising administering to a patient in need thereof an effective amount of the antibody or the antigen-binding portion thereof as above mentioned.

In some embodiments, the cancer is a CHI3L1 expressing tumor.

In some embodiments, the cancer is pancreas cancer, colon cancer, lung cancer, prostate cancer, non-small cell lung cancer (NSCLC), melanoma, lymphoma, breast cancer, esophageal cancer, head and neck cancer, renal cell carcinoma (RCC), ovarian cancer, kidney cancer, urinary bladder cancer, uterine cancer, cervical cancer, ovarian cancer, liver cancer, stomach cancer, rectal cancer, oral cavity cancer, pharynx cancer, thyroid cancer, skin cancer, brain cancer, bone cancer, hematopoietic cancer, or leukemia.

In some embodiments, the antibody or the antigen-binding portion thereof is used in combination with a therapeutic agent.

In some embodiments, the therapeutic agent comprises gemcitabine.

In some embodiments, the antibody or the antigen-binding portion thereof inhibits activated AKT signal, inhibits activated ERK signal, inhibits cancer cells migration, inhibits tumor progression, inhibits tumor fibrosis, inhibits angiogenesis, inhibits cachexia, modulates TME toward an immunostimulatory phenotype, or a combination thereof.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion. The disclosure can be more fully understood by reading the following detailed description of the embodiment, with reference made to the accompanying drawings as follows.

DESCRIPTION OF THE INVENTION

Figure 1A:
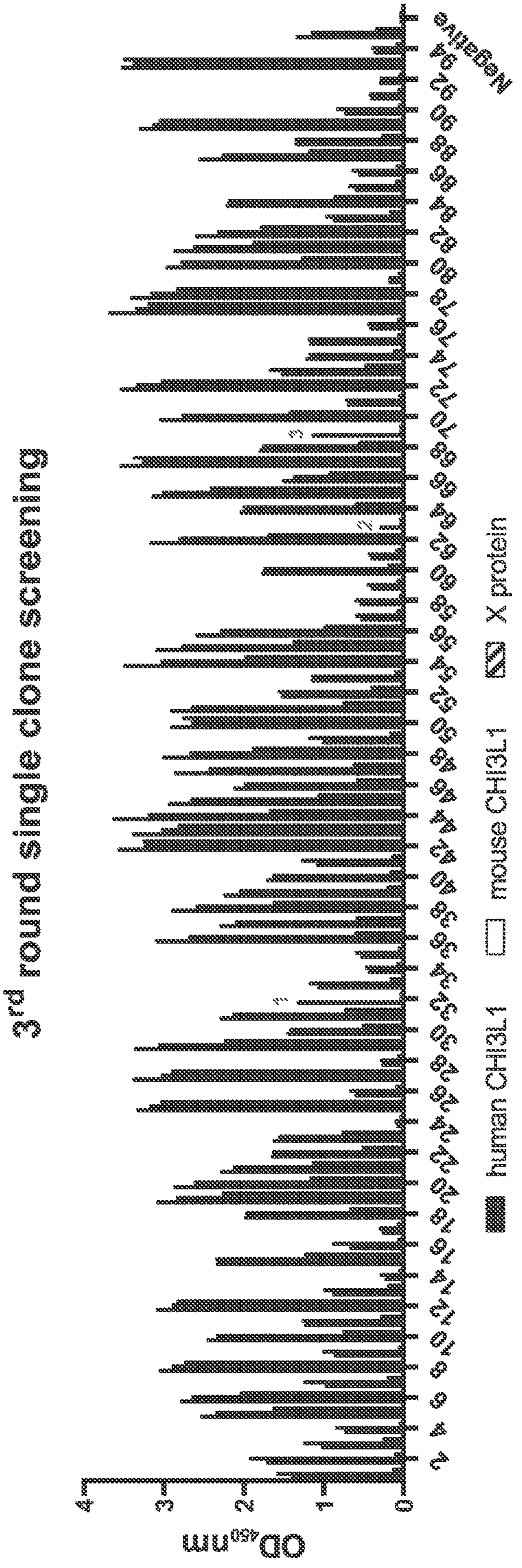
FIGS. 1A to 1D show selection of CHI3L1 specific phage clones from OmniMab.
Figure 1B:
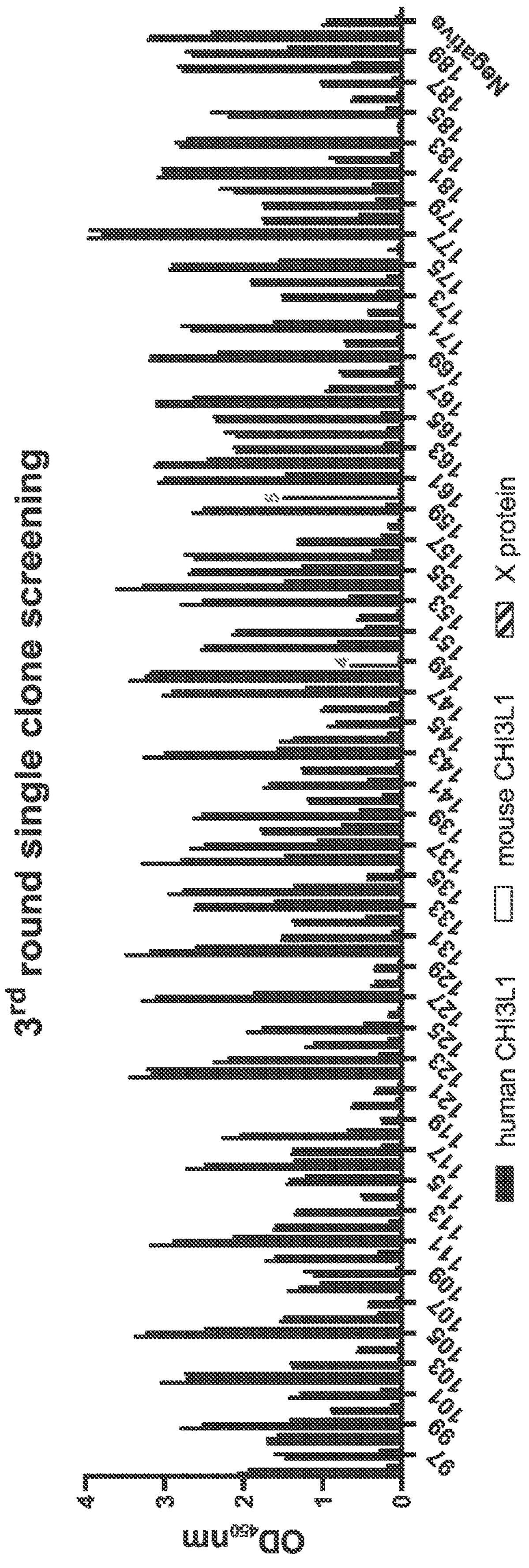

The following disclosure provides detailed description of many different embodiments, or examples, for implementing different features of the provided subject matter. These are, of course, merely examples and are not intended to limit the invention but to illustrate it. In addition, various embodiments disclosed below may combine or substitute one embodiment with another, and may have additional embodiments in addition to those described below in a beneficial way without further description or explanation. In the following description, many specific details are set forth to provide a more thorough understanding of the present disclosure. It will be apparent, however, to those skilled in the art, that the present disclosure may be practiced without these specific details.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification, specify the presence of stated features, regions, integers, steps, operations, elements, and/or components, but do not preclude the presence or addition of one or more other features, regions, integers, steps, operations, elements, components, and/or groups thereof.

In some embodiments, antibodies provided herein have a VH region and VL region respectively including an amino acid sequence having at least about 80% identity, for example, 85%, 90%, 91%, 92%, 93%, 94%, 95%, 96%, 97%, 98%, 99%, and any number or range in between, to the amino acid sequence of SEQ ID NO: 1 and SEQ ID NO: 2, SEQ ID NO:9 and SEQ ID NO:10, SEQ ID NO:17 and SEQ ID NO:18, SEQ ID NO: 25 and SEQ ID NO:26, SEQ ID NO:33 and SEQ ID NO:34, SEQ ID NO:41 and SEQ ID NO: 42, SEQ ID NO:49 and SEQ ID NO:50, SEQ ID NO:57 and SEQ ID NO:58, SEQ ID NO: 65 and SEQ ID NO:66, SEQ ID NO:73 and SEQ ID NO:74, or SEQ ID NO:81 and SEQ ID NO:82. In other embodiments, antibodies provided herein have a VH region and VL region respectively including an amino acid sequence having at least about 80% identity, wherein the amino acid sequence having at least about 80% identity excludes CDRs.

In some embodiments, the antibody or the antigen-binding portion thereof provided herein includes immunoglobulin framework region (FR) sequences. These sequences are preferably not immunogenic in humans, and are therefore preferably human or humanized FR sequences. Suitable human or humanized FR sequences are known in the art. Specifically preferred FR sequences can be taken from the embodiments shown herein, disclosing the complete antigen binding units and thereby CDR sequences as well as FR sequences.

In some embodiments, antibodies or antigen binding fragments thereof provided herein further include an Fc domain. The term Fc domain refers to an antibody region that includes at least a hinge region, a CH2 domain, and a CH3 domain. In some examples, the Fc domain is an IgG domain, an IgE domain, an IgM domain, and IgD domain, an IgA domain, or an IgY domain. Fc domains of any sequence and from any species can be used, including human, ape, monkey, mouse, rabbit, goat, and others. In some examples, Fc domains are engineered, i.e. non-naturally occurring or recombinant Fc domains generated using techniques of molecular biology, for example. In some examples, the IgG domain is an IgG1 domain, an IgG2 domain, an IgG3 domain, or an IgG4 domain.

In some embodiments, pharmaceutical composition provided herein includes any one of the antibodies or antigen binding fragments thereof provided herein and a pharmaceutically acceptable carrier. In some examples, the pharmaceutically acceptable carrier is conjugated to the C-terminus of one or more polypeptides of the antibody or antigen binding fragment. Any suitable means of conjugating the pharmaceutically acceptable carrier can be used, for example, including covalent conjugation and use of linkers.

In some embodiments, antibody-drug conjugates provided herein can include antibodies or antigen binding fragments thereof provided herein. For example, antibodies or antigen binding fragments thereof that specifically binds to CHI3L1 can be included in antibody-drug conjugates. In some examples, antibody-drug conjugates provided herein include a therapeutic agent, for example, the therapeutic agent includes, but is not limited to chemotherapeutic agent, a therapeutically active compound that inhibits angiogenesis, a signal transduction pathway inhibitor, an immune modulator, an immune checkpoint inhibitor, or a hormonal therapy agent. In some examples, the chemotherapeutic agent includes, but is not limited to gemcitabine, or abraxane.

In some embodiments, antibody-drug conjugates provided herein are used for the treatment of cancer. For example, an antibody of an antibody-drug conjugate targets to an epitope of an antigen on tumor cells, thereby targeting a therapeutic agent included in the antibody-drug conjugate to tumor cells. The therapeutic agent is internalized and released in tumor cells when the antibody-drug conjugate is targeting the tumor cell.

Our previous unpublished data showed that CHI3L1-induced tumor growth and cell proliferation signaling are inhibited by CHI3L1 polyclonal neutralized antibodies in pancreatic, colorectal and lung cancer models. For further clinical application, we developed and characterized phage display-derived fully human monoclonal antibodies (mAb). Here we show that the mAbs targeting CHI3L1 not just inhibit activated AKT and ERK signals, cancer cells migration, tumor progression, tumor fibrosis, angiogenesis and cancer-induced muscle loss (cachexia), but modulate TME toward an immunostimulatory phenotype in vitro and in vivo.

EXAMPLE

Development of fully human monoclonal antibodies against chitinase-3 like-protein-1 (CHI3L1) with Phage display technology.

To generate antibodies against CHI3L1, selections with an OmniMab phagemid library were carried out. The phagemid library was built up by AP Biosciences Inc. (APBio Inc.) from a collection of peripheral blood mononuclear cells from over a hundred healthy donors.

First round panning was performed using Hyperphage (M13K07ΔρIII, Progen, Heidelberg, Germany). Solution phase panning was used for CHI3L1-specific binder selection and isolation from the OmniMab library. Solution phase panning was performed using recombinant human CHI3L1 which produced by mammalian cell expression system used in first-round selection. Next three rounds enrichment were also used solution phase panning. The specific CHI3L1 binders were screening and isolated by direct ELISA after three and four round panning. Positive binders were isolated and sent for sequencing to confirm the sequence and diversity of the heavy chain. The phage clones recognize human CHI3L1 specifically after three rounds (FIG. 1A and FIG. 1B) four rounds (FIG. 1C and FIG. 1D) human CHI3L1 specific enrichment process from OmniMab phage library. Pre-coated human CHI3L1 recombinant protein, incubation with supernatant containing rescued phages for 1 hour and washed with phosphate buffered saline (PBS) containing 0.1% Tween-20 for three times. Bound phages were detected by horseradish peroxidase (HRP) conjugated anti-M13 antibody (Roche®) and 3,3',5,5'-tetramethylbenzidine (TMB) substrate was used for signal development. The $OD_{450}$ readings were recorded. As shown in FIG. 1A, FIG. 1B, FIG. 1C and FIG. 1D, clones isolated from round three panning, only five clones had specificity with CHI3L1 antigen. Several clones were isolated from fourth round panning that specifically recognized human CHI3L1 antigen, and some clones can recognize both human and mouse CHI3L1 antigen compared with negative control.

These results show that phage clones obtained after three or four rounds of CHI3L1-specific enrichment specifically recognize CH13L1. Positive CHI3L1 binders were renamed according to which round of panning, exclude no binding activity or non-specific binding clones (Table 1).

TABLE 1 comparison table of numbers labeled on FIGS. 1A-D.

| NO. | Clone name |
|---|---|
| 1 | #hu 293R3-1 |
| 2 | #hu 293R3-2 |
| 3 | #hu 293R3-3 |
| 4 | #hu 293R3-4 |
| 5 | #hu 293R3-5 |
| 6 | #hu R4-1 |
| 7 | #hu R4-2 |
| 8 | #hu R4-3 |
| 9 | #hu R4-4 |
| 10 | #hu R4-6 |
| 11 | #hu R4-7 |
| 12 | #hu R4-8 |
| 13 | #hu R4-12 |
| 14 | #hu R4-13 |

TABLE 1-continued comparison table of numbers labeled on FIGS. 1A-D.

| NO. | Clone name |
|---|---|
| 15 | #hu R4-15 |
| 16 | #hu R4-16 |
| 17 | #hu R4-18 |
| 18 | #hu R4-21 |
| 19 | #hu R4-22 |
| 20 | #hu R4-26 |
| 21 | #hu R4-28 |
| 22 | #hu R4-31 |
| 23 | #hu R4-33 |
| 24 | #hu R4-35 |
| 25 | #hu R4-36 |
| 26 | #hu R4-39 |
| 27 | #hu R4-43 |
| 28 | #hu R4-44 |
| 29 | #hu R4-45 |
| 30 | #hu R4-47 |
| 31 | #hu R4-51 |
| 32 | #hu R4-52 |
| 33 | #hu R4-53 |
| 34 | #hu R4-54 |
| 35 | #hu R4-55 |
| 36 | #hu R4-59 |
| 37 | #hu R4-62 |
| 38 | #hu R4-63 |
| 39 | #hu R4-66 |
| 40 | #hu R4-67 |
| 41 | #hu R4-68 |
| 42 | #hu R4-71 |
| 43 | #hu R4-75 |
| 44 | #hu R4-76 |
| 45 | #hu R4-77 |
| 46 | #hu R4-81 |
| 47 | #hu R4-85 |
| 48 | #hu R4-90 |
| 49 | #hu R4-93 |
| 50 | #hu R4-97 |
| 51 | #hu R4-104 |
| 52 | #hu R4-106 |
| 53 | #hu R4-108 |

To quickly screen candidates, the heavy chains and light chains of positive CHI3L1 binders identified by ELISA were amplified, digested and subcloned into an IgG expression vector generated by APBio and carrying the IgG1 constant region. After sequence validation, plasmids were prepared and produced antibody by using mammalian cell expression system. After 6 days of culture, antibody secreted into serum-free medium was affinity purified from culture supernatant by Protein A chromatography. Purified antibody was concentrated, followed by dialysis in PBS buffer. The final concentration of dialyzed protein was determined using a NanoDrop2000 spectrophotometer and the purity and integrity were determined by SDS-PAGE with or without reducing reagent.

Figure 2A:
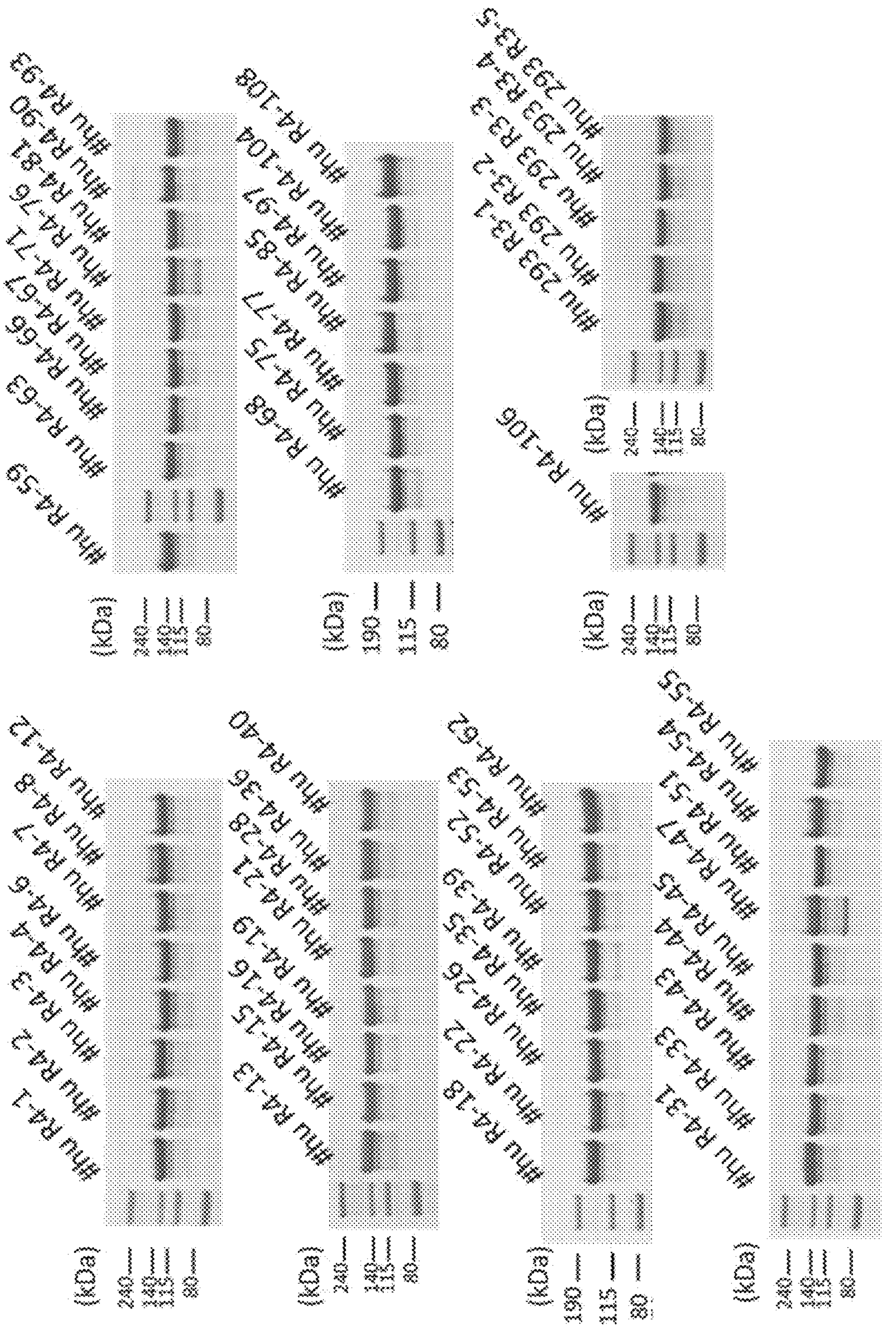
FIGS. 2A and 2B show expression and purification of CHI3L1 specific antibody leads from mammalian expression system.
Figure 2B:
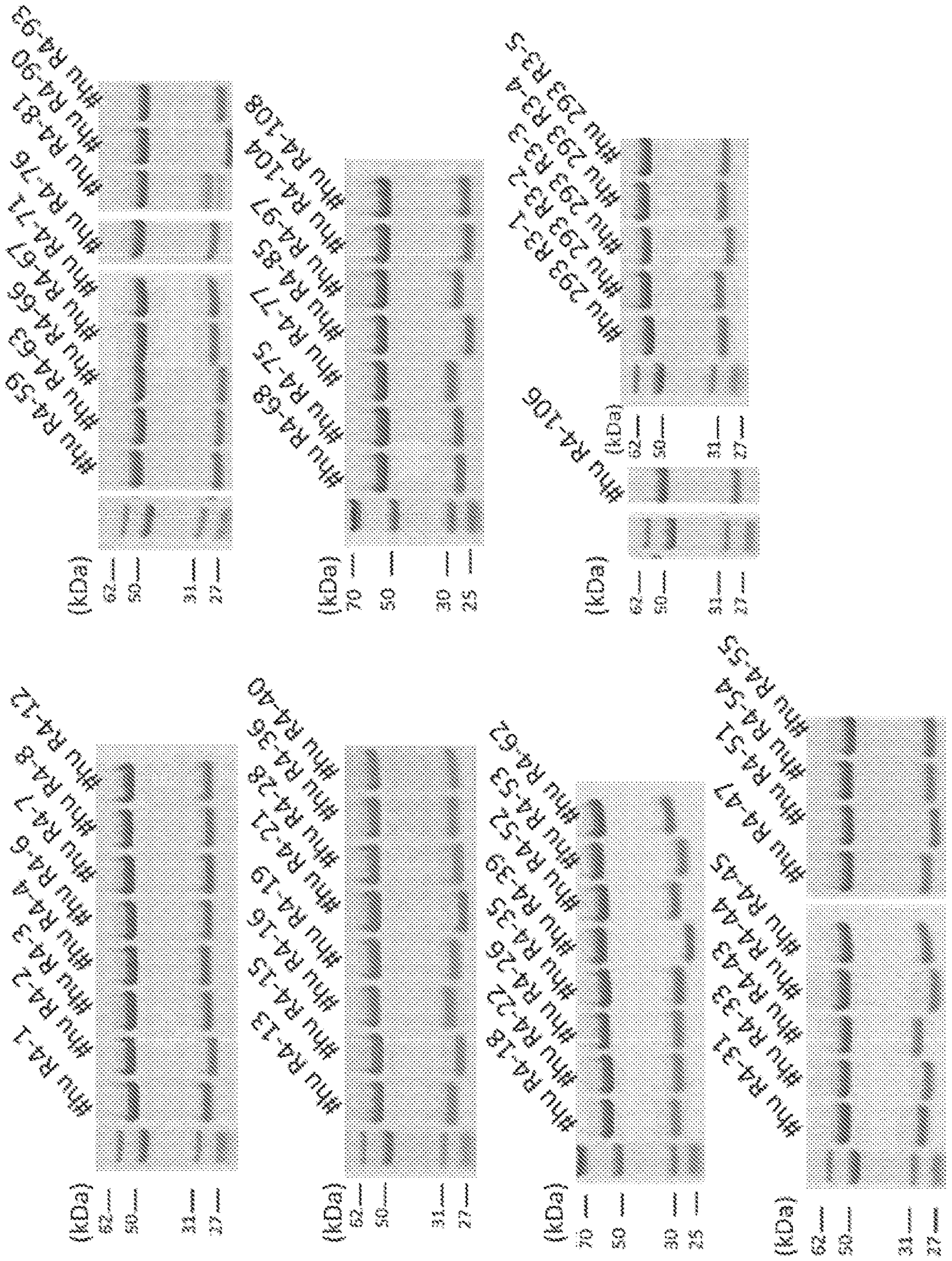

FIG. 2A and FIG. 2B show PAGE gel analysis of purified anti-CHI3L1 antibody leads. The purified proteins were analyzed under reducing and non-reducing condition before loading on the gel (5 μg/lane). Result indicated that proteins have a molecular weight of about 145 kDa under non-reducing conditions, and heavy chain and light chain have a molecular weight of about 55 kDa and about 25 kDa respectively under reducing conditions.

Figure 1C:
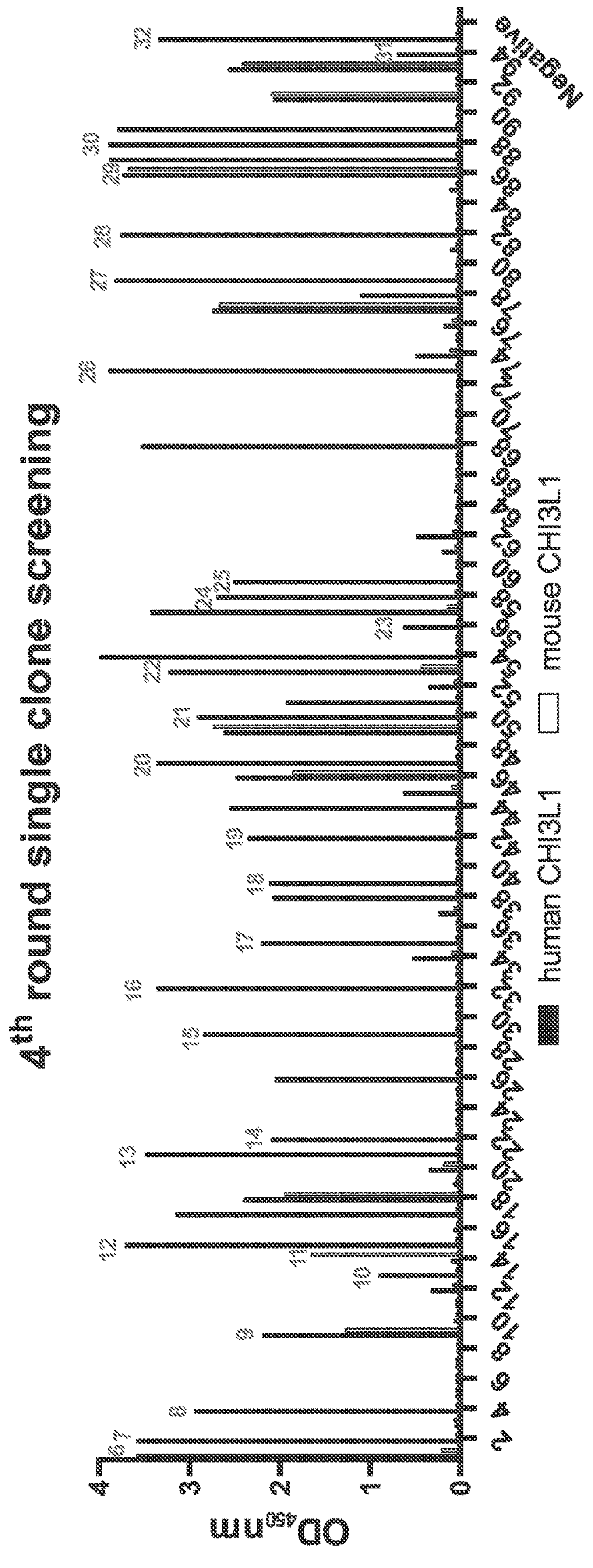
Figure 1D:
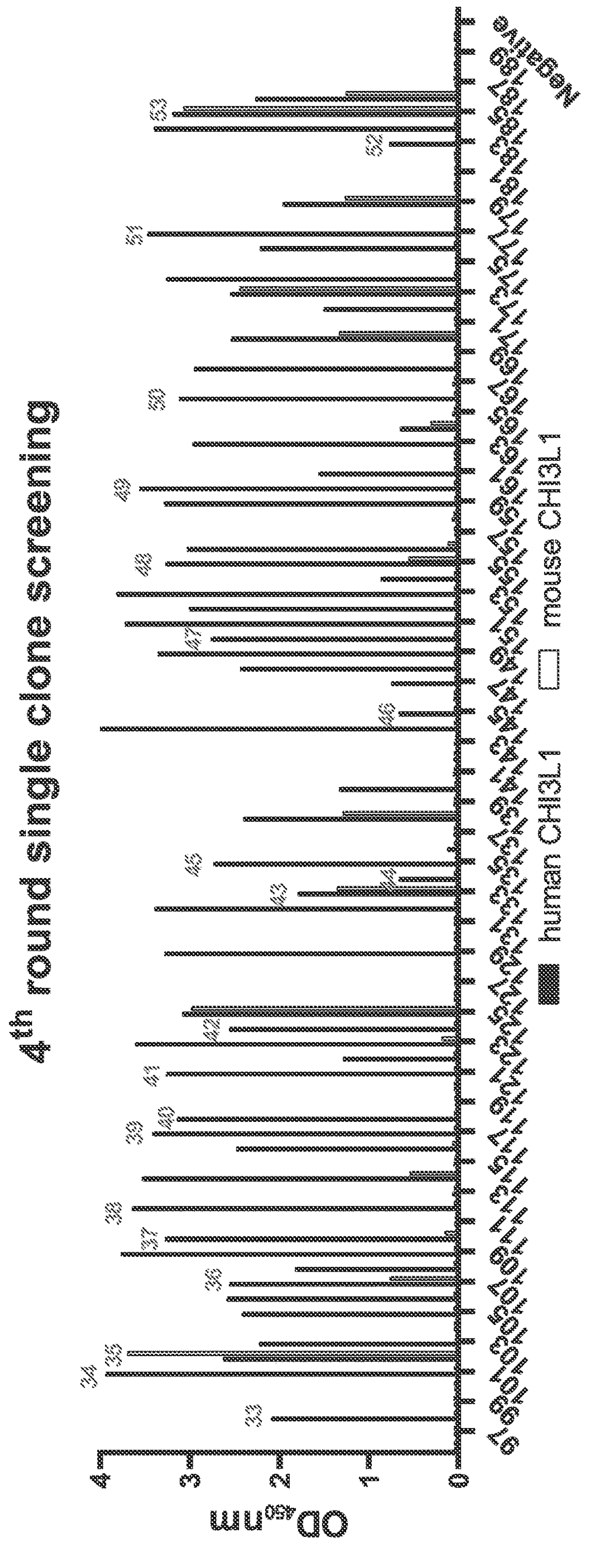
Figure 3A:
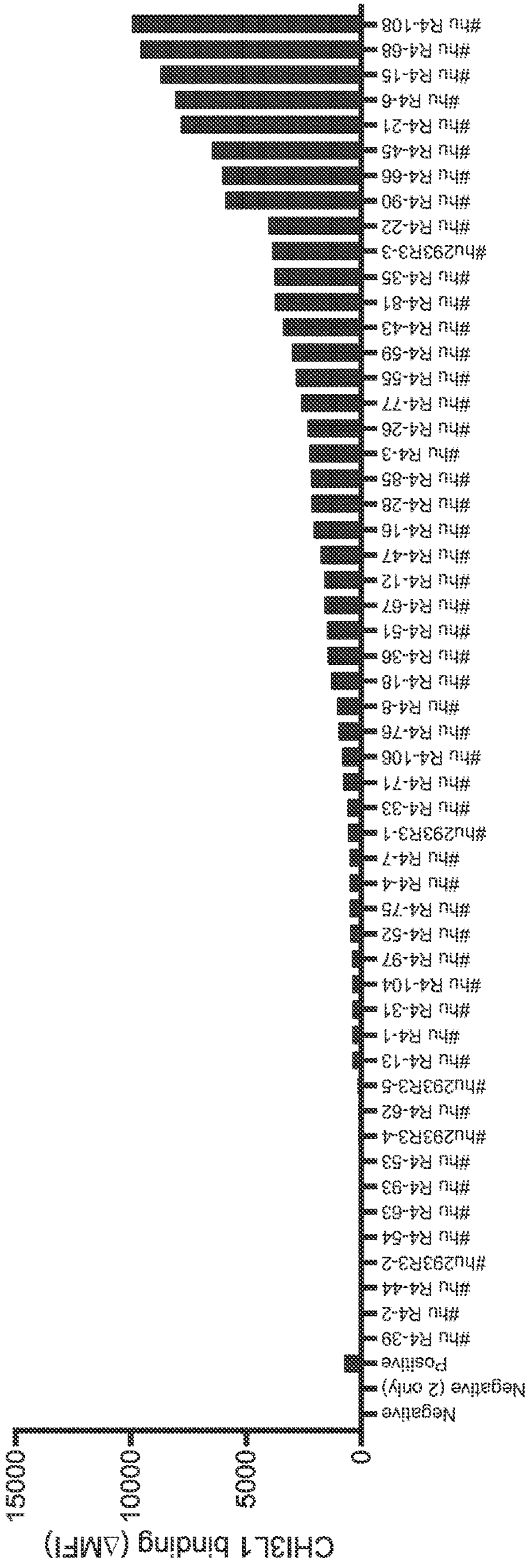
FIGS. 3A and 3B show inhibition of CHI3L1 association with A549 cells by antibody leads.
Figure 3B:
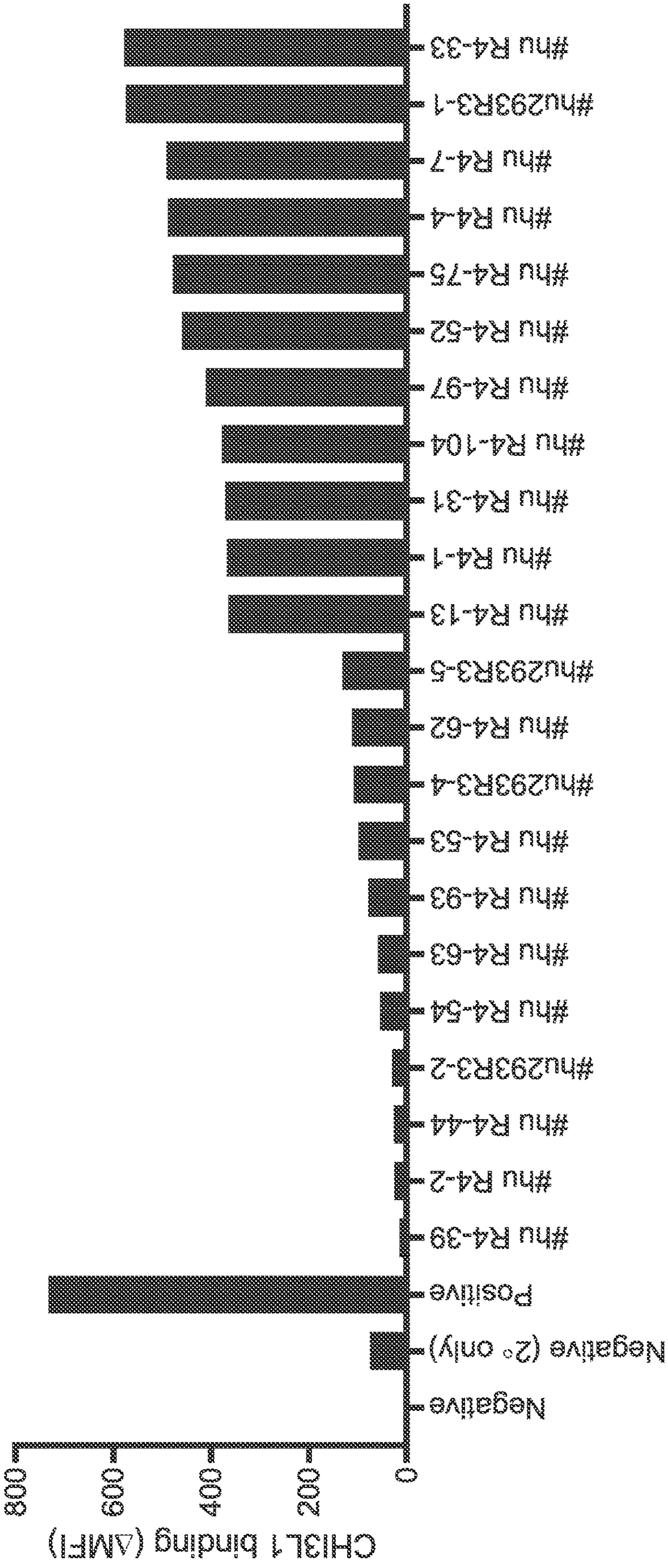

CHI3L1 is known to associate with different receptors, such as IL-13Rα2 (He et al. 2013), CRTH2 (Zhou et al. 2015), TMEM219 (Lee et al. 2016), and galectin-3 (Zhou et al. 2015). Recent studies show that CHI3L1 binds to and signals via interleukin-13 receptor alpha 2 (IL-13Rα2) which is significantly upregulated in a number of human cancers (Barderas et al. 2012; Bartolome et al. 2015; Zhao et al. 2015), such as A549 cells, to promote the tumor progression. Therefore, purified antibody leads were functionally screened for their ability to block CHI3L1 binding to IL-13Rα2 on A549 cell line (FIG. 3A). As shown in FIG. 3B, 22 antibody clones showed a significant CHI3L1 neutralizing activity if compared with positive control, CHI3L1 only. Here the leads with best neutralizing activity, such as #293R3-2, #293R3-4, #293R3-5, #R4-2, #R4-39, #R4-53, #R4-54, #R4-62, #R4-63, and #R4-93 were conducted to another functionality validation as shown in the FIGS. 4A to 4G. Meanwhile, the #hu R4-4 which is showed to cross-react with mouse CHI3L1 in FIG. 1C is applied for validation as well. The sequences and defied CDR regions among those monoclonal antibodies are listed and summarized in the sequences list (SEQ ID NOs: 1 to 88) and Table 2, respectively. Anti-CHI3L1 clone R4-2 heavy chain (SEQ ID NO: 1), anti-CHI3L1 clone R4-2 light chain (SEQ ID NO: 2), anti-CHI3L1 clone R4-4 heavy chain (SEQ ID NO: 9), anti-CHI3L1 clone R4-4 light chain (SEQ ID NO: 10), anti-CHI3L1 clone R4-39 heavy chain (SEQ ID NO: 17), anti-CHI3L1 clone R4-39 light chain (SEQ ID NO: 18), anti-CHI3L1 clone R4-53 heavy chain (SEQ ID NO: 25), anti-CHI3L1 clone R4-53 light chain (SEQ ID NO: 26), anti-CHI3L1 clone R4-54 heavy chain (SEQ ID NO: 33), anti-CHI3L1 clone R4-54 light chain (SEQ ID NO: 34), anti-CHI3L1 clone R4-62 heavy chain (SEQ ID NO: 41), anti-CHI3L1 clone R4-62 light chain (SEQ ID NO: 42), anti-CHI3L1 clone R4-63 heavy chain (SEQ ID NO: 49), anti-CHI3L1 clone R4-63 light chain (SEQ ID NO: 50), anti-CHI3L1 clone R4-93 heavy chain (SEQ ID NO: 57), anti-CHI3L1 clone R4-93 light chain (SEQ ID NO: 58), anti-CHI3L1 clone 293R3-2 heavy chain (SEQ ID NO: 65), anti-CHI3L1 clone 293R3-2 light chain (SEQ ID NO: 66), anti-CHI3L1 clone 293R3-4 heavy chain (SEQ ID NO: 73), anti-CHI3L1 clone 293R3-4 light chain (SEQ ID NO: 74), anti-CHI3L1 clone 293R3-5 heavy chain (SEQ ID NO: 81), and anti-CHI3L1 clone 293R3-5 light chain (SEQ ID NO: 82) are shown in sequence listing.

TABLE 2

| | | Sequence | | |
|---|---|---|---|---|
| No. | Name | CDR1 | CDR2 | CDR3 |
| 7 | R4-2-H | SSYAIS<br>SEQ ID NO: 3 | GIIPIFGTANYAQKFQG<br>SEQ ID NO: 4 | GDIEYYDILTGYYYYFDY<br>SEQ ID NO: 5 |
| | R4-2-L | GGNDIGSKSVQ<br>SEQ ID NO: 6 | DNDRPS<br>SEQ ID NO: 7 | QVWDSTSDHYV<br>SEQ ID NO: 8 |
| 9 | R4-4-H | NYAMT<br>SEQ ID NO: 11 | TISGNGDETFYADSVKG<br>SEQ ID NO: 12 | GGHYSFFDS<br>SEQ ID NO: 13 |
| | R4-4-L | TRSSGSIASNYVQ<br>SEQ ID NO: 14 | EDNQRPS<br>SEQ ID NO: 15 | QSYDSSNYV<br>SEQ ID NO: 16 |
| 26 | R4-39-H | NYWIG<br>SEQ ID NO: 19 | IIYPDDSNTKYSPSFQG<br>SEQ ID NO: 20 | LDTYYYDSSGFPFDAFDI<br>SEQ ID NO: 21 |
| | R4-39-L | QASQDISTFLS<br>SEQ ID NO: 22 | DATNLET<br>SEQ ID NO: 23 | QQYDFLPLS<br>SEQ ID NO: 24 |
| 33 | R4-53-H | SYYMH<br>SEQ ID NO: 27 | IINPSGGSTSYAQKFQG<br>SEQ ID NO: 28 | DIGDYGDY<br>SEQ ID NO: 29 |
| | R4-53-L | GGNNIESKIVS<br>SEQ ID NO: 30 | DTDRPS<br>SEQ ID NO: 31 | QVWDSNSDHVI<br>SEQ ID NO: 32 |
| 34 | R4-54-H | SYGMH<br>SEQ ID NO: 35 | VISYDGSDKDYADSVKG<br>SEQ ID NO: 36 | DDYDSTYYFDN<br>SEQ ID NO: 37 |
| | R4-54-L | SGDILADQYAS<br>SEQ ID NO: 38 | HDTKRPS<br>SEQ ID NO: 39 | QAWDINTAWV<br>SEQ ID NO: 40 |
| 37 | R4-62-H | NFAMT<br>SEQ ID NO: 43 | TISGRGDEPFYADSVKG<br>SEQ ID NO: 44 | GGHFSSWDY<br>SEQ ID NO: 45 |
| | R4-62-L | TRSSGSIASNYVQ<br>SEQ ID NO: 46 | EDIERPS<br>SEQ ID NO: 47 | QSYDSSSYV<br>SEQ ID NO: 48 |
| 38 | R4-63-H | DYYMH<br>SEQ ID NO: 51 | LVDPEDGETIYAEKFQG<br>SEQ ID NO: 52 | IGRPPDY<br>SEQ ID NO: 53 |
| | R4-63-L | SGSSSNIGNNYVS<br>SEQ ID NO: 54 | DNNKRPS<br>SEQ ID NO: 55 | GTWDSSLSVWV<br>SEQ ID NO: 56 |
| 49 | R4-93-H | SYAMH<br>SEQ ID NO: 59 | VISYDGSNKYYADSVKG<br>SEQ ID NO: 60 | DTELQLWSGGYFDY<br>SEQ ID NO: 61 |
| | R4-93-L | TRSSGSIAHNYVQ<br>SEQ ID NO: 62 | DDDQRPS<br>SEQ ID NO: 63 | QSFDDSNWV<br>SEQ ID NO: 64 |

| | | Sequence | | |
|---|---|---|---|---|
| No. | Name | CDR1 | CDR2 | CDR3 |
| 2 | 293R3-2-H | SSNWWS<br>SEQ ID NO: 67 | EIYHSGSTNYNPSLRS<br>SEQ ID NO: 68 | DQRMEDDAFDI<br>SEQ ID NO: 69 |
| | 293R3-2-L | TGTSSDVGGYNYVS<br>SEQ ID NO: 70 | DVSNRPS<br>SEQ ID NO: 71 | SSYTSSSTLYV<br>SEQ ID NO: 72 |

TABLE 2-continued

| | | | | |
|---|---|---|---|---|
| 4 | 293R3-4-H | DYYIH<br>SEQ ID NO: 75 | FVDPENGETIYAEKFQG<br>SEQ ID NO: 76 | DRDYDDSSGNAFDI<br>SEQ ID NO: 77 |
| | 293R3-4-L | SGDILGDEYAF<br>SEQ ID NO: 78 | LDTRRPS<br>SEQ ID NO: 79 | QGWDSSTALYV<br>SEQ ID NO: 80 |
| 5 | 293R3-5-H | DYYMH<br>SEQ ID NO: 83 | LVDPEDGETIYAEKFQG<br>SEQ ID NO: 84 | ASPREEMPYYFDY<br>SEQ ID NO: 85 |
| | 293R3-5-L | SGDILADQYAS<br>SEQ ID NO: 86 | HDTKRPS<br>SEQ ID NO: 87 | QAWDINTAWV<br>SEQ ID NO: 88 |

*CDR regions are defined by CHOTHIA, H represents heavy chain, and L represents light chain.

Binding and neutralizing ability of fully human mAbs targets against CHI3L1.

Figure 4A:
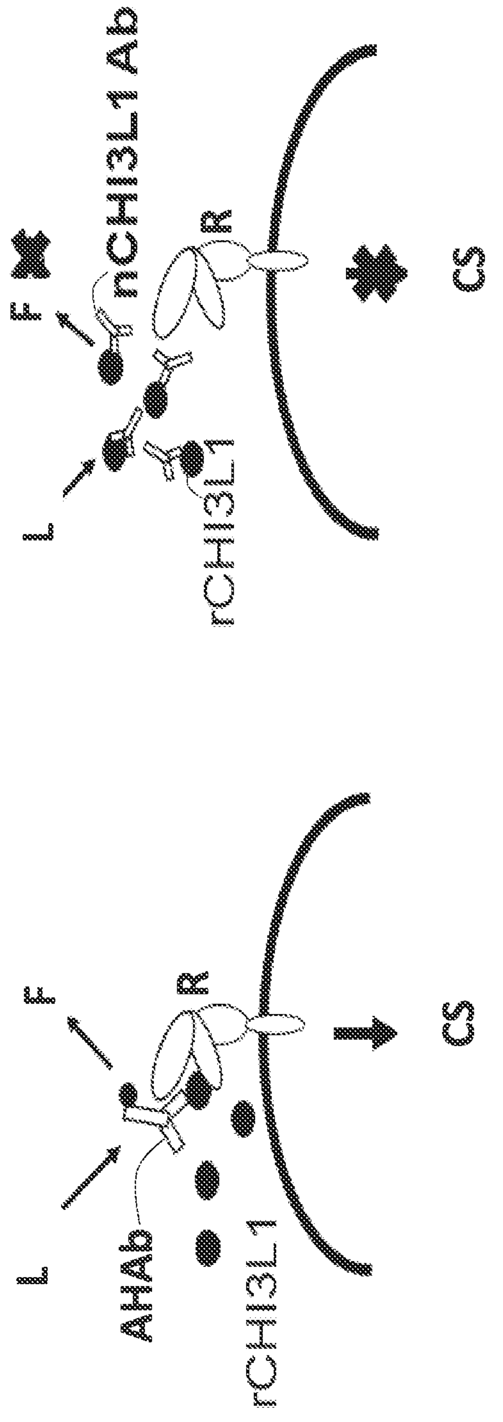
FIGS. 4A to 4C show that fully human mAbs attenuate the binding affinity between recombinant CHI3L1 (rCHI3L1) and its receptor(s) on cancer cells.
Figure 4B:
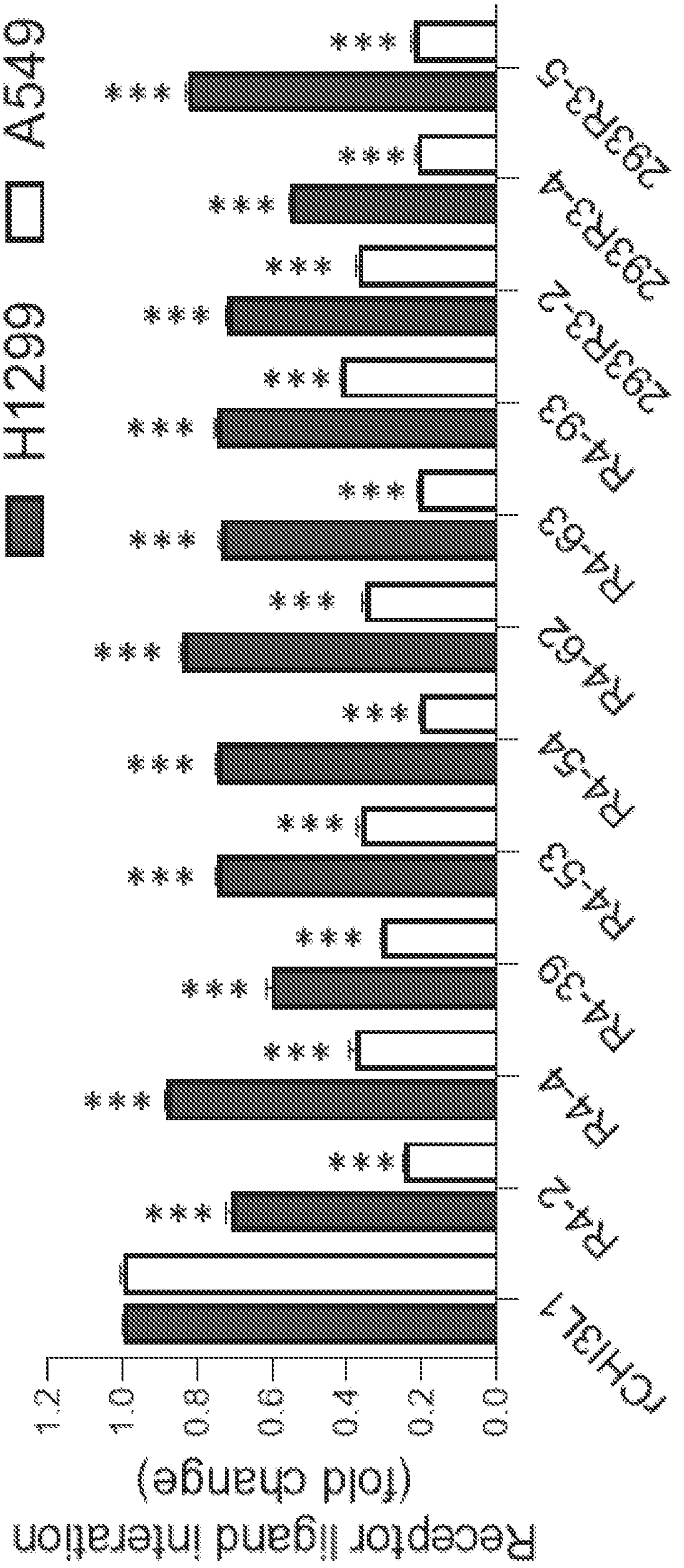

CHI3L1 have been reported to interact with several receptors on cancer cells, and trigger downstream signaling for cancer cell growth, proliferation and anti-apoptosis (Kamba et al. 2013; Lee et al. 2016). To investigate the blocking effect of our phage-displayed fully human monoclonal neutralizing antibodies (mAbs) between CHI3L1 and its receptor(s) on cancer cells, we initially screened 11 clones of mAbs for the binding affinity and blockage of CHI3L1-receptor(s) interaction on human lung cancer cell lines (H1299 and A549). His-tagged rCHI3L1 was added for CHI3L1-receptor(s) interaction. Anti-His antibody AHAb with fluorescent F recognized CHI3L1-receptor(s) R complex for detection (left, FIG. 4A). Once fully human mAbs (nCHI3L1 Ab) blocked the CHI3L1-receptor(s) interaction, the fluorescent F signals were decreased (right, FIG. 4A) and cell signaling CS was blockade. Quantification of results by flow cytometry showed that rCHI3L1 binding to cells were all reduced upon 11 clones of mAbs treatment, indicating the blockage of interaction between CHI3L1 and its receptor(s) (FIG. 4B).

Figure 4C:
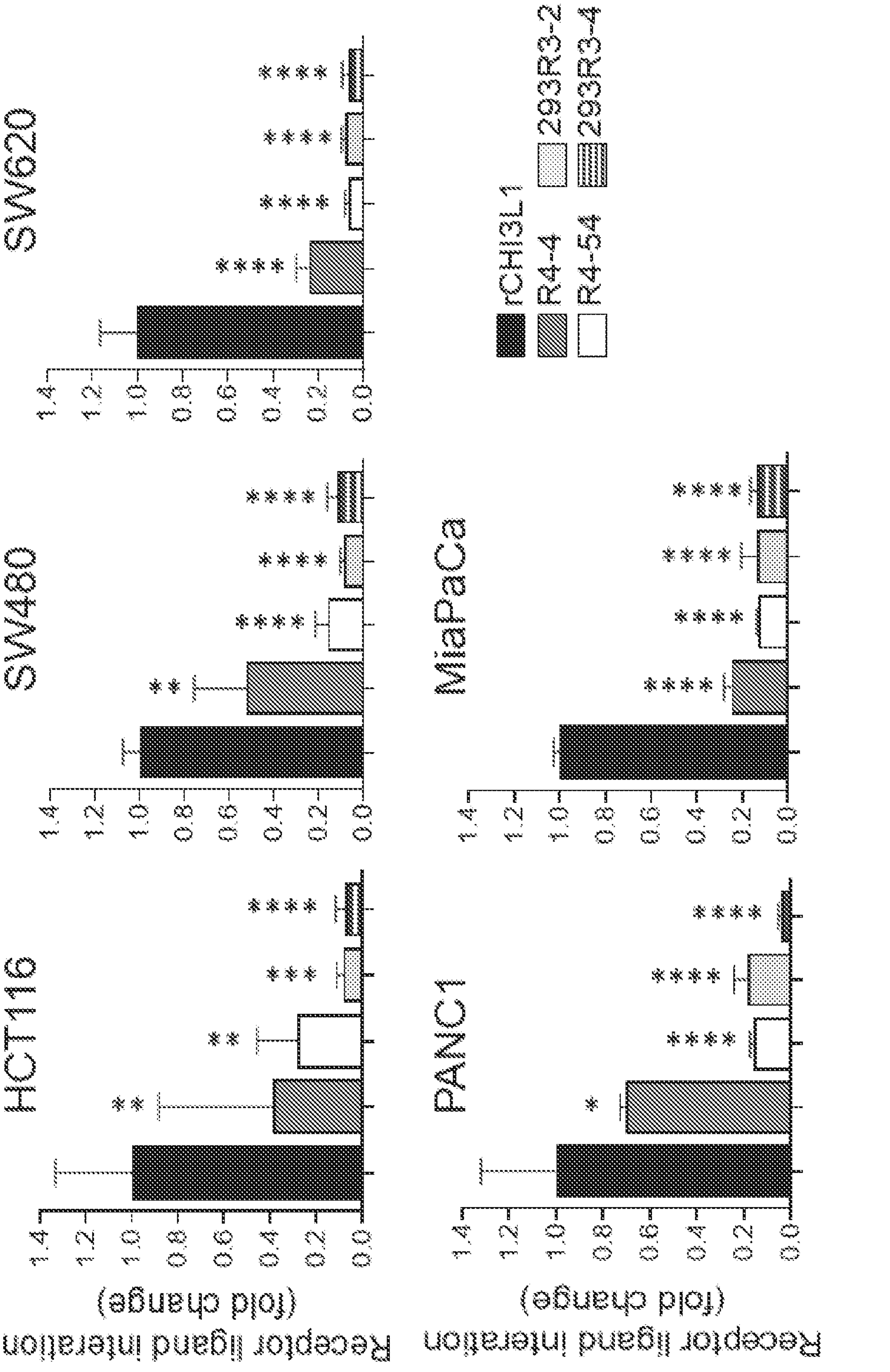
Figure 4G:
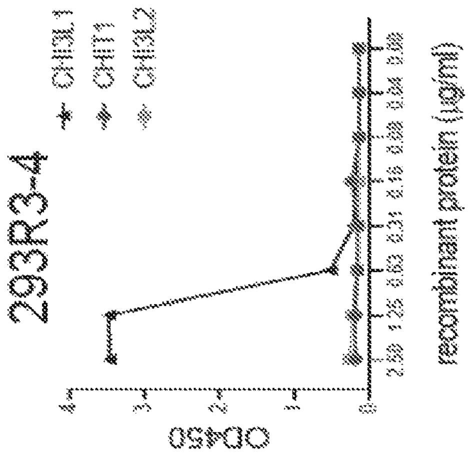
FIGS. 4D to 4G show fully human mAbs clone R4-4, R4-54, 293R3-2, and 293R3-4 specifically bound to human rCHI3L1.
Figure 4F:
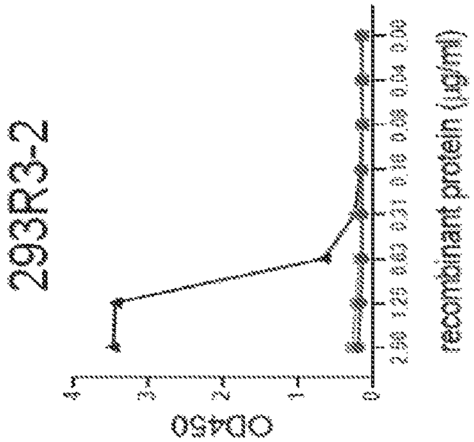
Figure 4E:
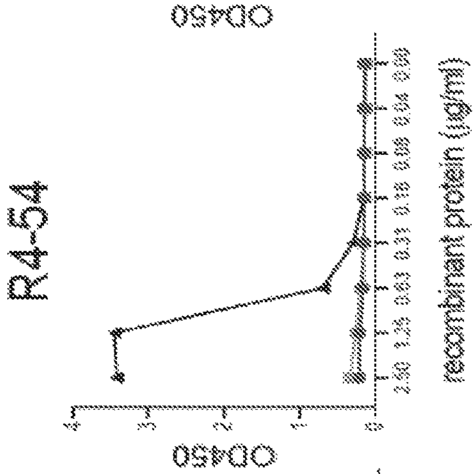
Figure 4D:
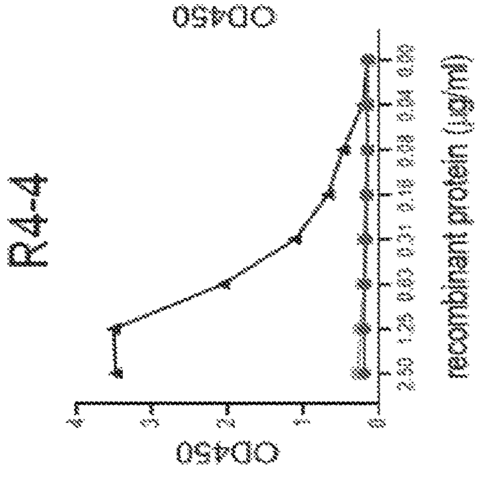

Four selected clones of mAbs including R4-4, R4-54, 293R3-2, and 293R3-4 were further tested for blocking effect on human colorectal (HCT116, SW480, and SW620) and pancreatic cancer cell lines (PANC1 and MiaPaCa-2). The rCHI3L1 binding to these cells was significantly reduced by four selected mAbs (FIG. 4C). The data was showed as mean±S.D. (n=3 per group). P values were determined by one-way ANOVA. * $P<0.05$,  $P<0.01$, * $P<0.001$, ** $P<0.0001$. For binding specificity examination, we further coated different concentration of recombinant CHI3L1 protein, and two other major proteins in chitinase family including human chitotriosidase-1 (CHIT1) and CHI3L2 from 2.5 μg/ml to 0 μg/ml, on 96-well plate. Results of ELISA assay indicated that our four selected mAbs (1 μg/ml) specifically recognized CHI3L1 but no other chitinase proteins (FIG. 4D, FIG. 4E, FIG. 4F, FIG. 4**G).

The fully human mAbs inhibit cell growth signaling pathways in different cancer cells.

Figure 5A:
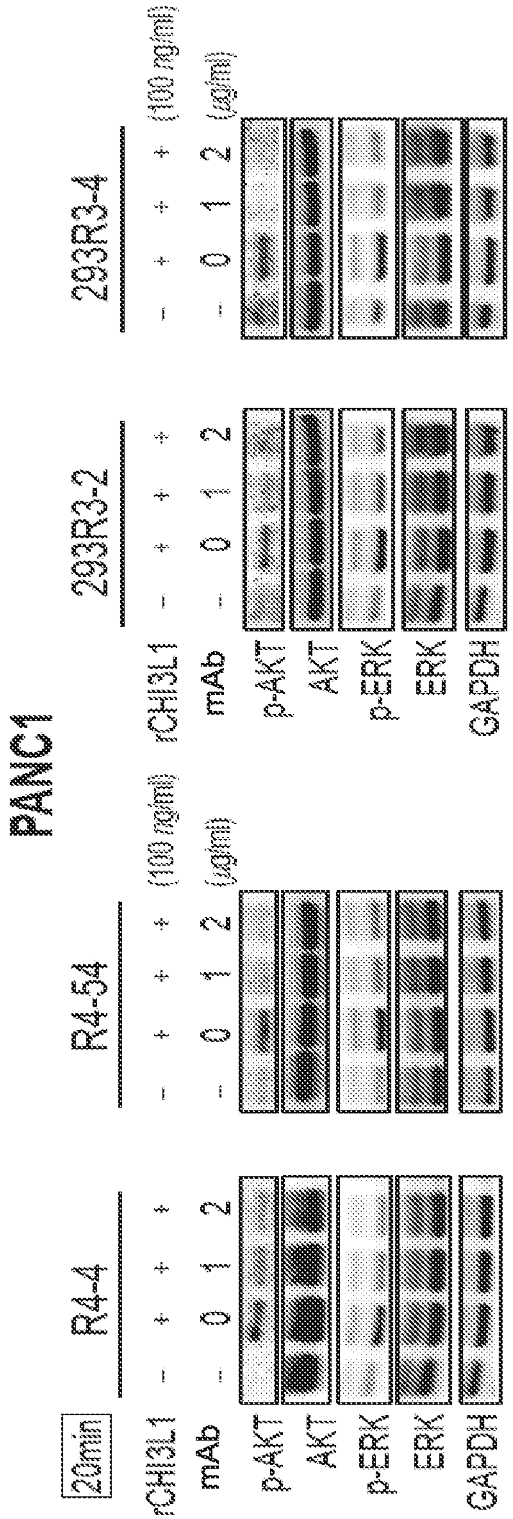
FIGS. 5A to 5C show fully human mAbs inhibit AKT/ERK signals induced by rCHI3L1 in different cancer cell lines.
Figure 5B:
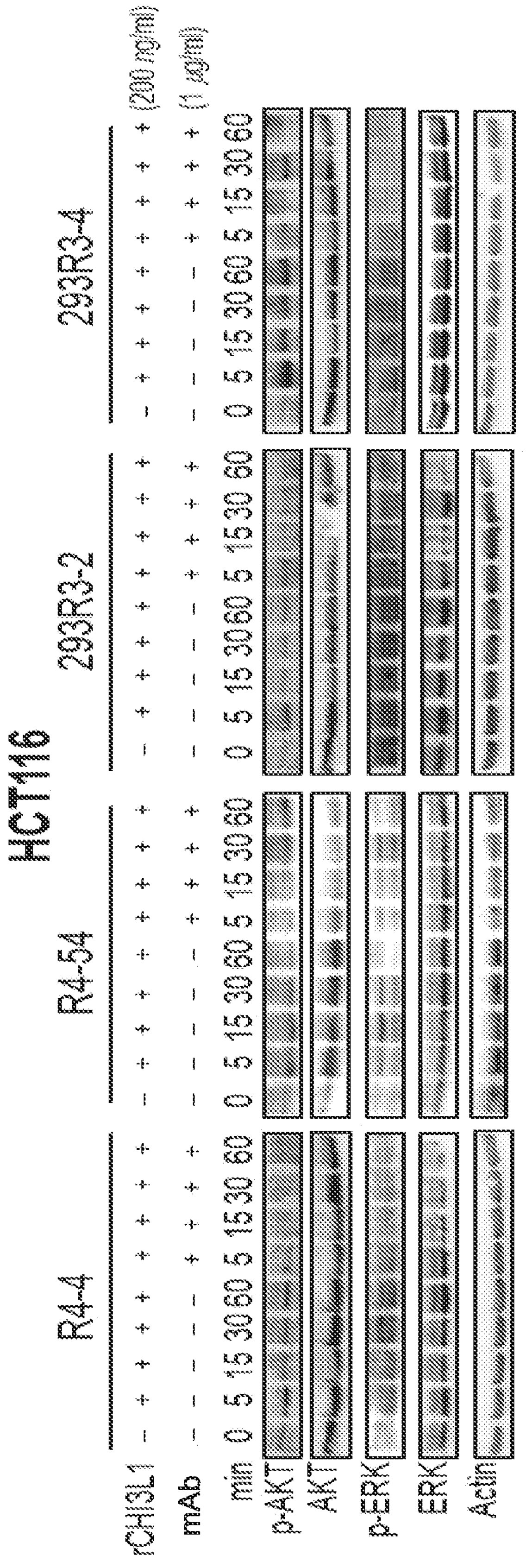
Figure 5C:
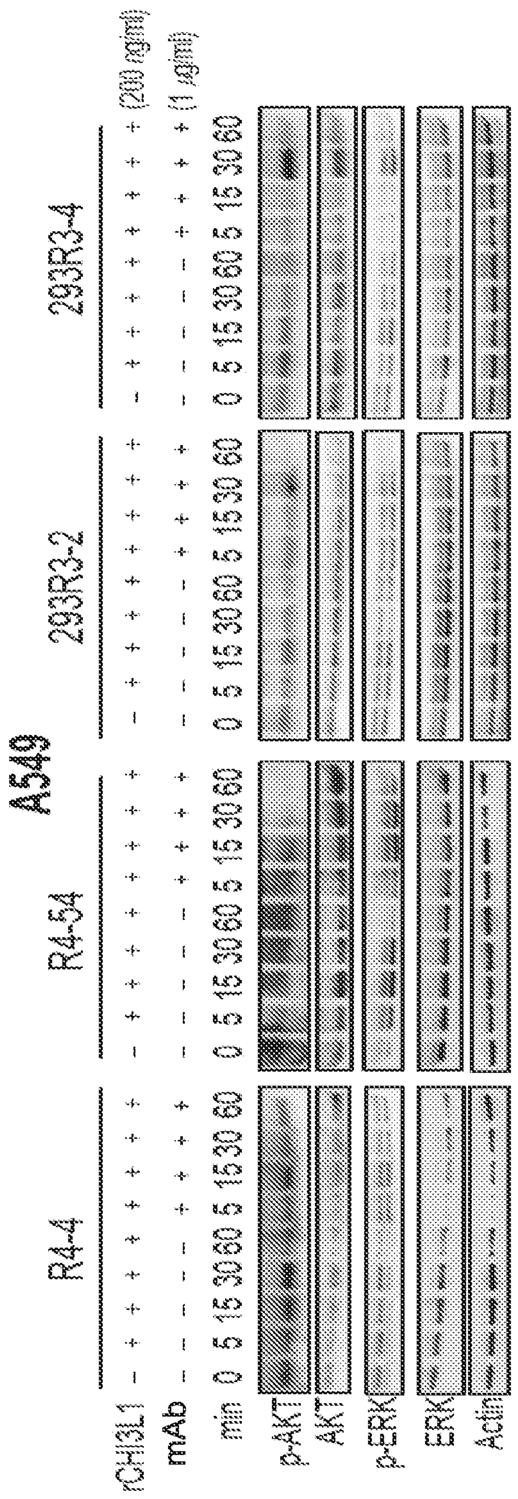

The involvement of CHI3L1 in intracellular signaling pathways has been reported. For example, CHI3L1 binding to CD44 activates protein kinase B (AKT) and extracellular signal-regulated kinase (ERK) signaling to promote cancer progression (Chen, Jiang et al. 2021). Thus, we tested whether mAb clones R4-4, R4-54, 293R3-2, and 293R3-4 could attenuate AKT and ERK phosphorylation in human pancreatic (PANC1), colorectal (HCT116), and lung (A549) cancer cell lines. PANC1 cells were treated with rCHI3L1 (100 ng/ml) only or rCHI3L1 with different dose of mAbs as indicated for 20 minutes. Immunoblot analysis revealed that four clones of mAb inhibited p-AKT and p-ERK levels induced by rCHI3L1 in a dose dependent manner in PANC1 cells (FIG. 5A). Inhibition of p-AKT and p-ERK by mAbs were also observed in HCT116 and A549 cells in a time-dependent manner (FIG. 5B and FIG. 5C). Overall, mAbs consistently downregulated CHI3L1-induced p-AKT and p-ERK levels in PANC1, HCT116, and A549 cells.

Fully human mAbs attenuate growth and migration behaviors in lung, pancreas and colon cancer cell lines.

Figure 6A:
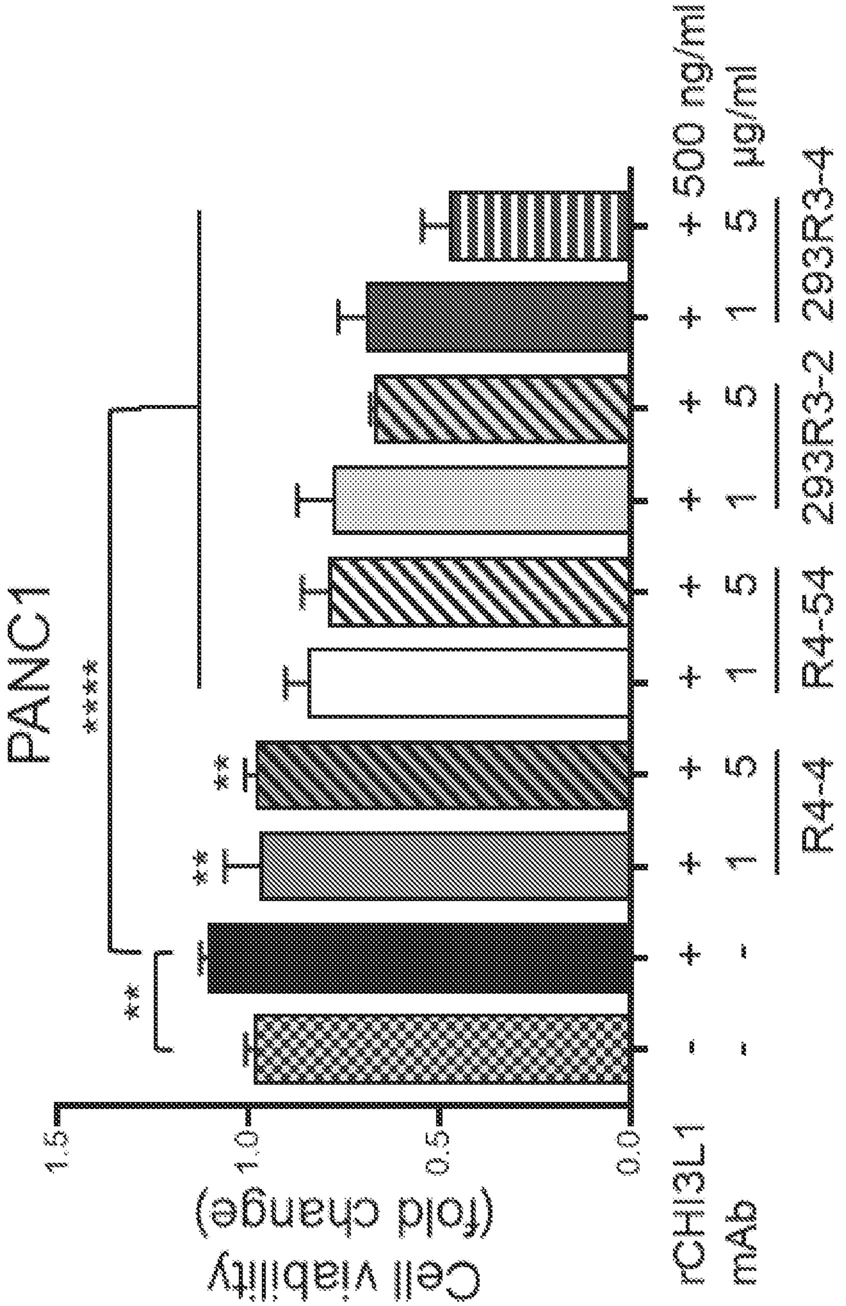
FIGS. 6A to 6D show fully human mAbs reduce cell viability and cell proliferation induced by rCHI3L1.
Figure 6B:
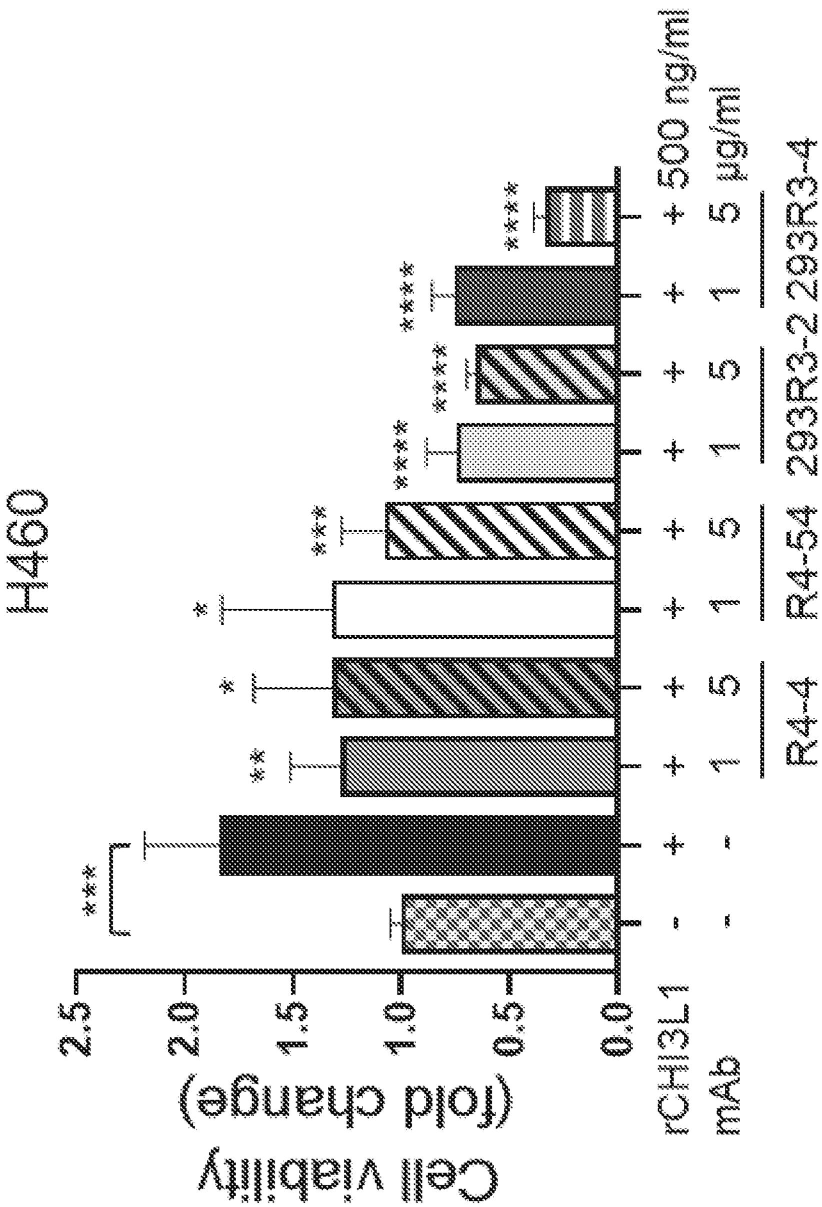
Figure 6C:
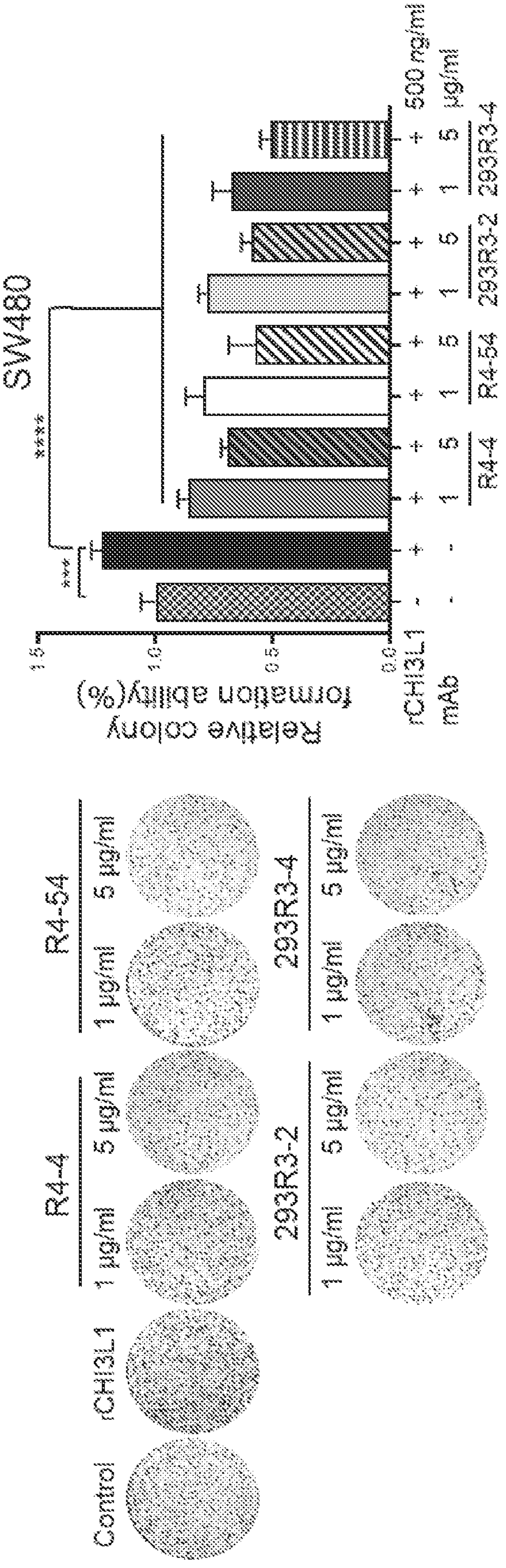
Figure 6D:
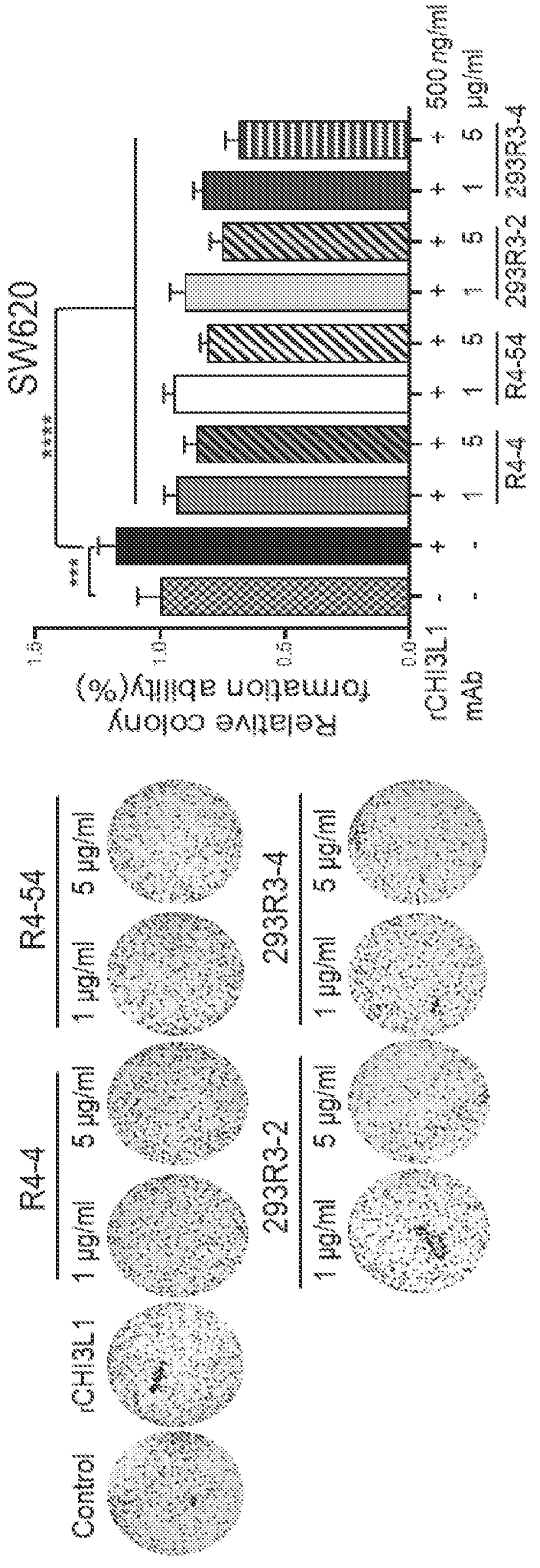

PI3K/AKT/mTOR signaling pathway is important in regulating cell proliferation, survival and migration (Xu et al. 2020). Therefore, we investigated the effect of four selected mAbs on cancer cell behaviors. Human pancreatic (PANC1) and large cell cancer of the lung (H460) cells were treated with rCHI3L1 only or together with mAbs at two doses, and then subjected to cell counting kit 8 (CCK-8) cell viability assay. Both doses of mAbs treatment reduced the viability of PANC1 and H460 cells (FIG. 6A and FIG. 6B). In addition, stimulation with pro-tumor protein as rCHI3L1 resulted in loss of density-dependent growth, and thus induced foci formation ability of SW480 and SW620 cells. With mAbs R4-4, R4-54, 293R3-2, and 293R3-4 treatment, the number of foci was decreased in a dose-dependent manner (FIG. 6C and FIG. 6D). The data was showed as mean±S.D. (n=3 per group). P values were determined by one-way ANOVA. * $P<0.05$,  $P<0.01$, * $P<0.001$, **** $P<0.0001$.

Figure 7A:
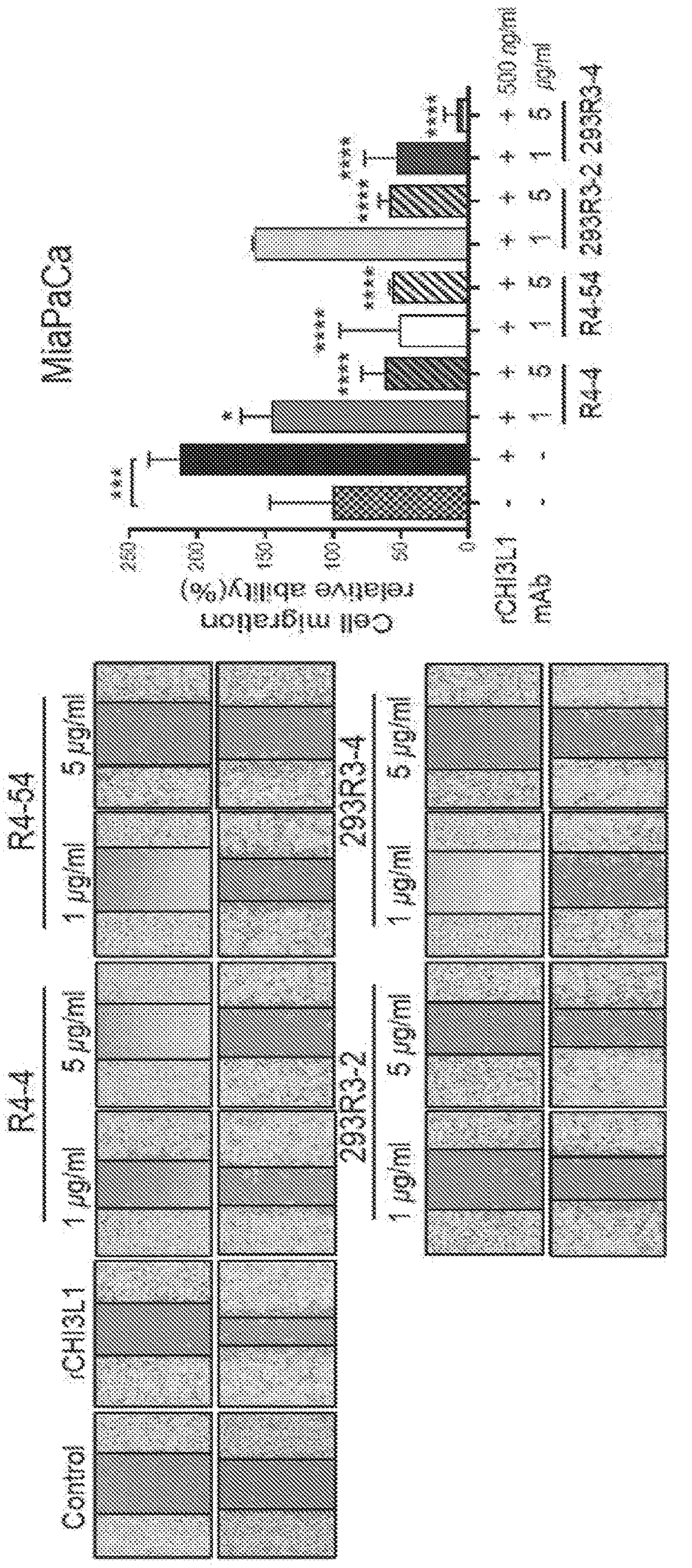
FIGS. 7A to 7C show fully human mAbs reduce cell migration ability induced by rCHI3L1.
Figure 7B:
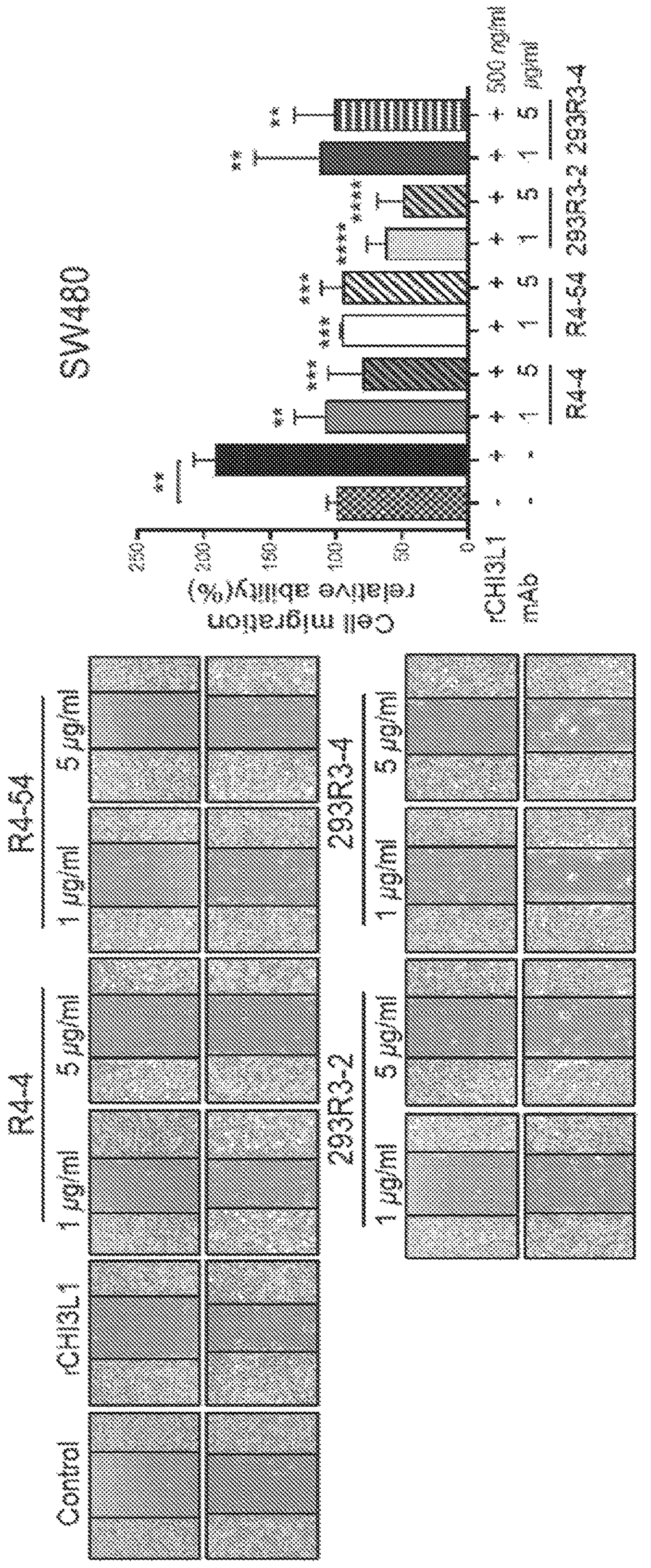
Figure 7C:
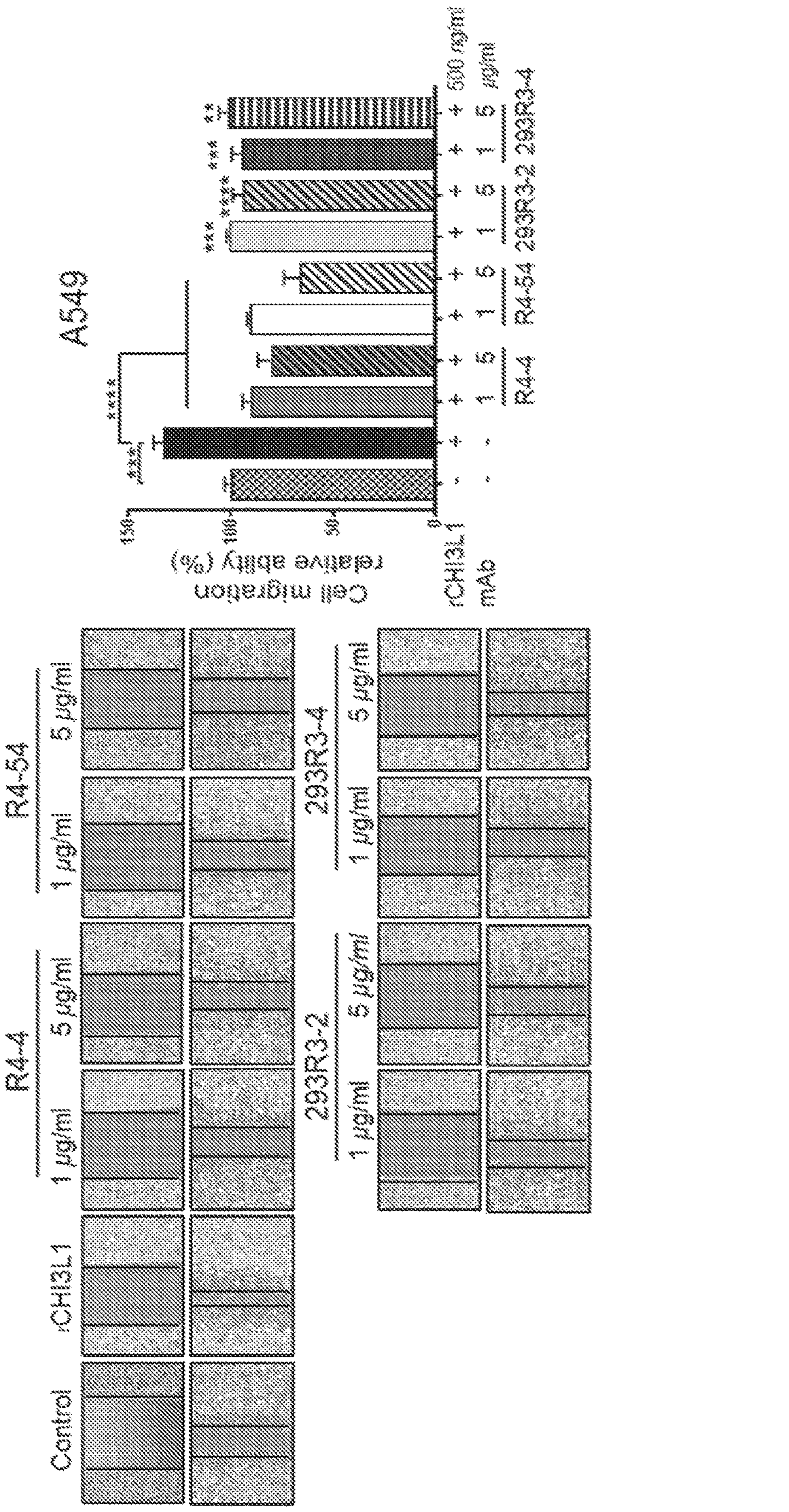

Since AKT regulates cell migration, we further performed wound healing assay to examine the anti-migratory effect of mAbs on pancreatic (MiaPaCa-2), colorectal (SW480), and lung (A549) cells. We observed that after 16 hours, the wound closure area was increased compared to that in control groups upon rCHI3L1 treatment. Our four selected clones of mAbs significantly reduced cell migration ability induced by rCHI3L1 (FIG. 7A, FIG. 7B, and FIG. 7C). Taken together, our fully human monoclonal CHI3L1 neutralizing antibody clones R4-4, R4-54, 293R3-2, and 293R3-4 blocked the CHI3L1 induced signaling and cell behaviors of tumor cells. The data was presented as mean±S.D. (n=3 per group). P values were determined by one-way ANOVA. * $P<0.05$,  $P<0.01$, * $P<0.001$, **** $P<0.0001$.

Fully human mAbs show immunostimulatory effects toward immune cells in vitro.

The plasma level of CHI3L1 in various cancer patients is significantly higher than that of healthy controls (Johansen et al. 2004). Besides the direct effect on tumor growth, CHI3L1 also plays roles in modulating tumor microenvironment (TME), such as promoting M2-like tumor associated macrophages (TAM) differentiation and Th1/Th2 inflammatory balance (Kawada et al. 2012). Macrophages rapidly alter their phenotype depending on the external stimuli. Some researches indicated that NF-κB activation triggers M2 polarization (Wang et al. 2014).

Figure 8A:
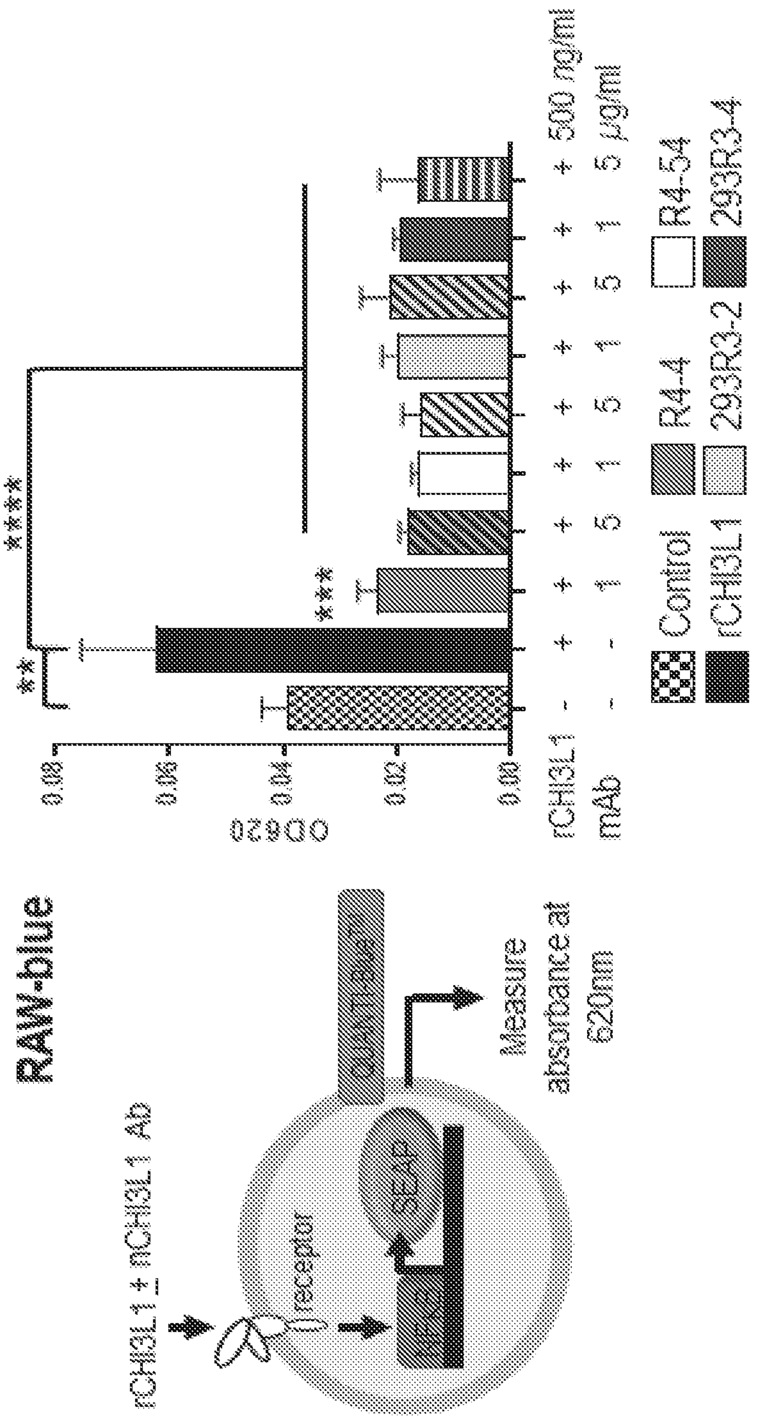
FIGS. 8A to 8E show that fully human mAbs modulated NF-κB signals and immune response.
Figure 8B:
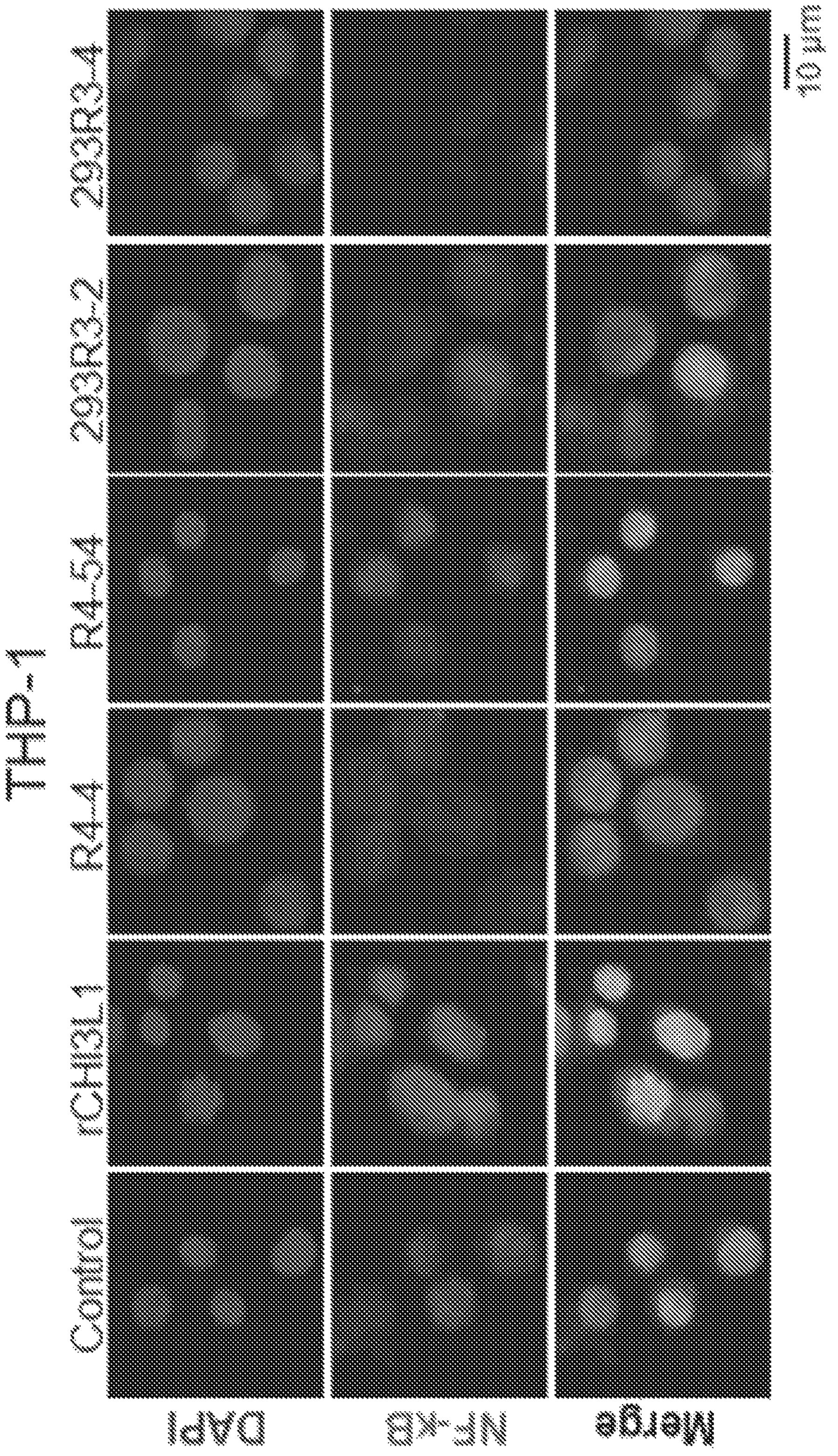
Figure 8C:
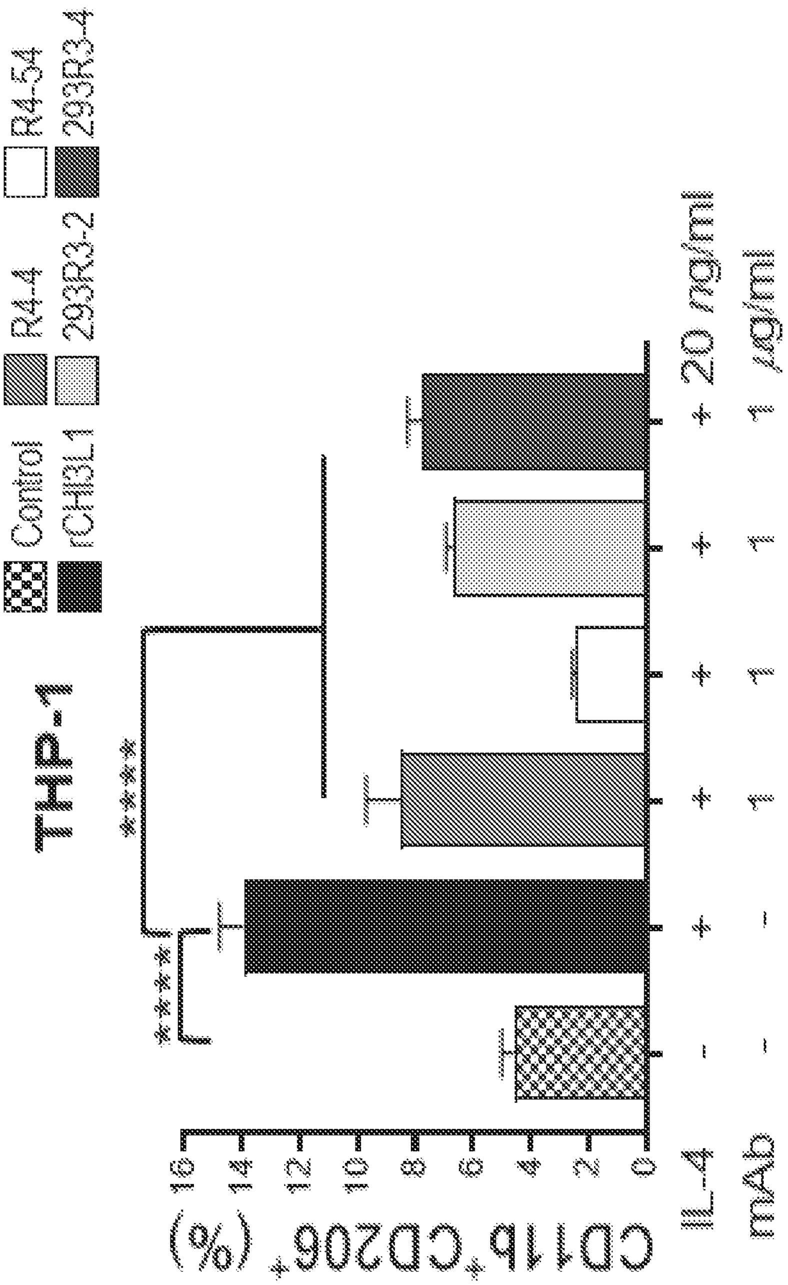
Figure 8D:
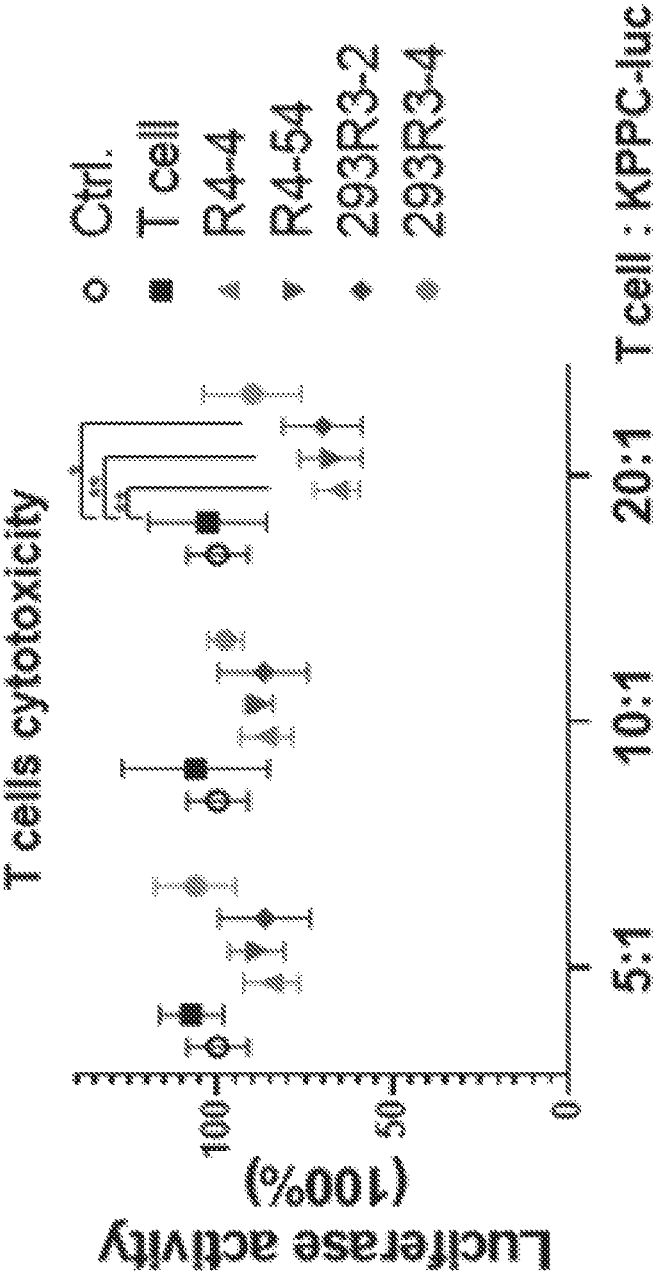
Figure 8E:
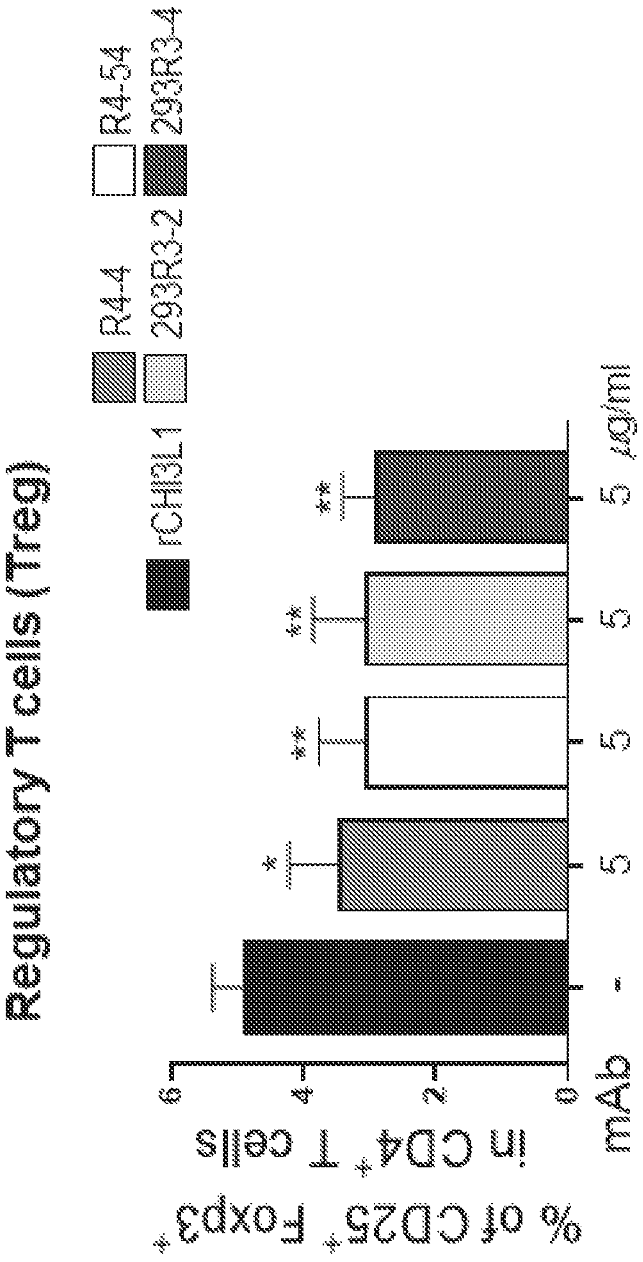

To determine the effect of mAbs on immune cells modulation, we investigated the polarization of macrophages and T cell function. We measured NF-κB activity by the secreted embryonic alkaline phosphatase (SEAP) reporter in murine macrophages, RAW-Blue™ cells. The results showed that rCHI3L1-induced NF-κB activity was largely attenuated by four selected mAb clones (FIG. 8A). Moreover, immunofluorescence data demonstrated that CHI3L1 enhanced NF-B translocation to nucleus, while the nuclear translocation decreased upon mAbs treatment (FIG. 8B). To further confirm the effect of mAbs on macrophages polarization, THP-1 macrophage cells, a monocyte isolated from peripheral blood from an acute monocytic leukemia patient, were treated with IL-4 for M2 polarization. Flow cytometry analysis revealed that four clones of mAb decreased the level of CD206 (an M2 maker) induced by IL-4 (FIG. 8C). Next, a co-culture assay was performed to assess anti-tumor T cell activity. Luciferase-expressing KPPC (KPPC-luc) cells were co-cultured with CD8 T cells isolated from spleen of KPPC-luc bearing C57BL/6 mice. The reduction of luciferase signals refers to T cell cytotoxicity. Compared to control group, treatment of mAbs significantly increased T cell cytotoxicity (FIG. 8D). Furthermore, we determined the effect of mAbs on regulatory T cells (Treg) differentiation by KPPC-luc and splenic $CD4^+$ T cells co-culture assay. Flow cytometry analysis showed that mAbs effectively decreased the percentage of KPPC-luc-induced Treg (FIG. 8E). Together, these data suggest that four selected CHI3L1 mAbs clones modulate immune cells from pro-tumor to anti-tumor phenotype in vivo and ex vivo.

Fully human mAbs mono-treatment exert anti-tumor effects in vivo.

Figure 9A:
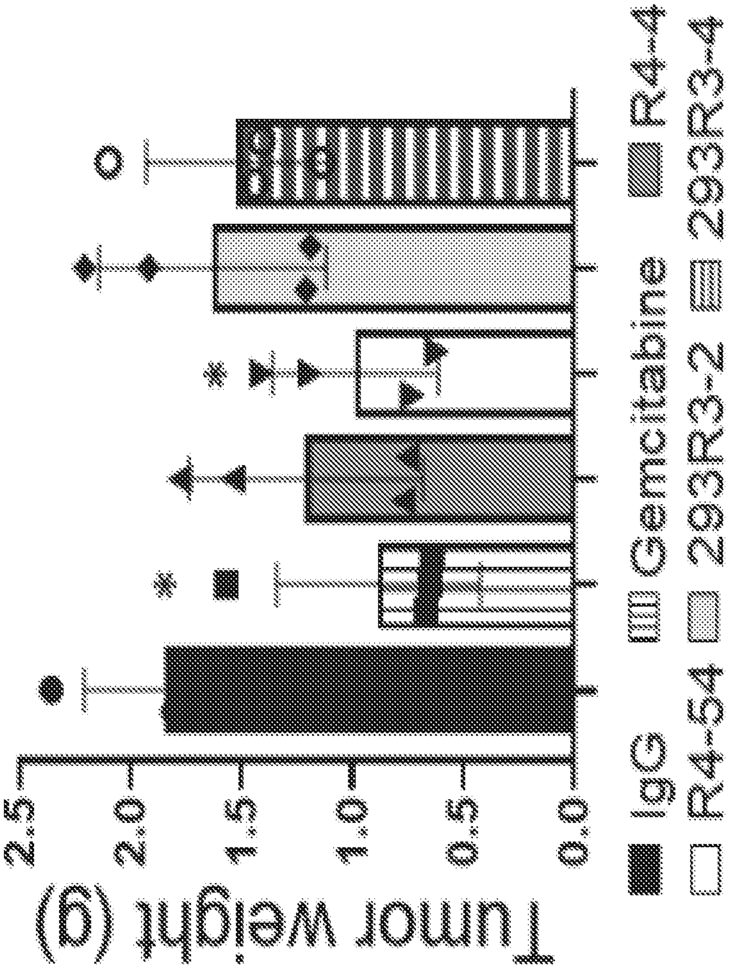
FIGS. 9A to 9I show that fully human mAbs exhibit tumor restriction effects in MiaPaCa orthotopic NOD SCID mice model.
Figure 9B:
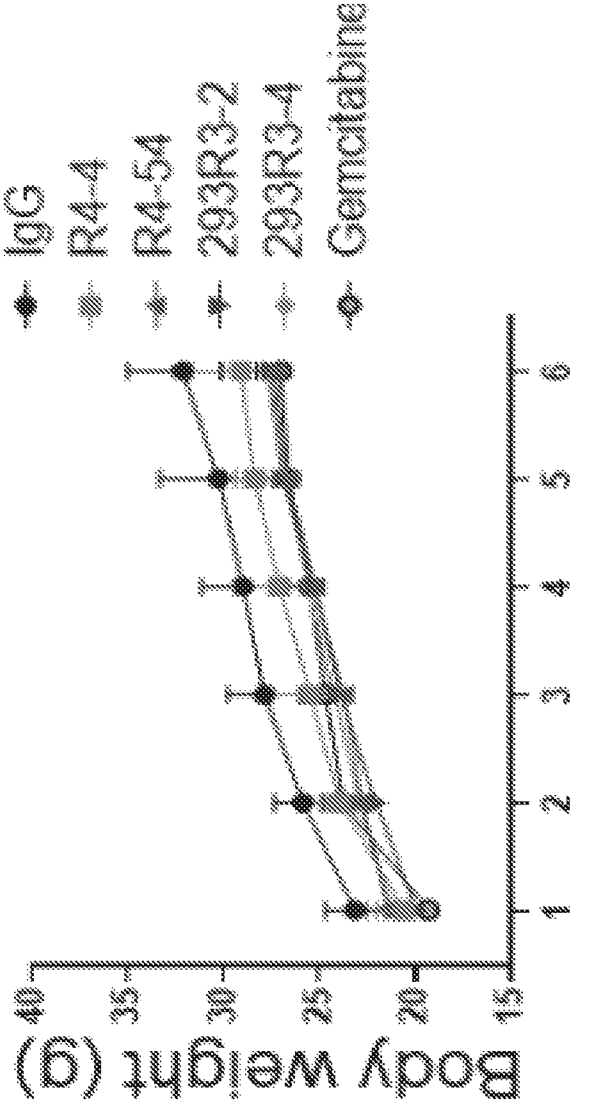
Figure 9C:
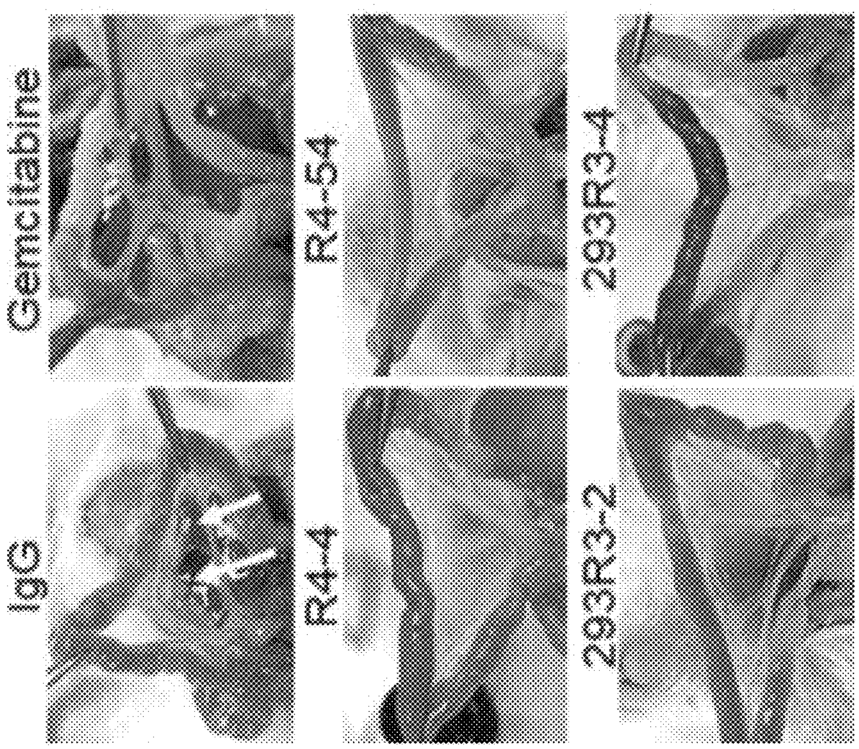
Figure 9D:
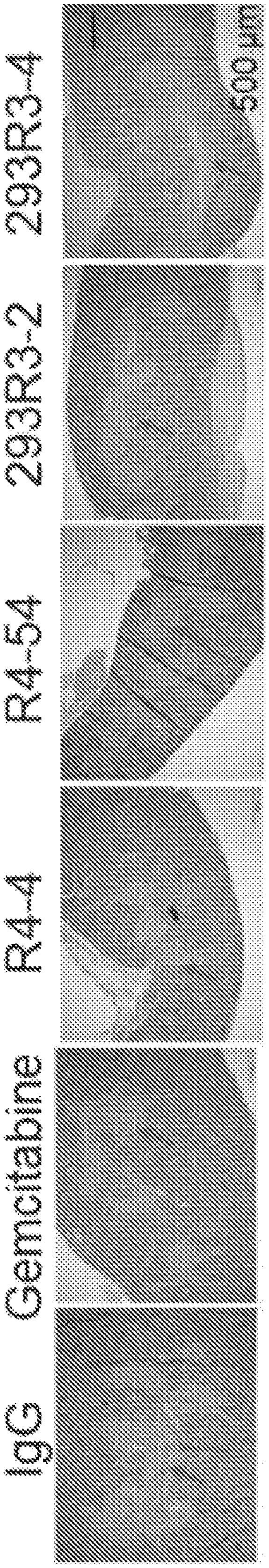
Figure 9E:
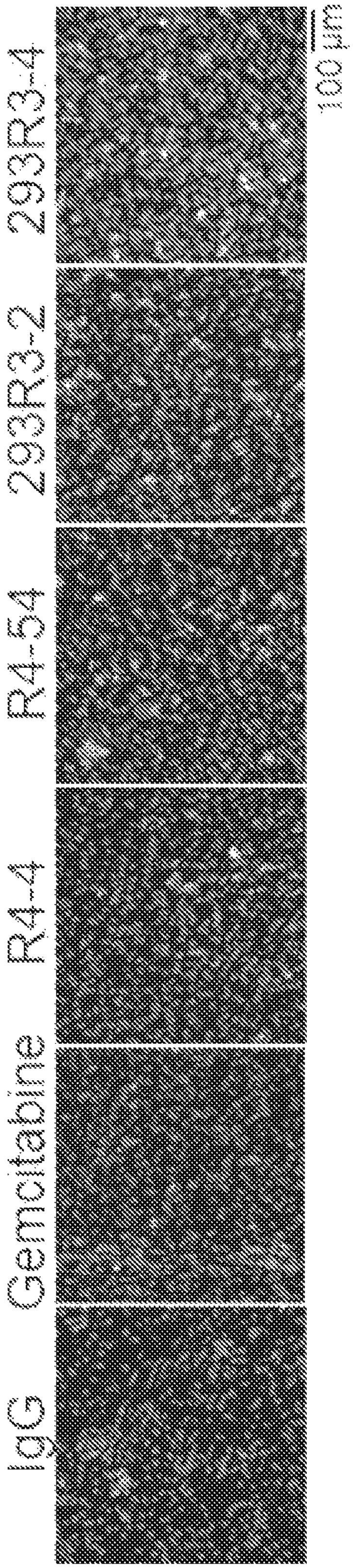
Figure 9F:
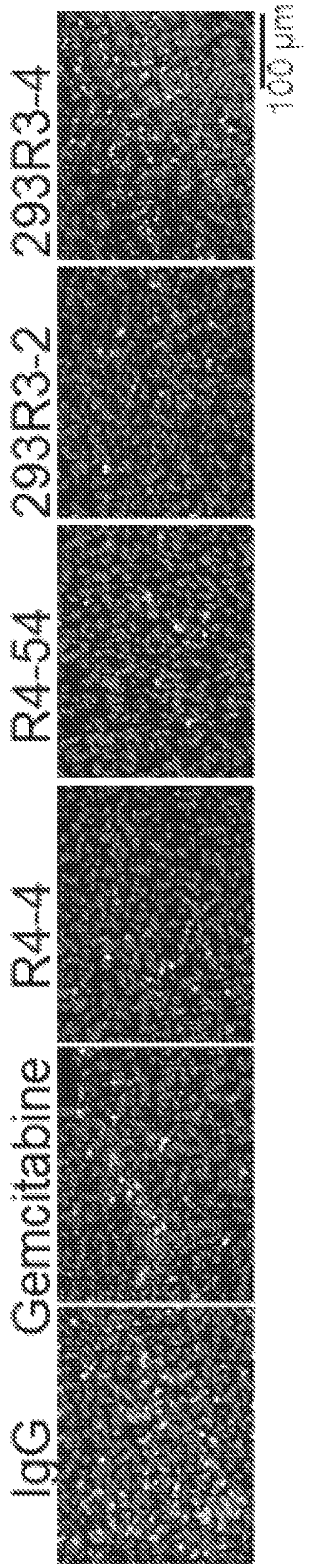
Figure 9G:
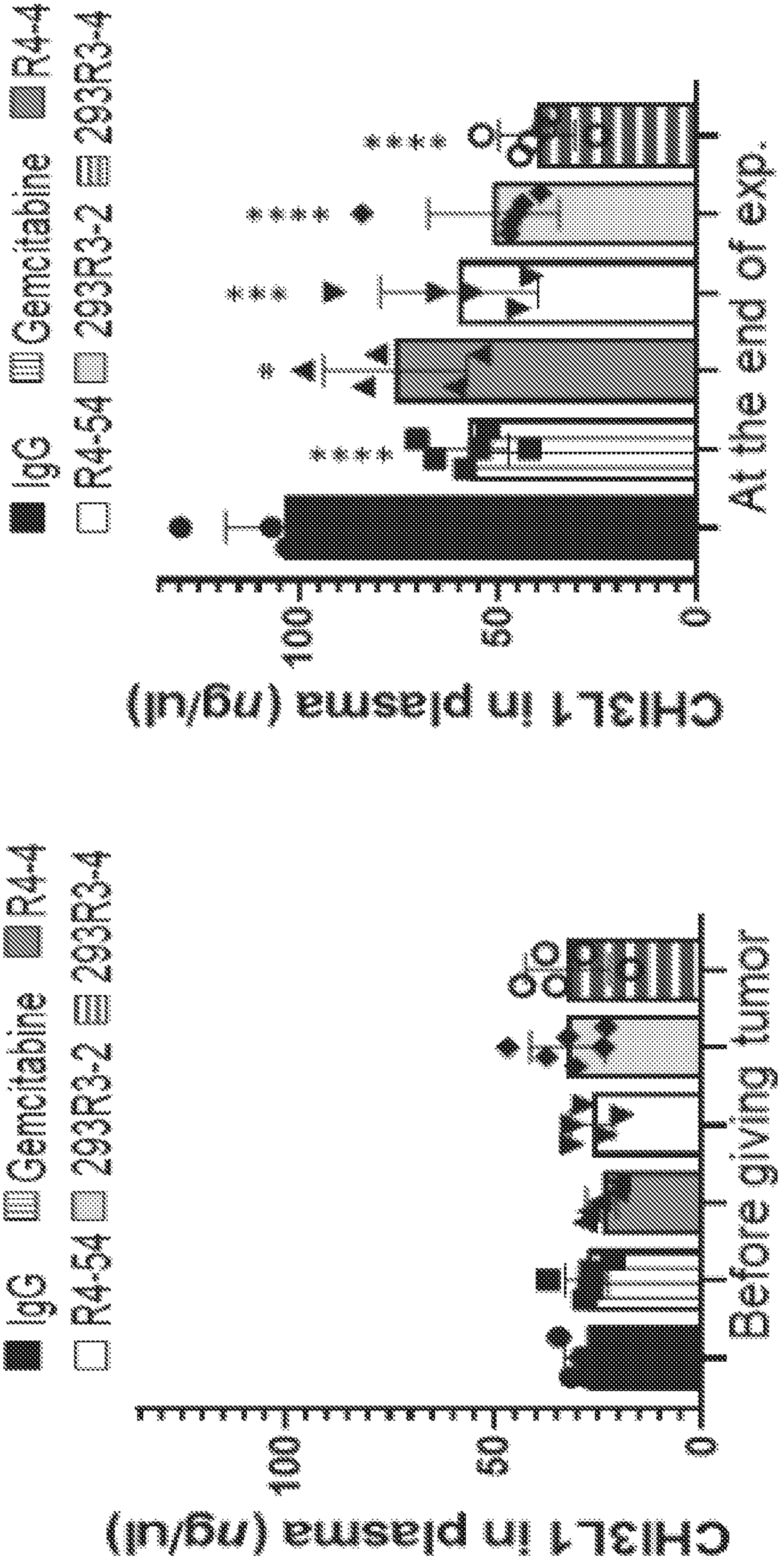
Figure 9H:
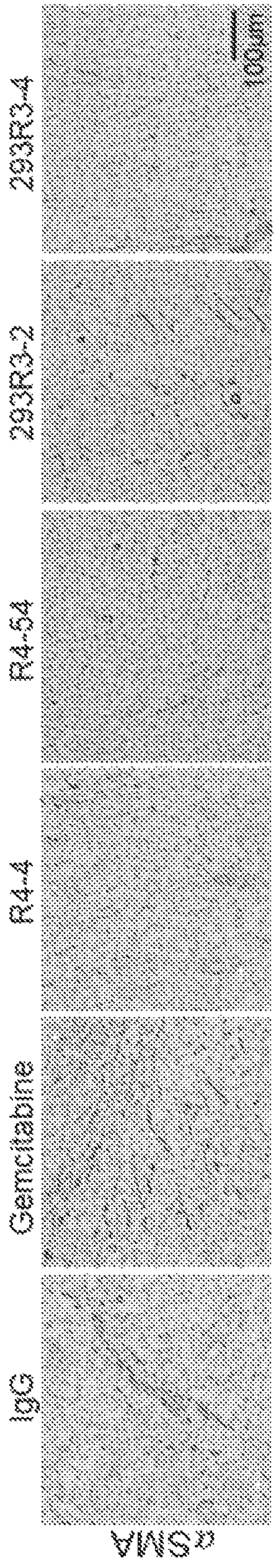
Figure 9I:
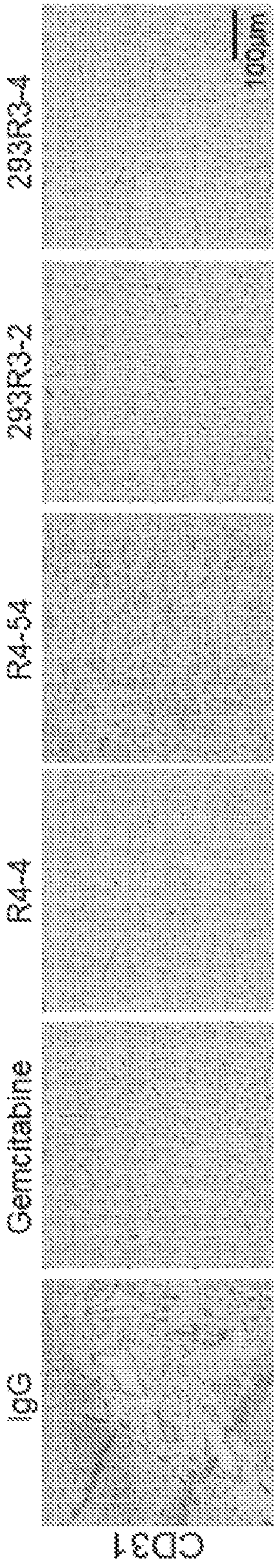

For in vivo verification, four clones of mAb (5 mg/kg) were given to MiaPaCa-2-bearing NOD-SCID mice and compared with gemcitabine (50 mg/kg) for anti-tumor efficacy. Specifically, experimental design of tumor growth inhibition in vivo. MiaPaCa cells ($5\times10^6$) were injected into pancreas of NOD-SCID mice at Day 0. The mAb clone R4-4, R4-54, 293R3-2, 293R3-4 or control IgG Ab was given by tail-vein injection (i.v.) at indicated time points (Day 7, Day 14, Day 21, and Day 28). Gemcitabine was given through intraperitoneal injection (i.p.) also at indicated time points (Day 7, Day 14, Day 21, and Day 28) and served as a positive drug control. Mice were sacrificed on day 34. All tumors in treatment groups are smaller than IgG control group (FIG. 9A) without significant weight loss (FIG. 9B). Moreover, mesentery metastases were observed only in IgG control group (indicated as arrow) but not in other treated groups (FIG. 9C). Although there was spleen metastasis in each group, the tumor nodules were obviously smaller in R4-4 treated group (FIG. 9D). In addition to tumor growth, we also verified infiltrated macrophages in tumor sections. Immunofluorescence (IF) results showed that more macrophages other than M2 phenotype ($CD206^+$ marker), which most likely the M1 macrophages ($F4/80^+$ marker) were stained within tumors of mAbs treated groups (FIG. 9E). Notably, the level of CHI3L1 in intratumoral region and plasma of the treated group were lower than IgG control group at the end of experiment (FIG. 9F and FIG. 9G). Since fibrosis and angiogenesis are two major issues during tumor progression, we compared the fibrosis and angiogenesis level within each groups. Fibrosis which was indicated by α-SMA showed obviously decrease in R4-4 and R4-54 treated groups comparing to IgG control and gemcitabine groups, while angiogenesis indicated by CD31 expression decreased in every treatment groups (FIG. 9H and FIG. 9I). Altogether, within four clones of mAbs showed great efficacy in all anti-tumor and TME ameliorating parameters examined in vivo.

Fully human mAb R4-4 mono-treatment exert anti-tumor and TME ameliorating effects in immunocompetent mice model in vivo.

Figure 10A:
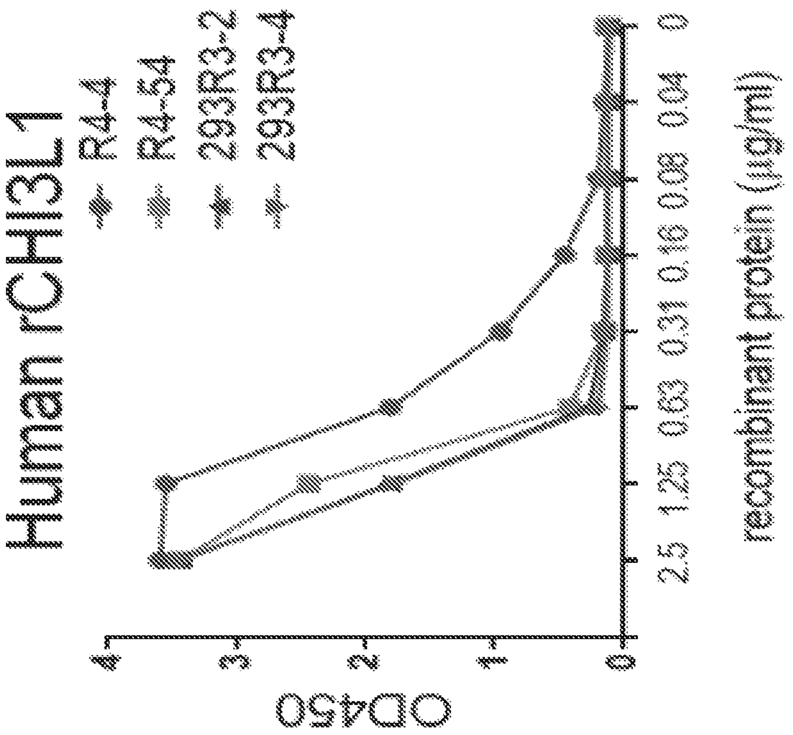
FIGS. 10A to 10B show binding curves of ELISA assay indicated the binding of R4-4 (circle), R4-54 (square), 293R3-2 (triangle), and 293R3-4 (reverse triangle) to (FIG. 10A) human rCHI3L1 and (FIG. 10B) mouse rCHI3L1.
Figure 10B:
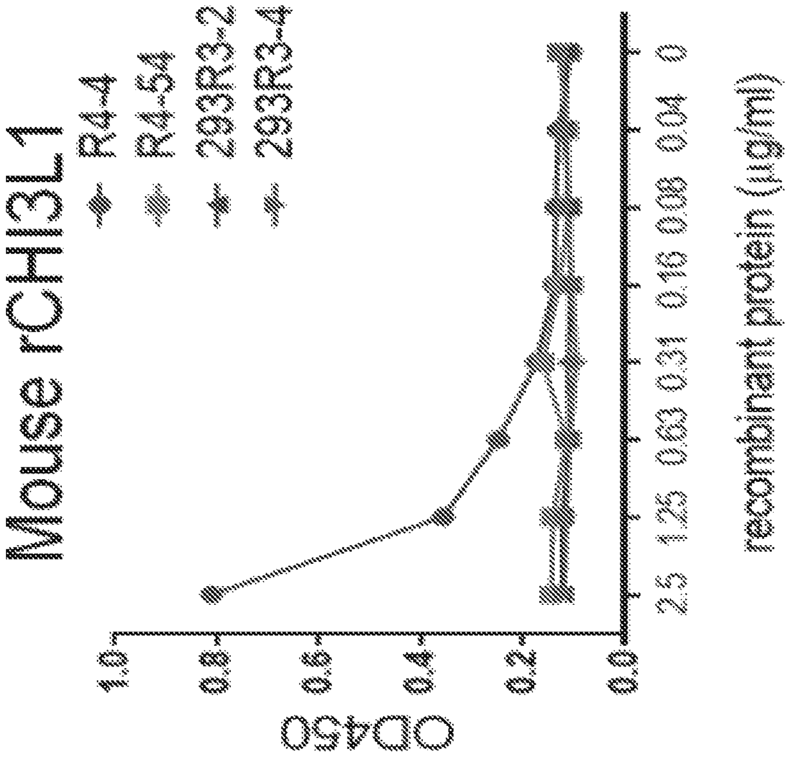
Figure 10C:
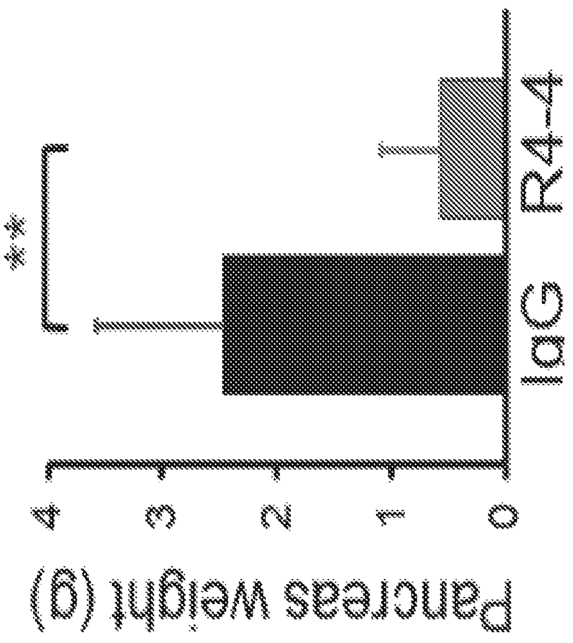
FIGS. 10C to 10E show that fully human mAb clone R4-4 shows anti-cancer effect in pancreatic KPPC-luc orthotopic C57BL/6J mice model.
Figure 10D:
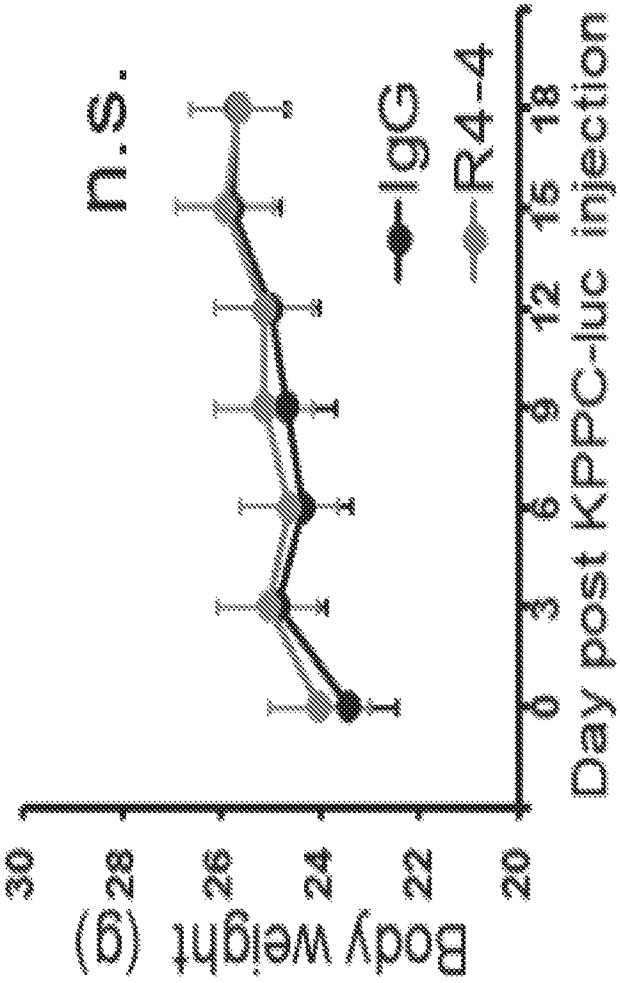
Figure 10E:
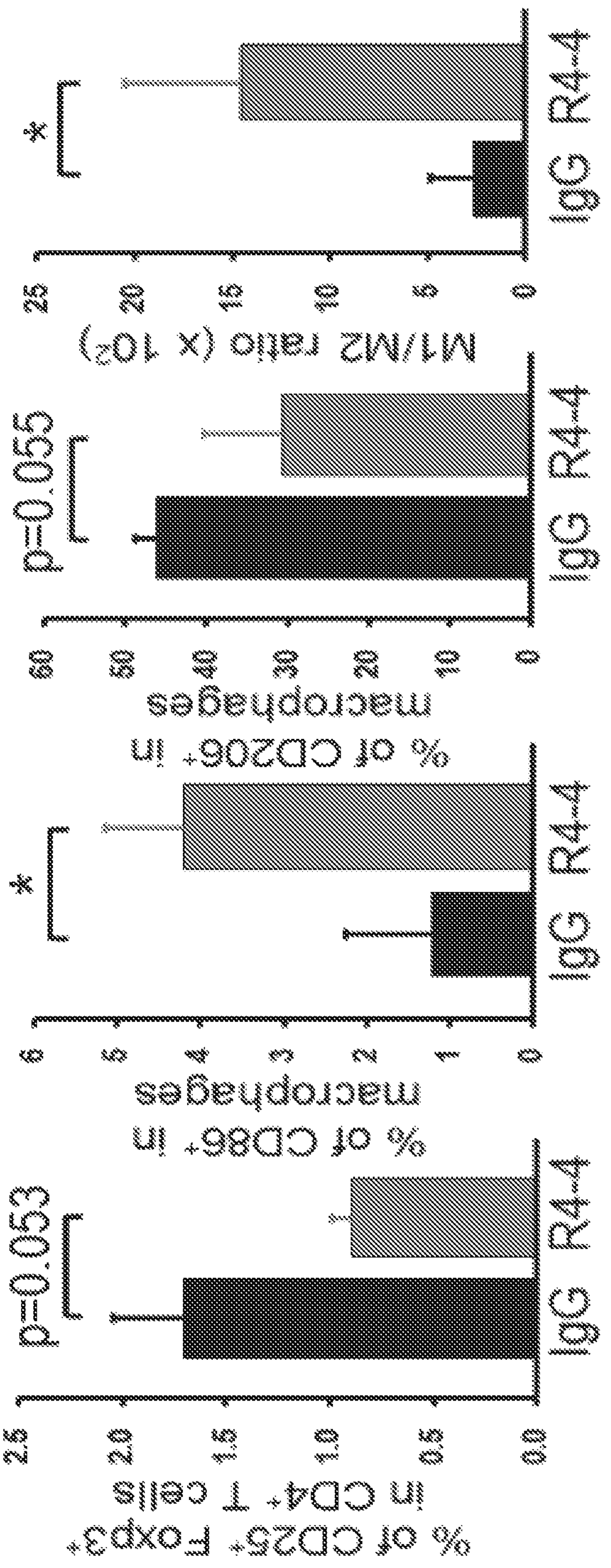

R4-4 mAb is the only one that could cross-react with murine CHI3L1 (FIG. 10A and FIG. 10B). Thus, we established orthotopic animal models by directly injecting murine pancreatic cancer KPPC-luc cells ($5\times10^6$) into pancreas of immunocompetent (C57BL/6J) mice. All mice were divided into two groups and treated with IgG isotype antibody as control, or mAb clone R4-4 (5 mg/kg) by intravenous (i.v.) injection via tail-vein at indicated time points (Day 3, Day 7, Day 10, and Day 14). Mice were sacrificed to verify tumor information on day 28. Notably, we observed significant reduction of tumor weight in R4-4 treated group without apparently body weight change as compared to IgG group (FIG. 10C, and FIG. 10D). As for tumor infiltrating immune profile, flow cytometry analysis showed that R4-4 decreased Treg ($CD45^+$, $Foxp3^+$) populations, M2-like TAMs ($CD206^+$), but increased the M1/M2 ratio in KPPC-luc-bearing C57BL/6J mice (FIG. 10E). Data was presented as means±S.D. P values refer to two-tailed Student's t test. * $P<0.05$, ** $P<0.01$.

Fully human mAb R4-54 mono-treatment exert anti-tumor and TME ameliorating effects in humanized mice model in vivo.

Figure 11A:
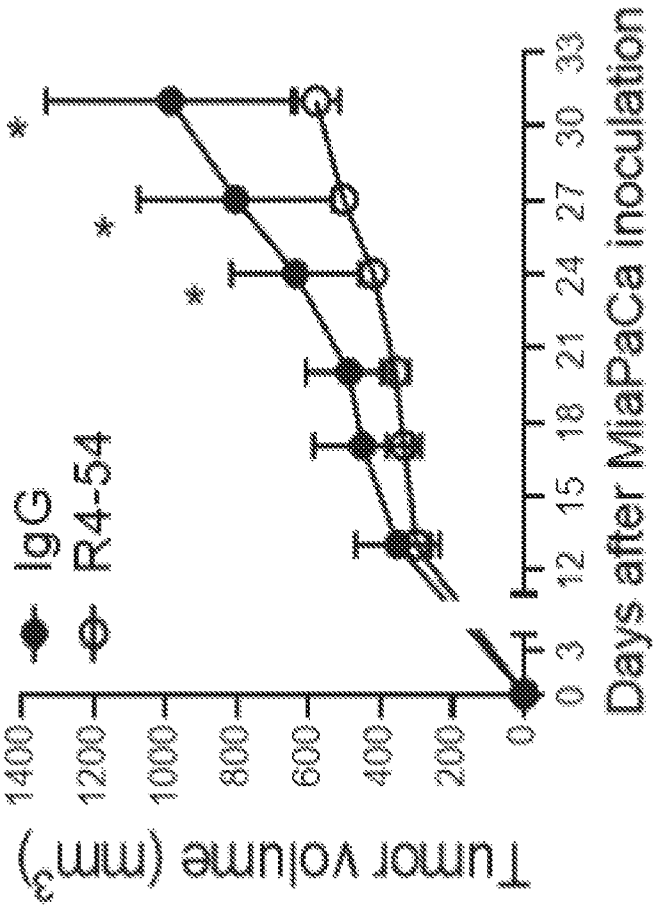
FIGS. 11A to 11D show that fully human mAbs clone R4-54 shows anti-cancer effect in human pancreatic cancer MiaPaCa-bearing hHSC-HIS mouse model.
Figure 11B:
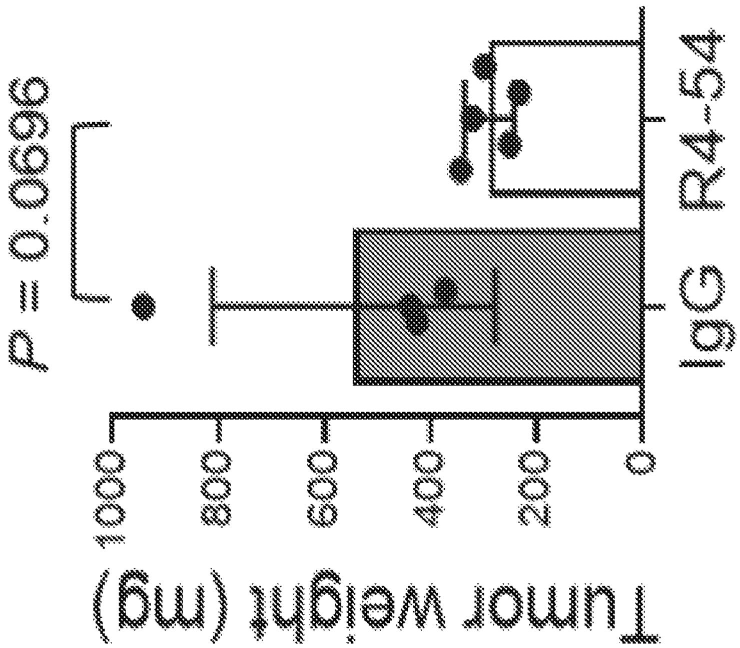
Figure 11C:
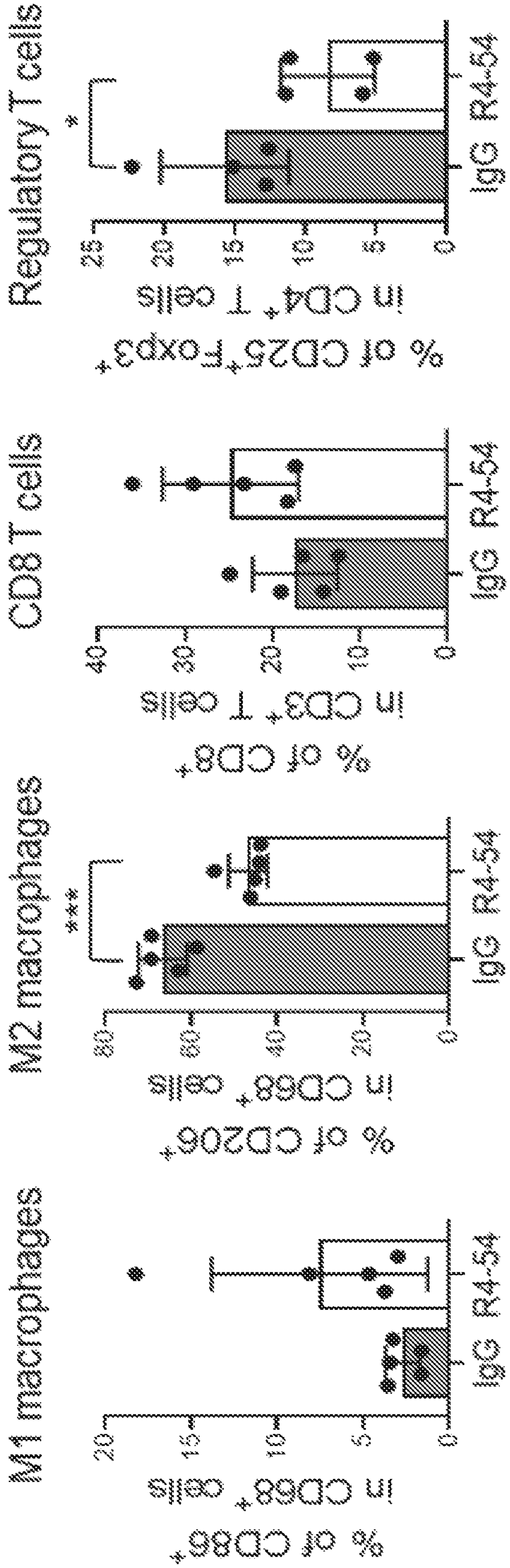
Figure 11D:
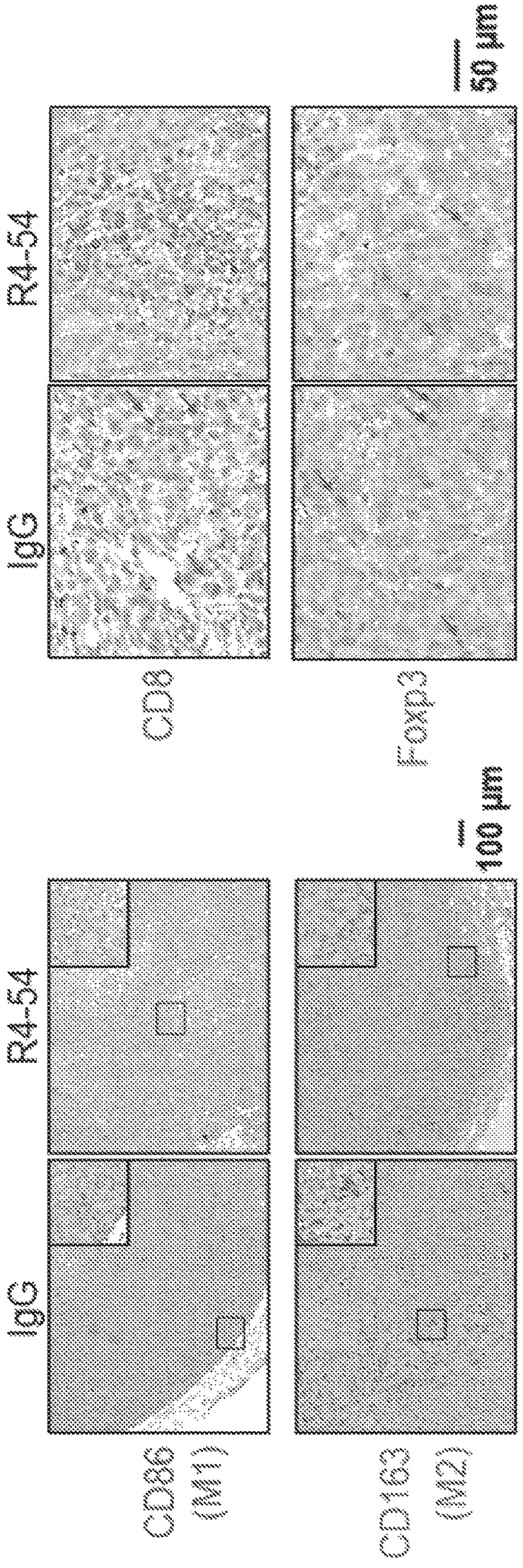
Figure 12A:
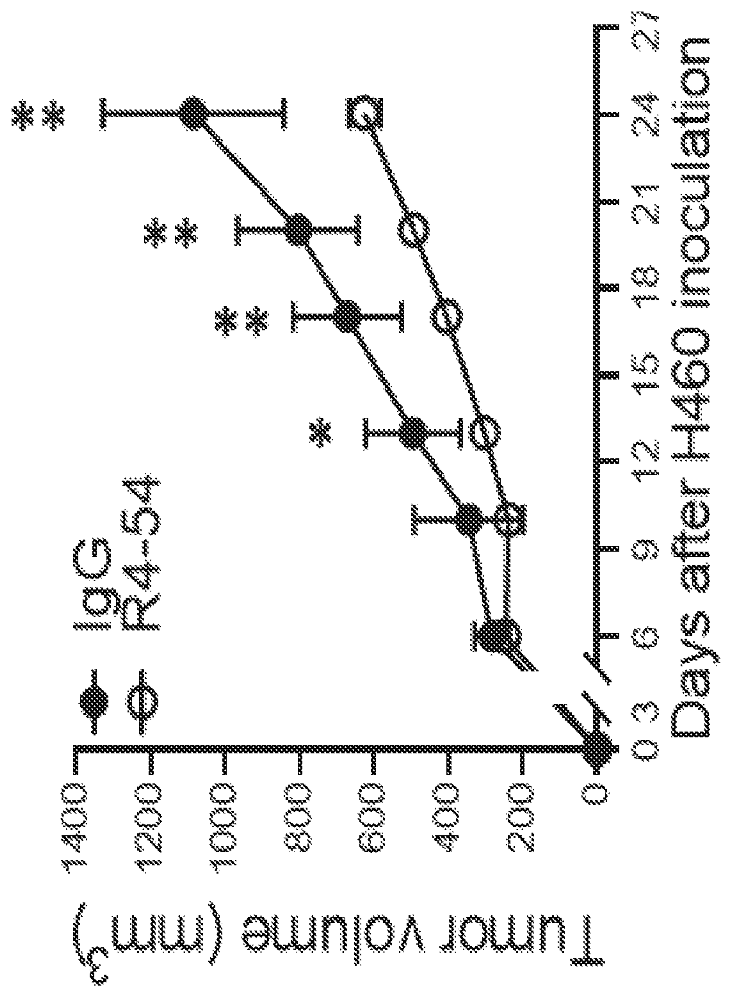
FIGS. 12A to 12D show that fully human mAbs clone R4-54 showed anti-cancer effect in human lung cancer H460-bearing hHSC-HIS mouse model.
Figure 12B:
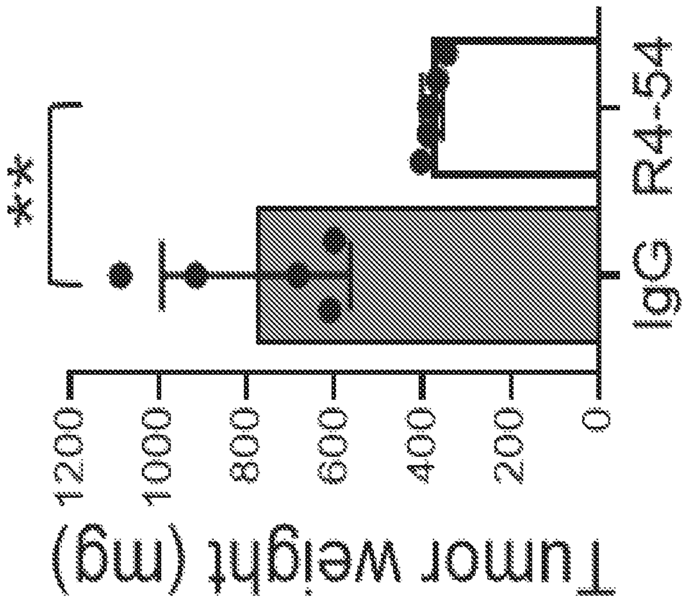
Figure 12C:
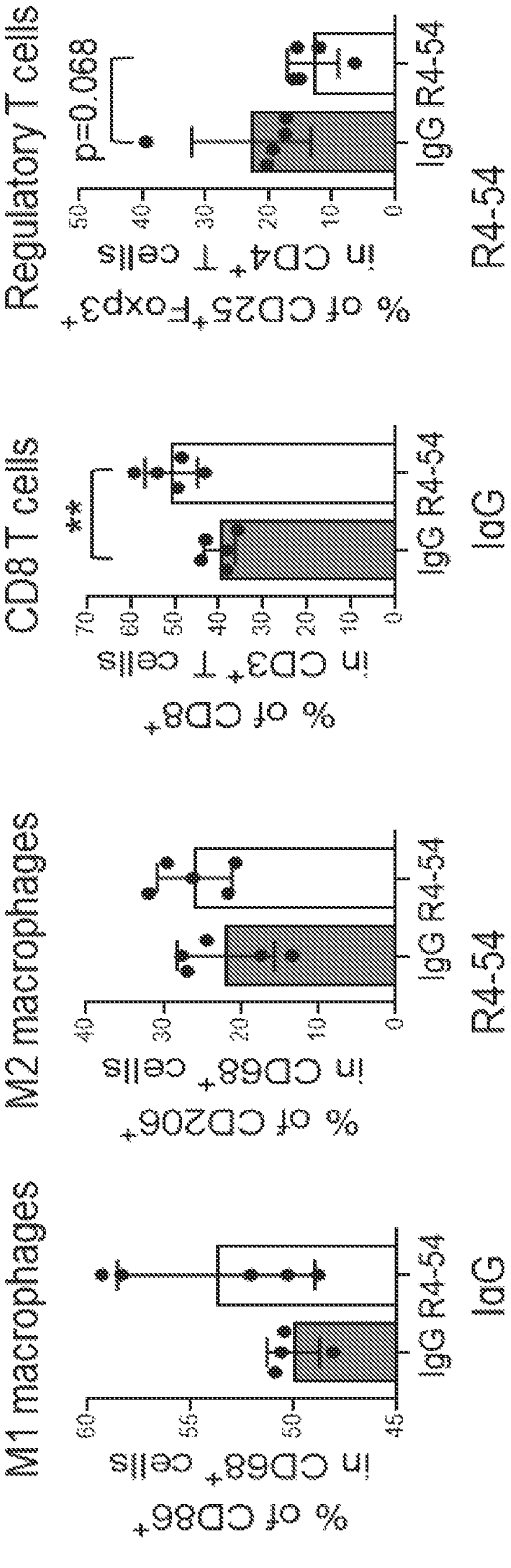
Figure 12D:
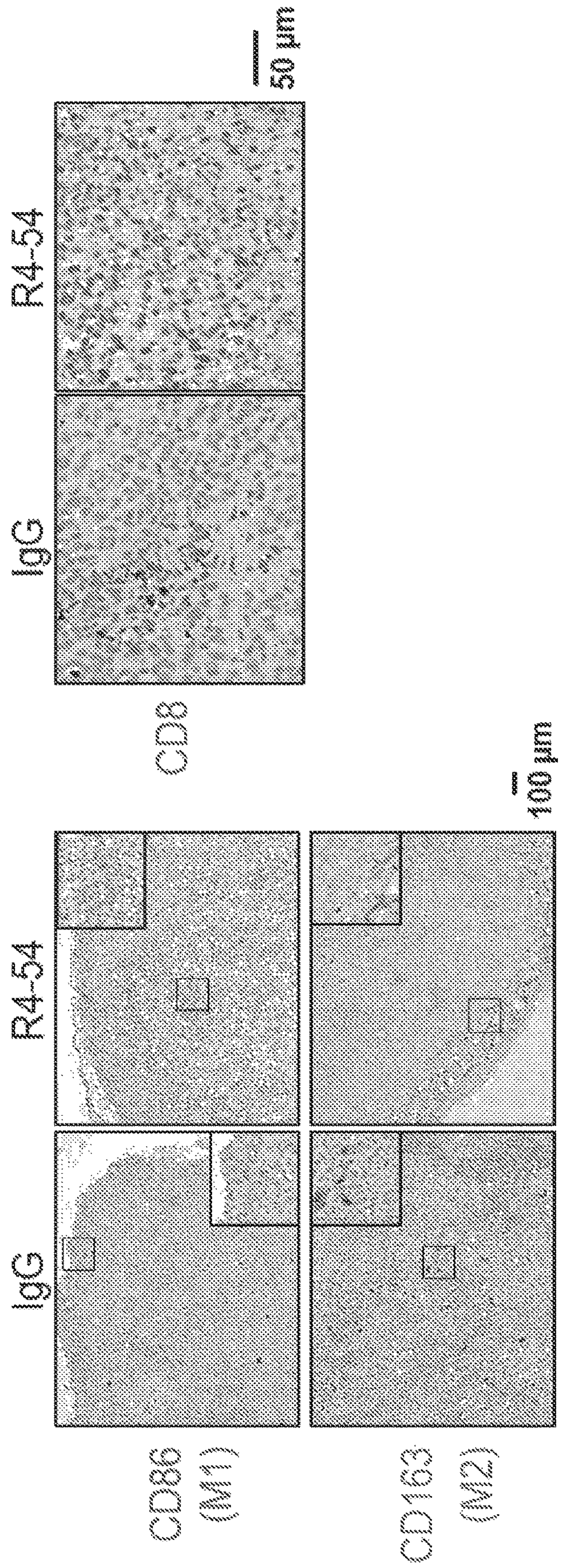
Figure 12E:
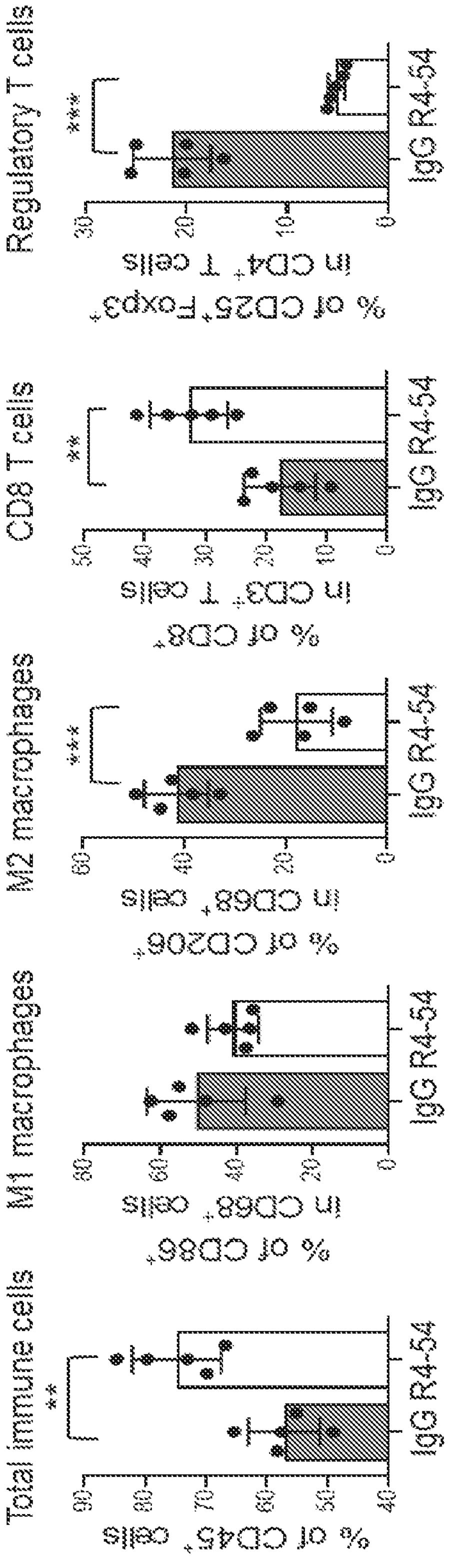
FIGS. 12E and 12F show that Fully human mAbs modulated immune cells toward an immunostimulatory state.
Figure 12F:
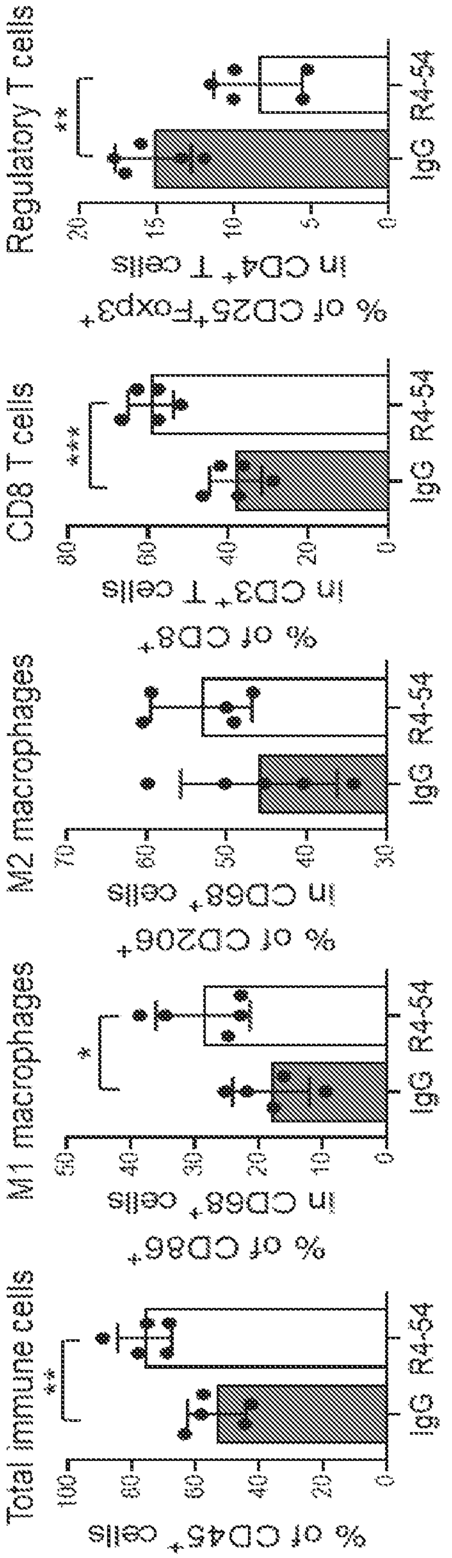

Having demonstrated effective CHI3L1 blockade in C57BL/6J immunocompetent mice, we further investigated how fully human monoclonal neutralizing antibody modulated human immune system. We used the advanced severe immunodeficiency (ASID) mice those were implanted with human CD45+ hematopoietic stem cells (HSCs). MiaPaCa-2 and H460 cells were then subcutaneously injected into hHSC reconstituted ASID mice to evaluate the anti-tumor effects of CHI3L1 mAb clone R4-54 on lung and pancreatic cell lines in vivo. IgG isotype or mAb clone R4-54 (5 mg/kg) was given by tail-vein injection every five days, starting on day 14 in MiaPaCa-2 and day 6 in H460-bearing hHSC mice when the tumors reached 300 $mm^3$ in size mimicking the clinical situation of late tumor diagnosis, and mice were sacrificed on day 32 in MiaPaCa-2-bearing hHSC mice and day 27 in H460-bearing hHSC mice. mAb clone R4-54 significantly delayed the growth of MiaPaCa-2 and H460 subcutaneous xenografts (FIG. 11A, FIG. 11B, FIGS. 12A, and 12B). Tumor and peripheral blood were also harvest for further immune cell population examinations. Flow cytometry analysis revealed that mAb clone R4-54 increased the percentages of M1 macrophages and CD8+ T cells ($CD8^+$, $CD3^+$) while M2-like TAM and Treg populations were decreased in tumor-infiltrating immune cells of MiaPaCa-2 and H460-bearing hHSC-HIS mice models (FIG. 11C and FIG. 12C). Consistently, intratumoral M2 macrophages were accumulated in IgG group, while M1 to M2 ratio and CD8 T cells were both increased in intratumoral regions upon R4-54 treatment in MiaPaCa-2/H460-bearing hHSC-HIS mice models, based on immunohistochemical staining using additional markers CD86 and CD163 (FIG. 11D and FIG. 12D). In addition, peripheral blood samples of two tumor-bearing hHSC-HIS mice models were collected for analysis of immune cell populations. Although the populations of M1 and M2 macrophages were not so consistently affected, the increased CD8+ T cells and decreased Tregs were significantly found in mAb clone R4-54 treated groups (FIG. 12E and FIG. 12F). Together, these data revealed that mAb clone R4-54 not only regulates the phenotype of tumor-infiltrated immune cells in TME but overall population of immune cells in peripheral blood, shifting to an anti-tumor immune environment. Data was presented as means±S.D. P values refer to two-tailed Student's t test. * P<0.05,  P<0.01, * P<0.001.

Fully human mAbs do not show apparent toxicity in treated mice.

Figure 13A:
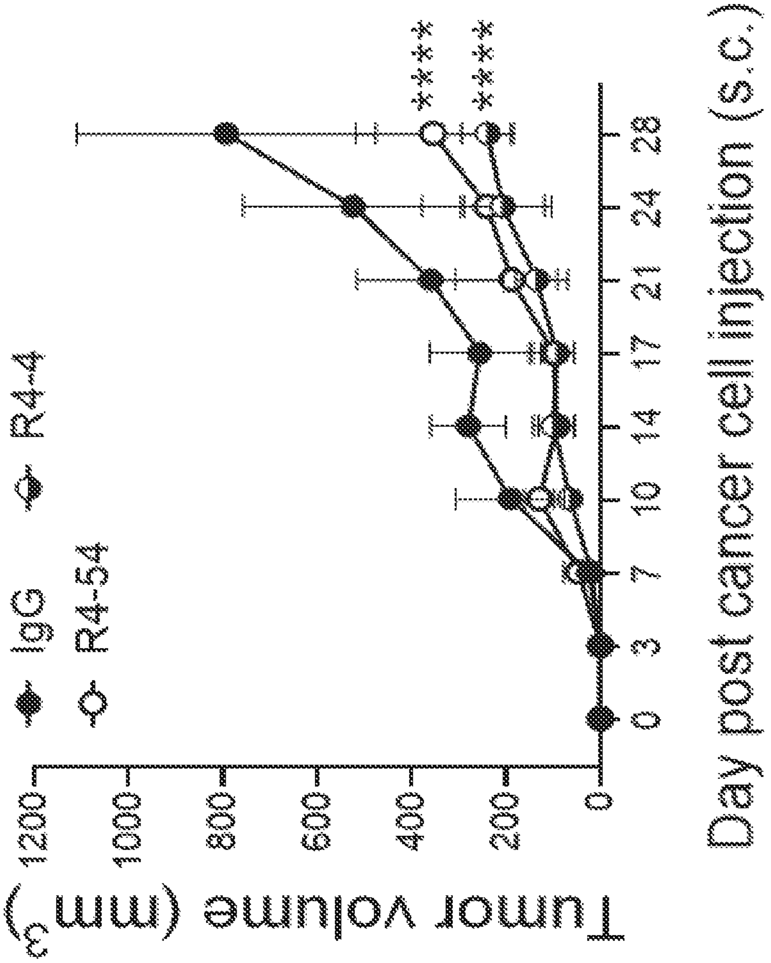
FIGS. 13A to 13E show that fully human mAbs clone R4-4 and R4-54 show anti-cancer effect in human pancreatic cancer MiaPaCa xenograft SCID mouse model.
Figure 13B:
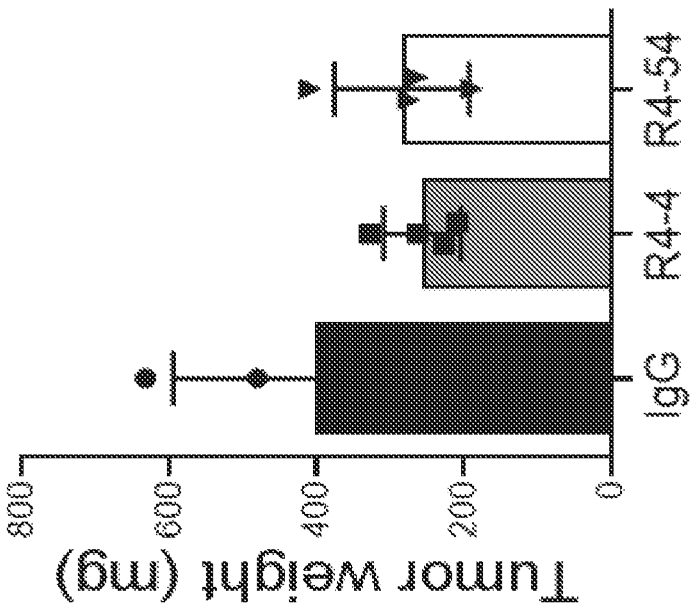
Figure 13C:
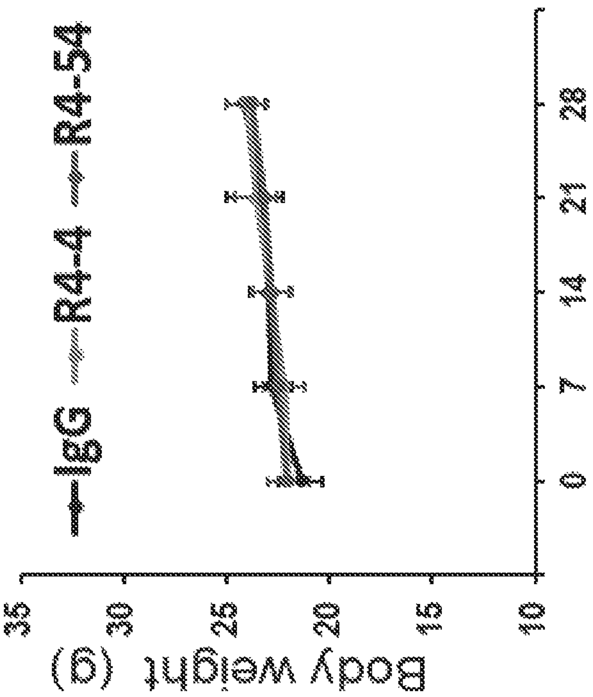
Figure 13D:
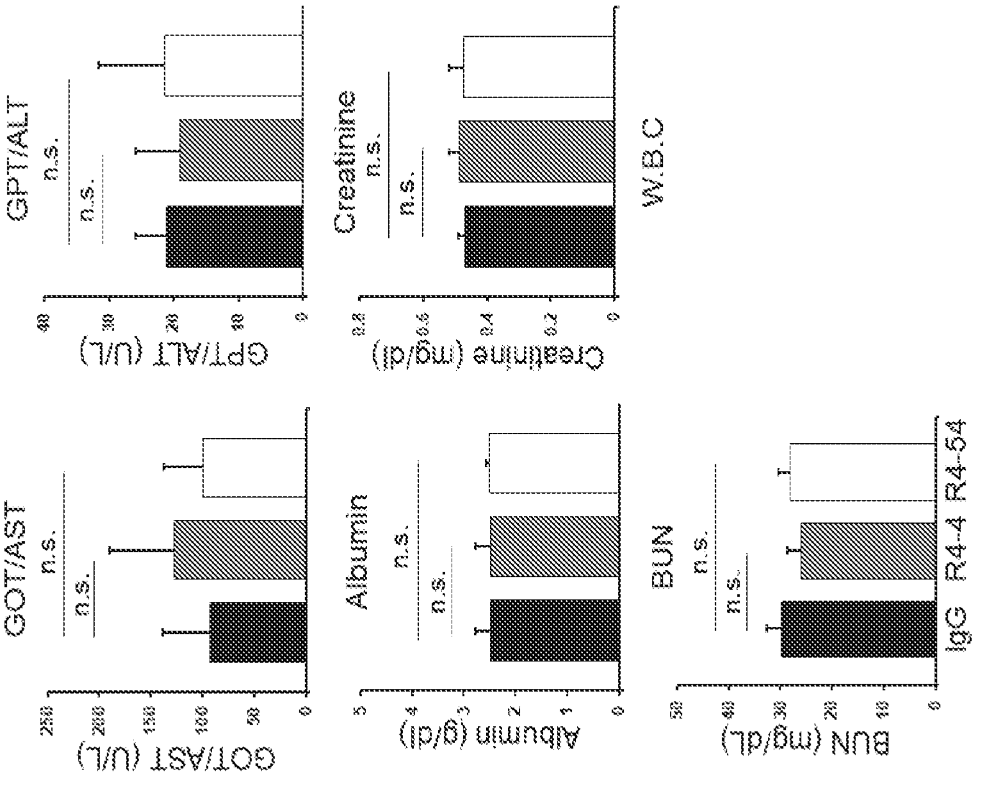
Figure 13E:
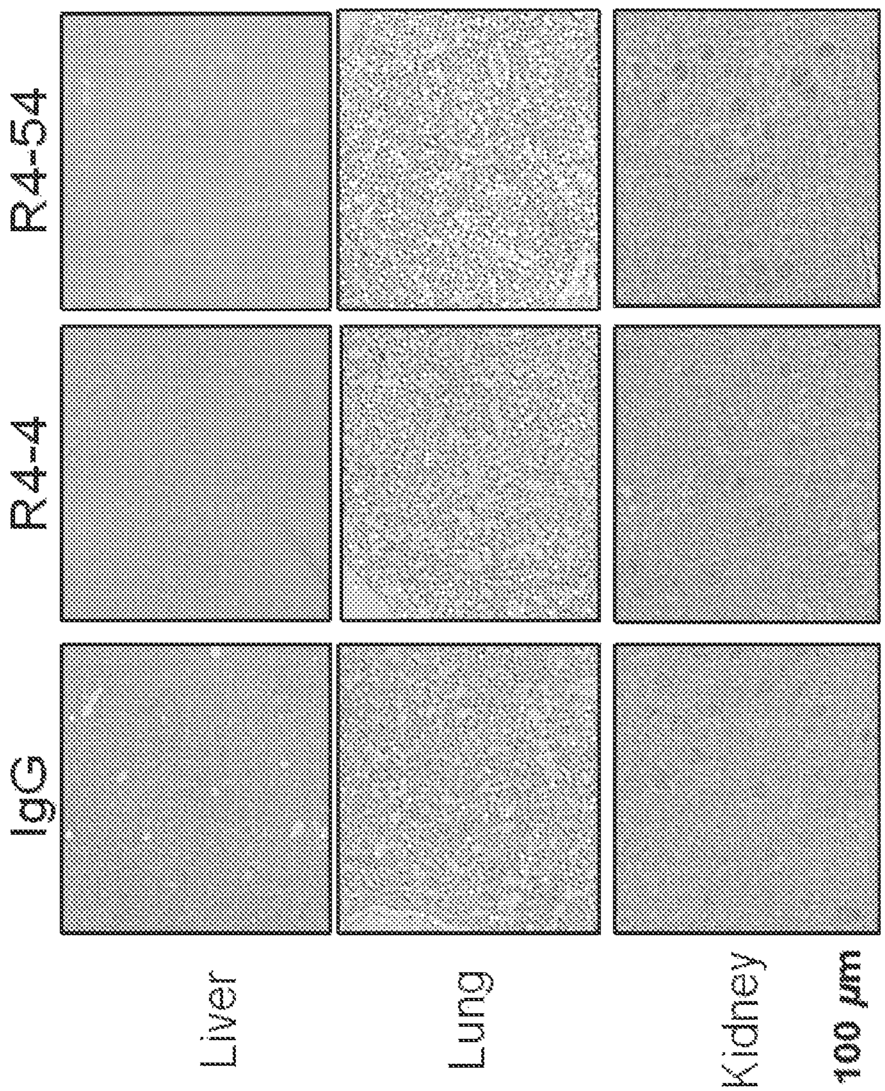

Next, we examined whether our mAb clones R4-4 and R4-54 exert any toxicity in vivo. We performed a xenograft model by subcutaneously implanting MiaPaCa-2 cells to NOD-SCID mice. The mice were i.v. injected with IgG isotype, mAb clone R4-4, or clone R4-54 (5 mg/kg) once a week starting from day 7 to day 21, that is, day 7, day 14, and day 21, and mice were sacrificed on day 28. Both R4-4 and R4-54 treatment significantly delayed the growth of MiaPaCa-2 subcutaneous xenografts (FIG. 13A and FIG. 13B). To evaluate the potential safety of our developed mAbs, we examined body weight, serum biochemical markers and histology sections of three major organs of tumor-bearing mice. There was no significant change in mice body weight between IgG control and R4-4 or R4-54 groups (FIG. 13C). No obvious difference was seen in the level of glutamate oxaloacetate transaminase (GOT), glutamate pyruvate transaminase (GPT), blood urea nitrogen (BUN), albumin and creatinine between IgG control and R4-4 or R4-54 treatment (FIG. 13D). Moreover, histology examination of three major organs including liver, lung and kidney revealed no significant adverse effects upon mAbs treatment (FIG. 13E). Collectively, these results suggested that our developed monoclonal CHI3L1 neutralizing antibodies exerted anti-tumor effects through directly regulating tumor growth and modulating an immunostimulatory tumor microenvironment without any significant side effect. Scale bar 100 μm. P values were determined by one-way ANOVA. * P<0.05,  P<0.01, * P<0.001, **** P<0.0001.

Fully human mAbs and chemotherapy combination treatment exerts synergistic anti-tumor and TME ameliorating effects in vivo.

Figure 14A:
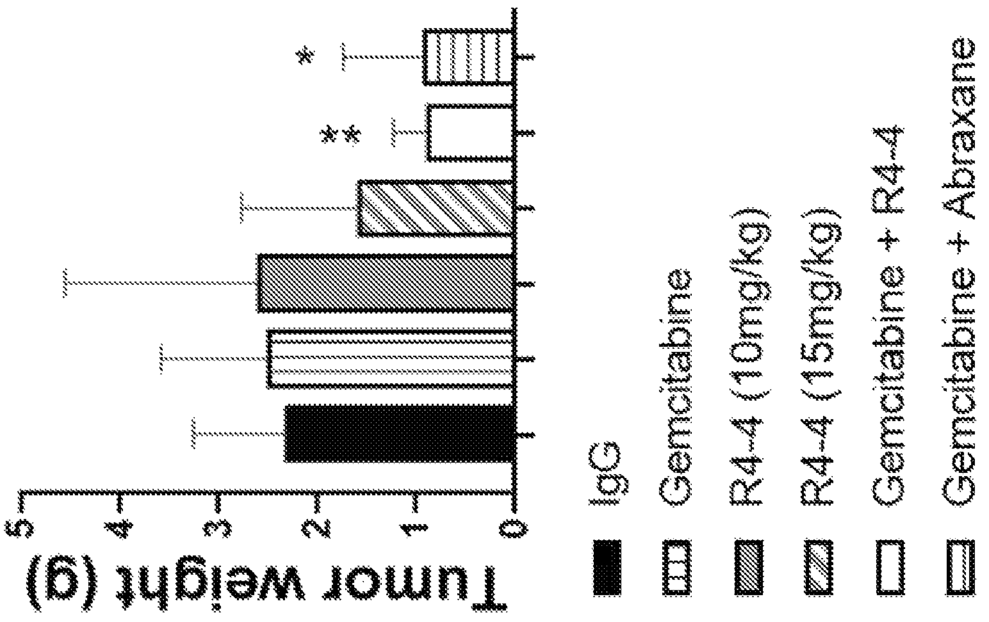
FIGS. 14A to 14F show that synergistic anti-tumor effects of fully human mAb clone R4-4 and chemotherapy combination treatment in KPPC-luc orthotopic C57BL/6J mice model.
Figure 14B:
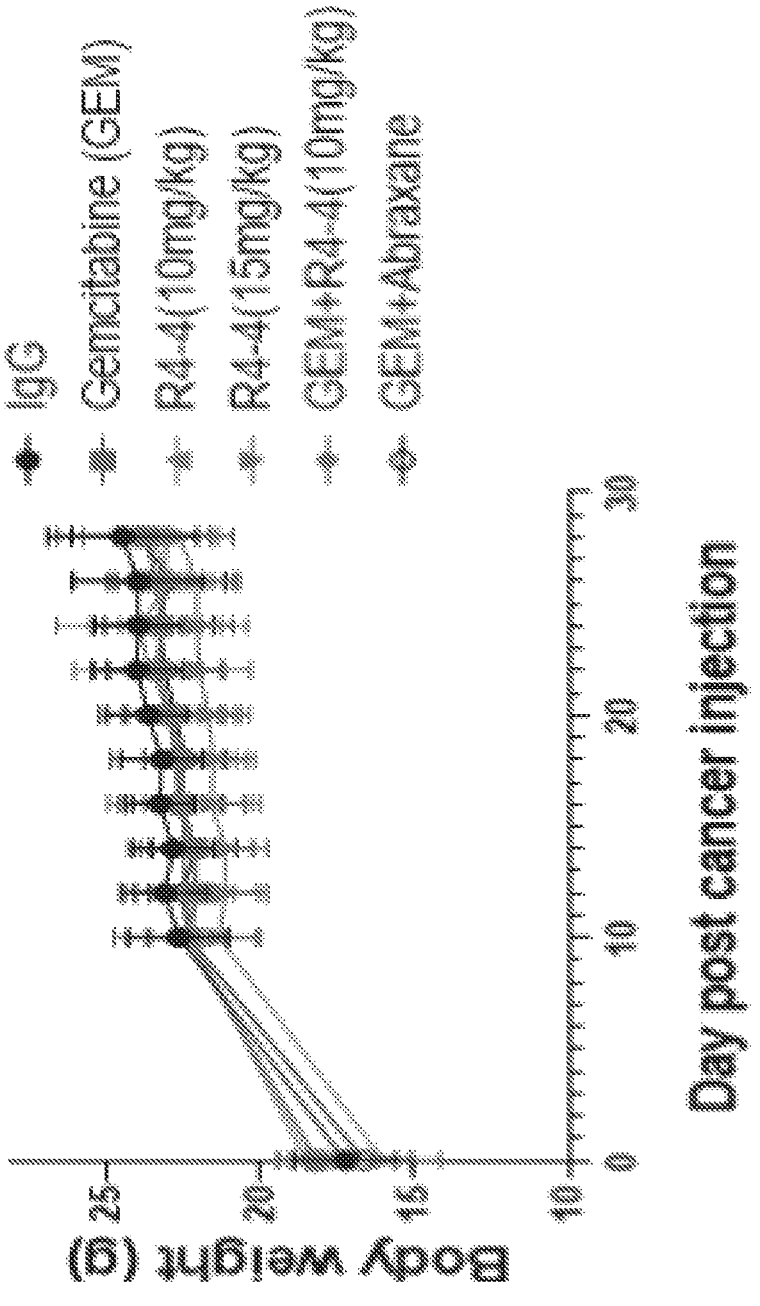
Figure 14C:
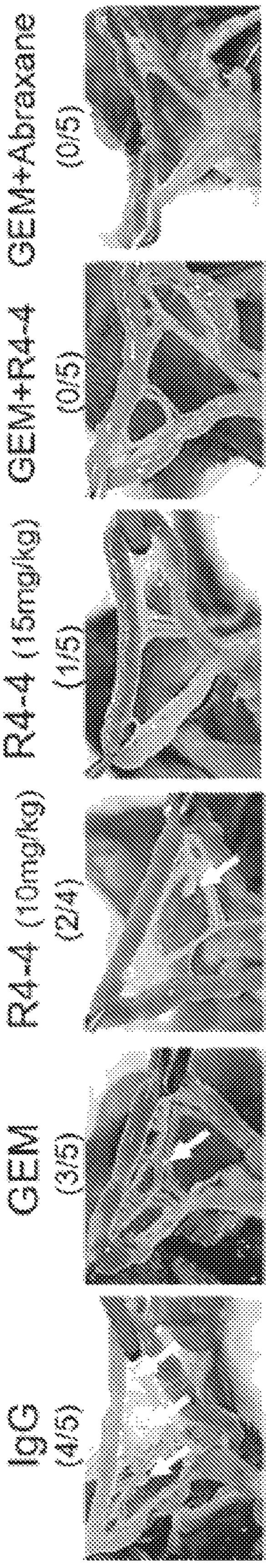
Figure 14D:
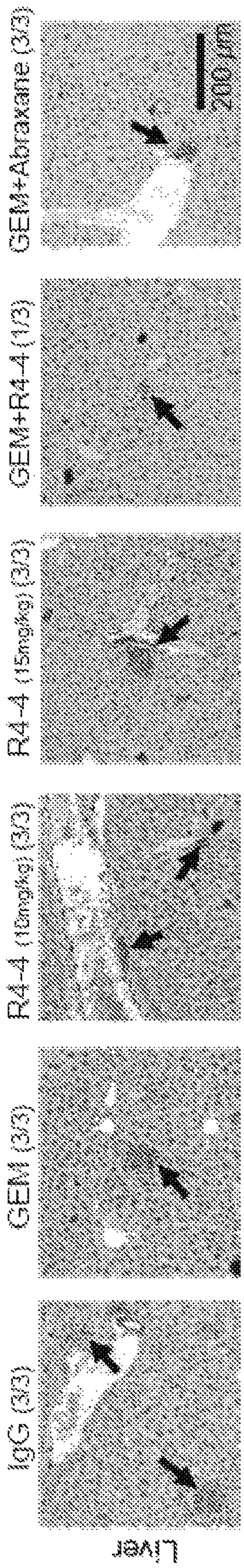
Figure 14E:
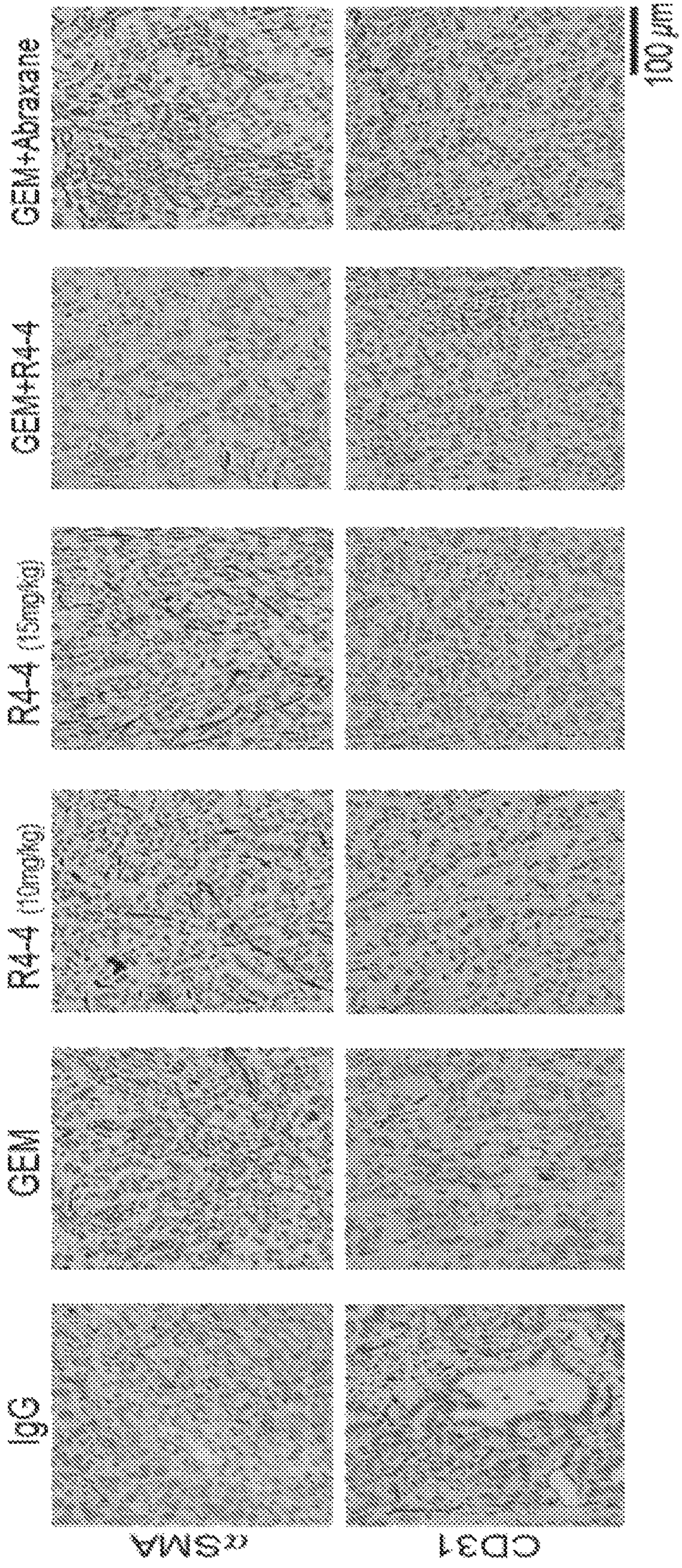
Figure 14F:
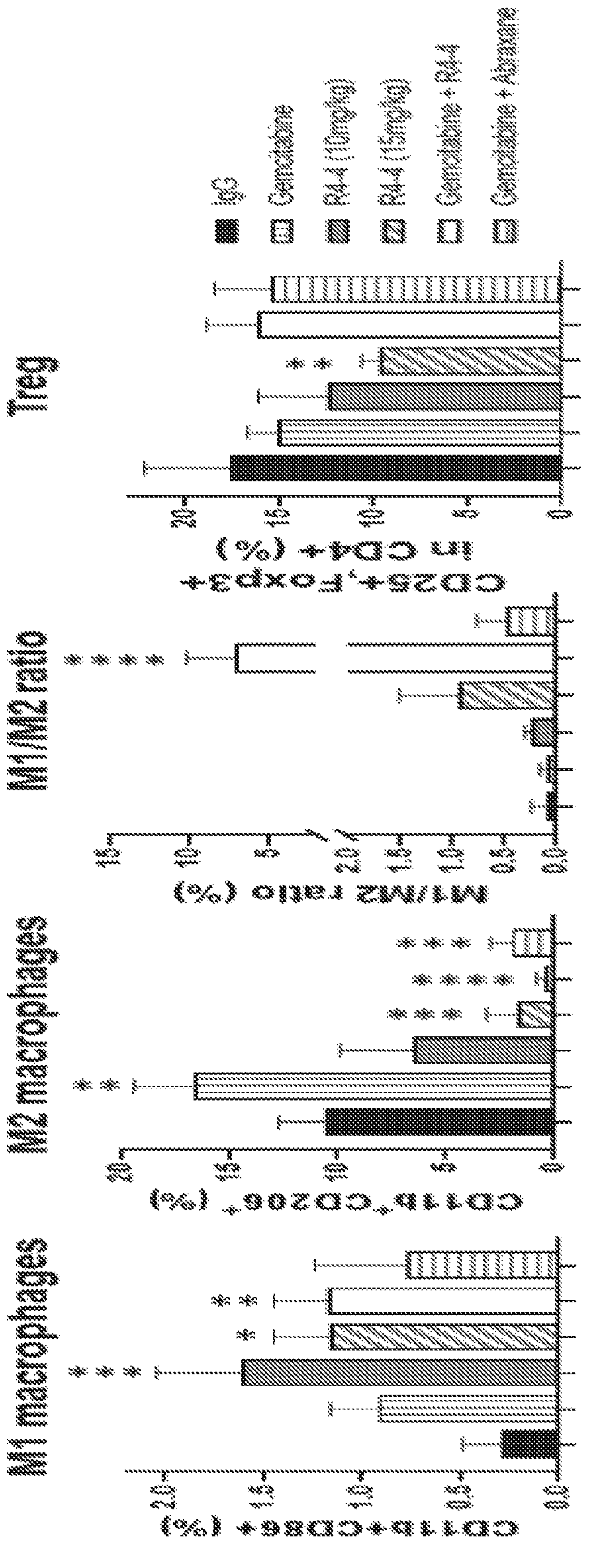

To come up with the most effective therapeutic strategy, we sought to test whether combined treatment of the first-line chemotherapy gemcitabine and mAb in pancreatic tumor bearing C57BL/6J mice. Murine KPPC-luc cells were orthotopically injected to the pancreas of C57BL/6J, and treatment started on day 14 post-operation. The mAbs clone R4-4 (10 mg/kg or 15 mg/kg), gemcitabine (GEM, 25 mg/kg), Abraxane (2.5 mg/kg) or control IgG Ab were given by i.p. at indicated time point (day 14, day 20, and day 25), and mice were sacrificed on day 29. KPPC-luc bearing mice was further divided into six groups, including IgG isotype, gemcitabine (25 mg/kg), R4-4 (10 or 15 mg/kg), gemcitabine (25 mg/kg) plus R4-4 (10 mg/kg), or gemcitabine (25 mg/kg) plus Abraxane (2.5 mg/kg). The last group, GEM plus Abraxane, is the clinically use combination chemotherapy used for pancreatic cancer treatment. Luciferase activity of tumor cells and tumor weight measurement showed obvious restricted tumor growth in GEM plus R4-4 which was comparable to the GEM plus Abraxane treated groups (FIG. 14A, IgG: 2.322 g, GEM: 2.51 g, R4-4 10 mg/kg: 2.61 g, R4-4 15 mg/kg: 1.74, GEM+R4-4:0.902 g, GEM+Abraxane: 0.932 g). All treatment groups did not cause significant weight loss (FIG. 14B). Moreover, mesentery and liver metastasis were reduced in GEM plus R4-4 treated groups (FIG. 14C and FIG. 14D), arrow indicated metastatic tumor nodules, and (4/5) means that 4 out of 5 have metastasis, etc. Tumor fibrosis indicated by αSMA increased in GEM group and GEM plus Abraxane group while reduced in GEM plus R4-4 (10 mg/kg) treated group (FIG. 14E, upper). Angiogenesis level which indicated by CD31 was largely reduced in all treated groups (FIG. 14E, lower). For the tumor-infiltrating immune profile, flow cytometry analysis showed decreased M2-like TAMs ($CD206^+$, $CD11b^+$) increased M1-like TAMs ($CD86^+$, $CD11b^+$) and M1/M2 ratio in both R4-4 monotreatment or combination treatment groups. Although the effect on lymphocyte was not as impressive as macrophages, we found significant decrease of Treg (CD4+, CD25+, Foxp3+) in R4-4 (15 mg/kg) treated group (FIG. 14F).

Figure 15A:
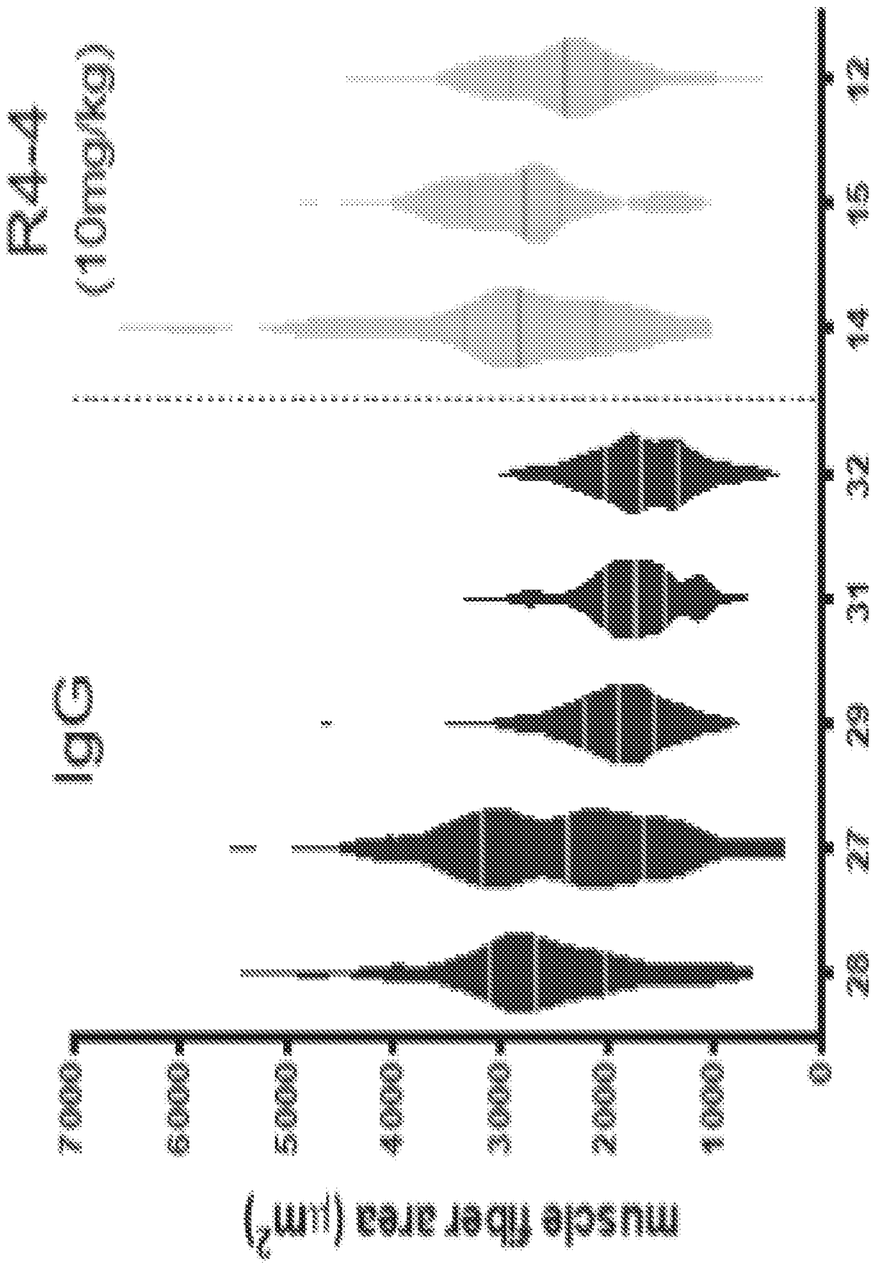
FIGS. 15A to 15D show that anti-CHI3L1 mAbs potentially exerted anti-cachexia effects in KPPC-luc orthotopic C57BL/6J mice model.
Figure 15B:
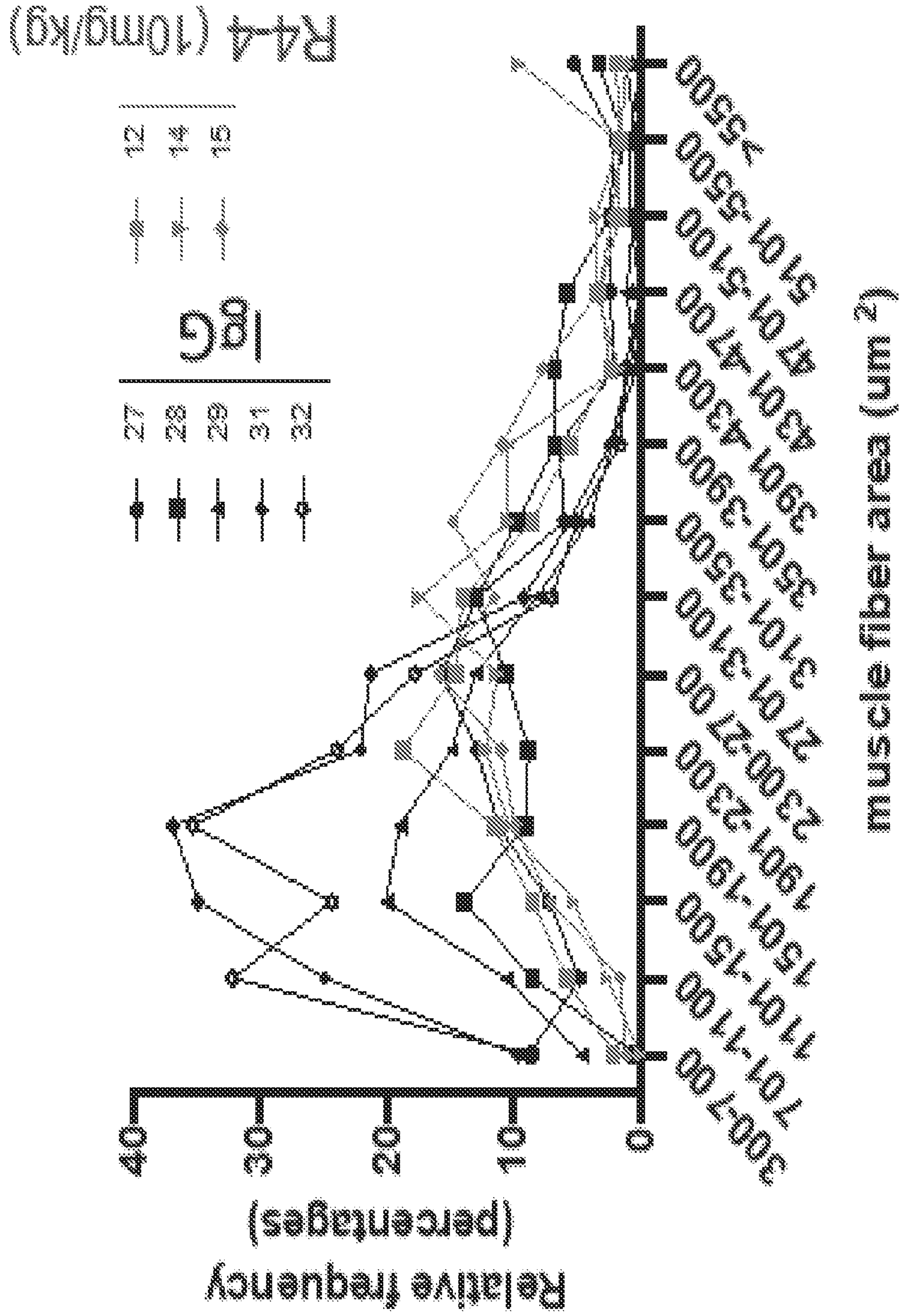
Figure 15C:
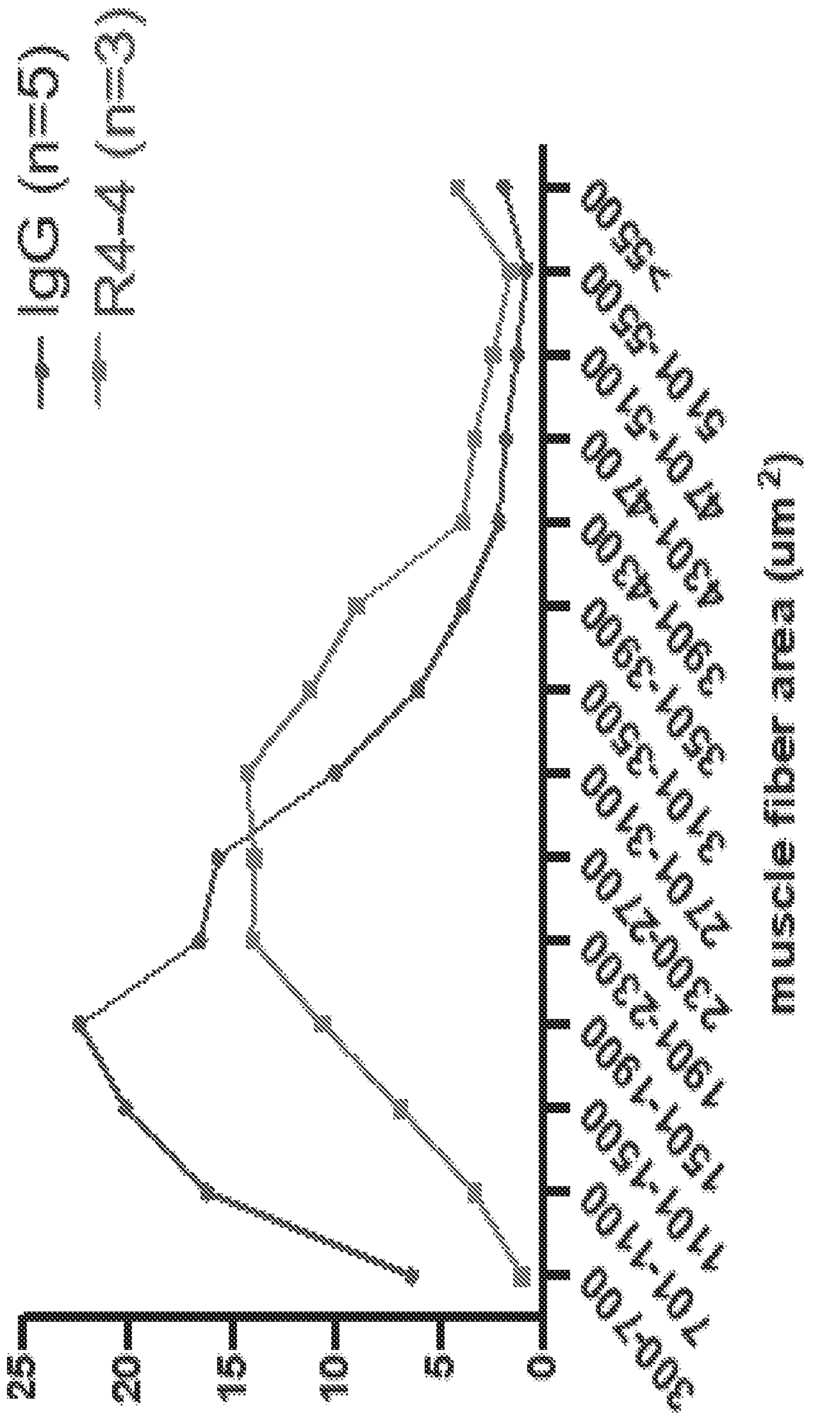
Figure 15D:
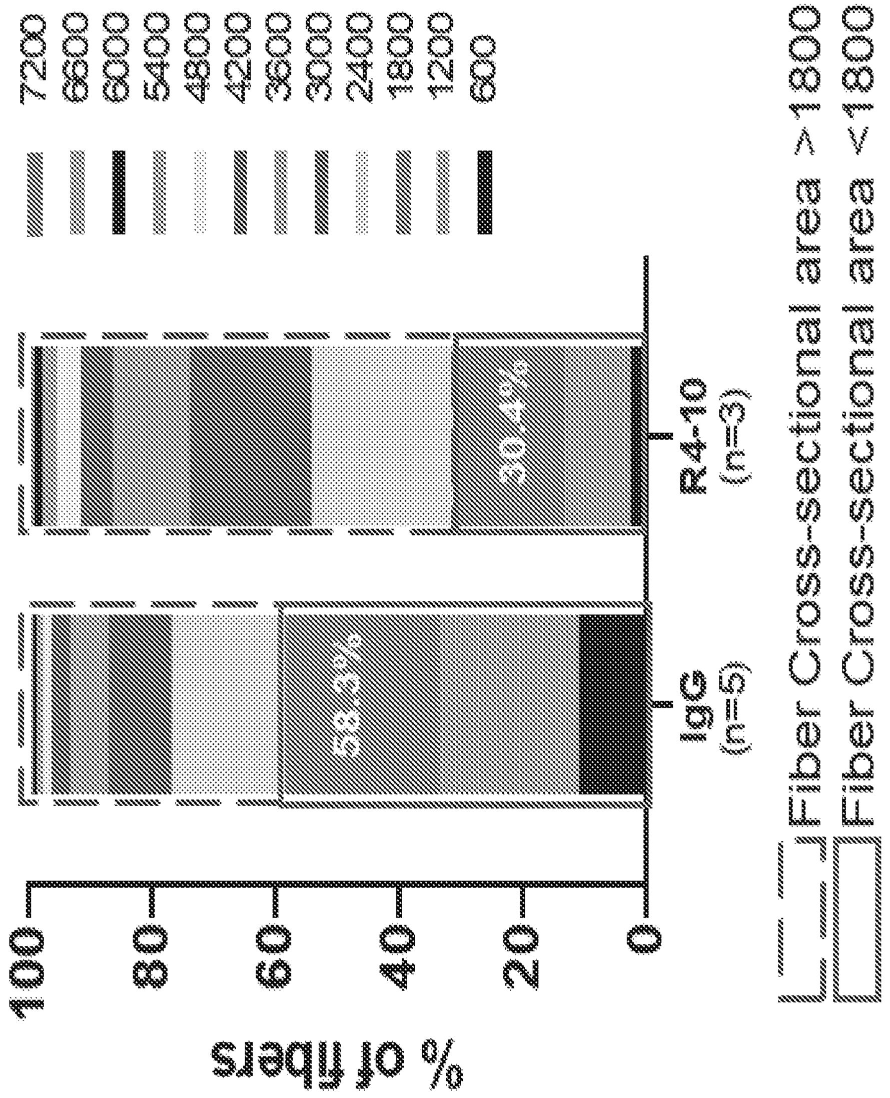
Figure 16A:
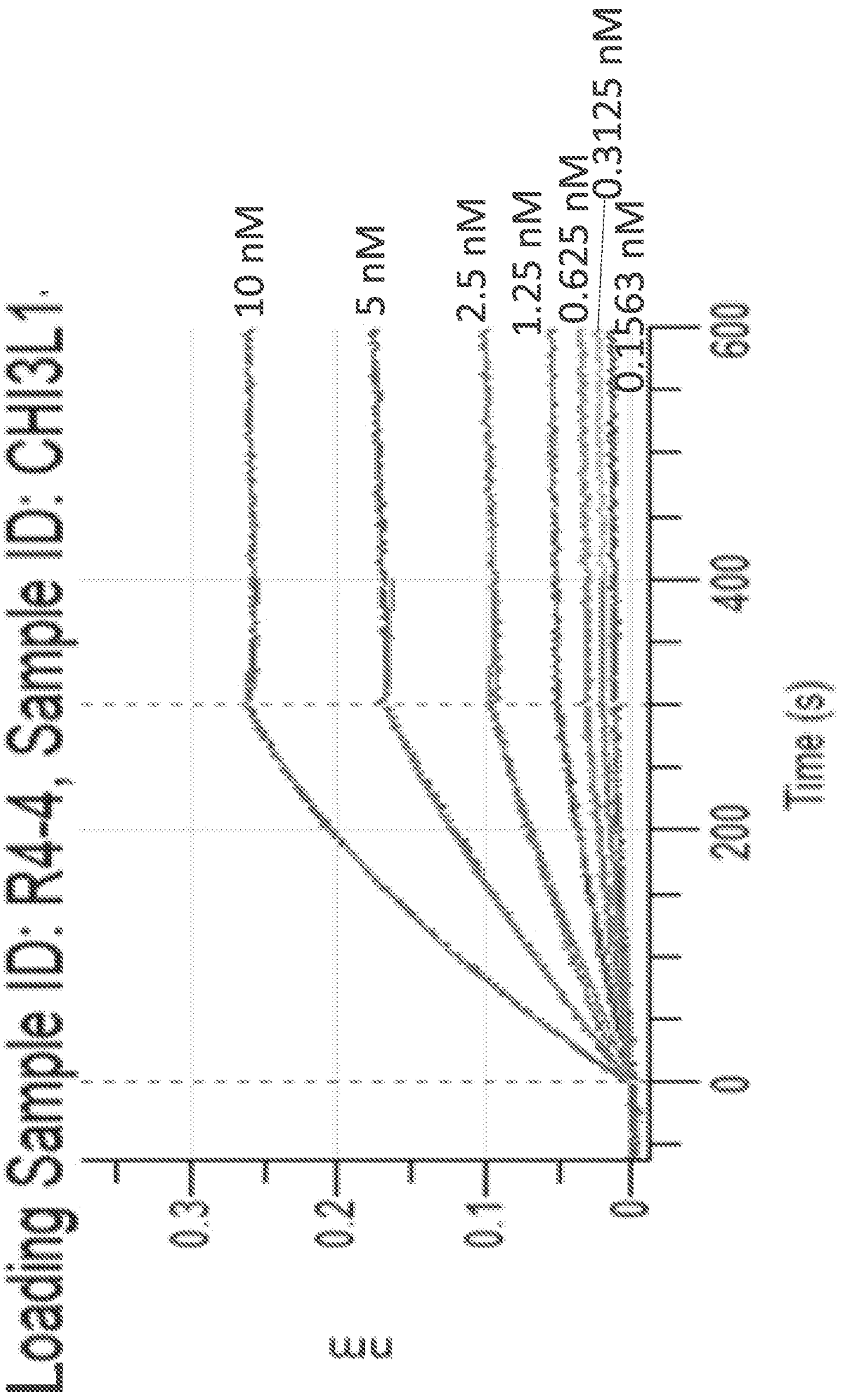
FIGS. 16A to 16D show binding kinetics of the R4-4, R4-54, 293R3-2, and 293R3-4 antibodies.
Figure 16B:
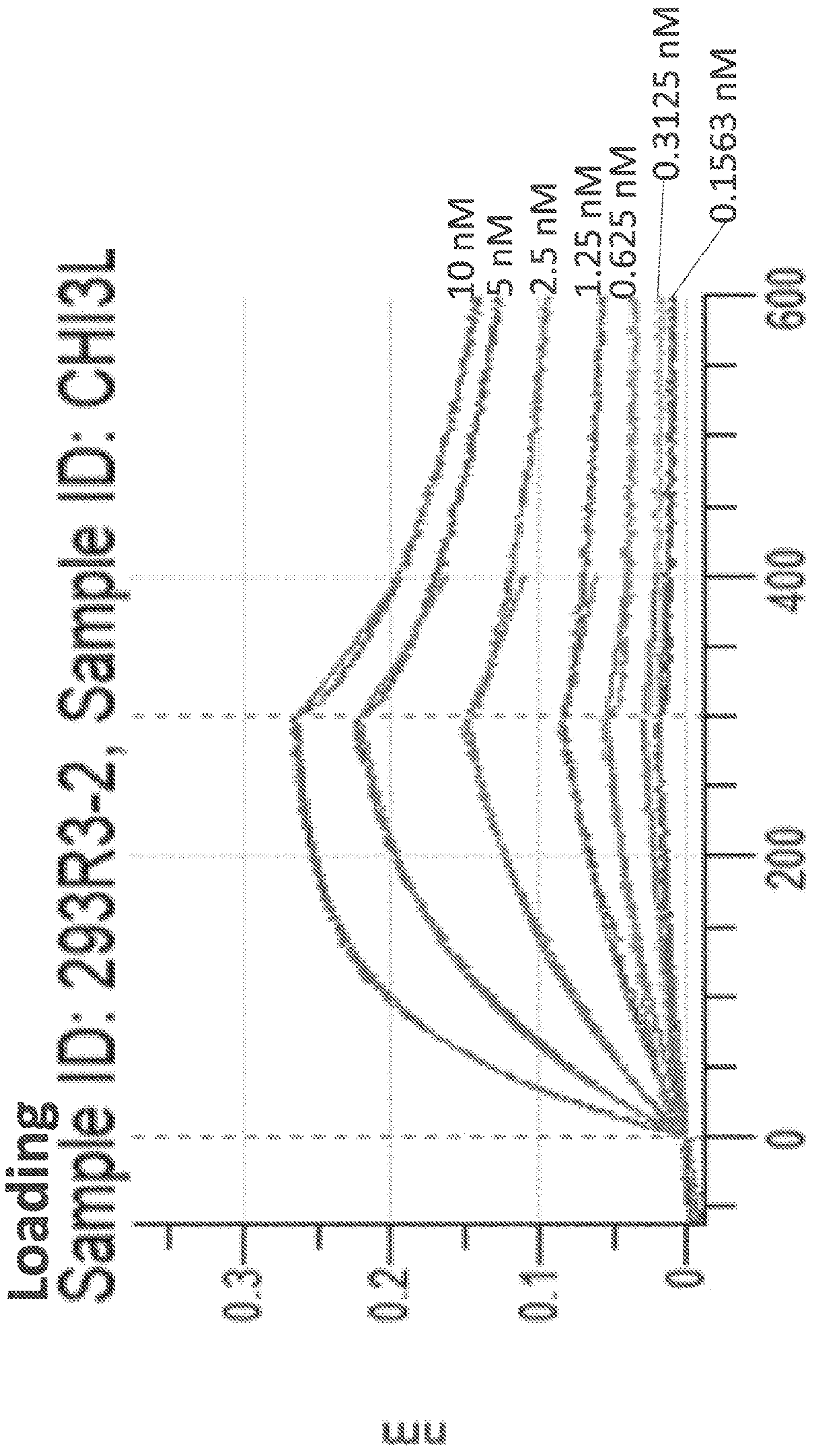
Figure 16C:
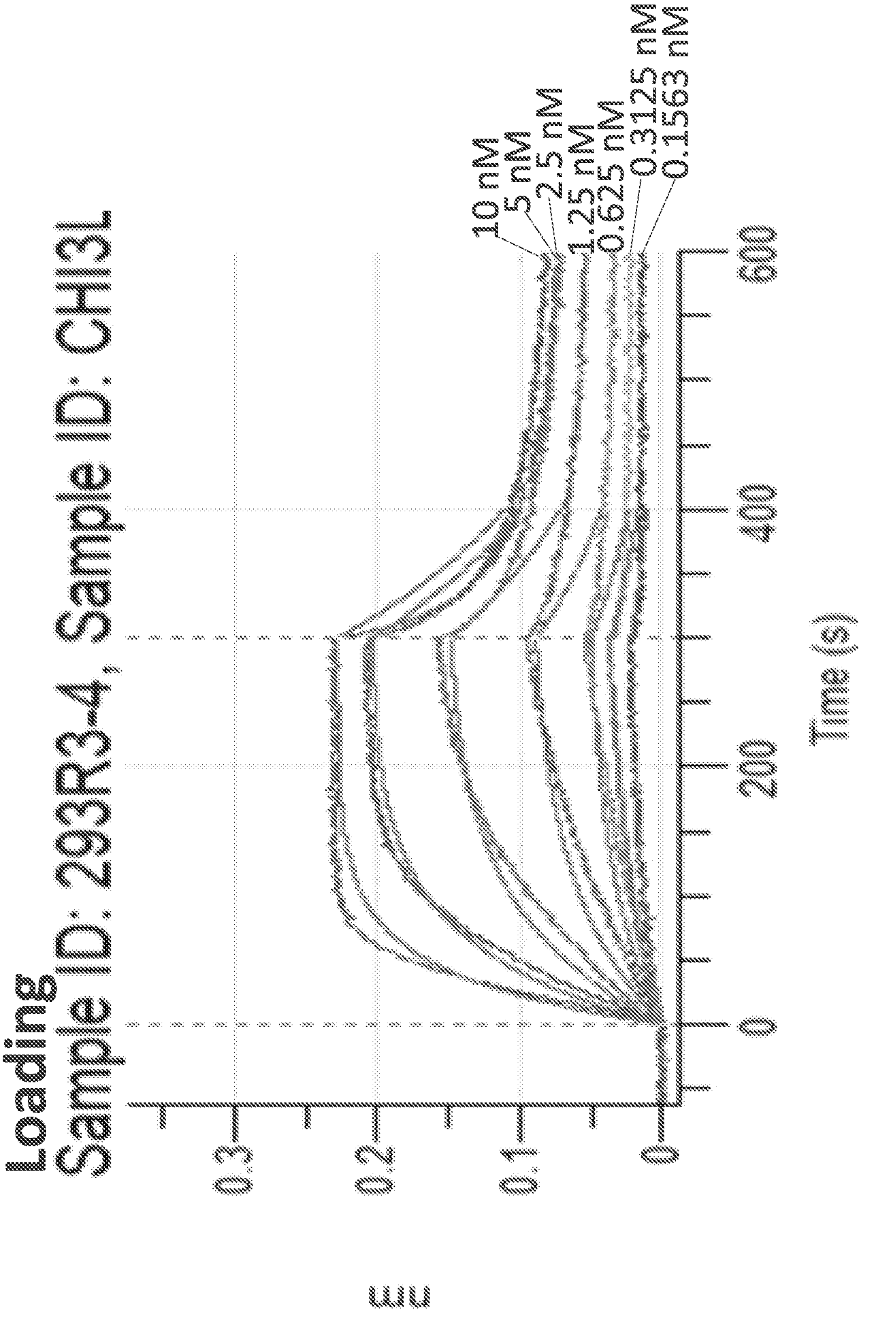
Figure 16D:
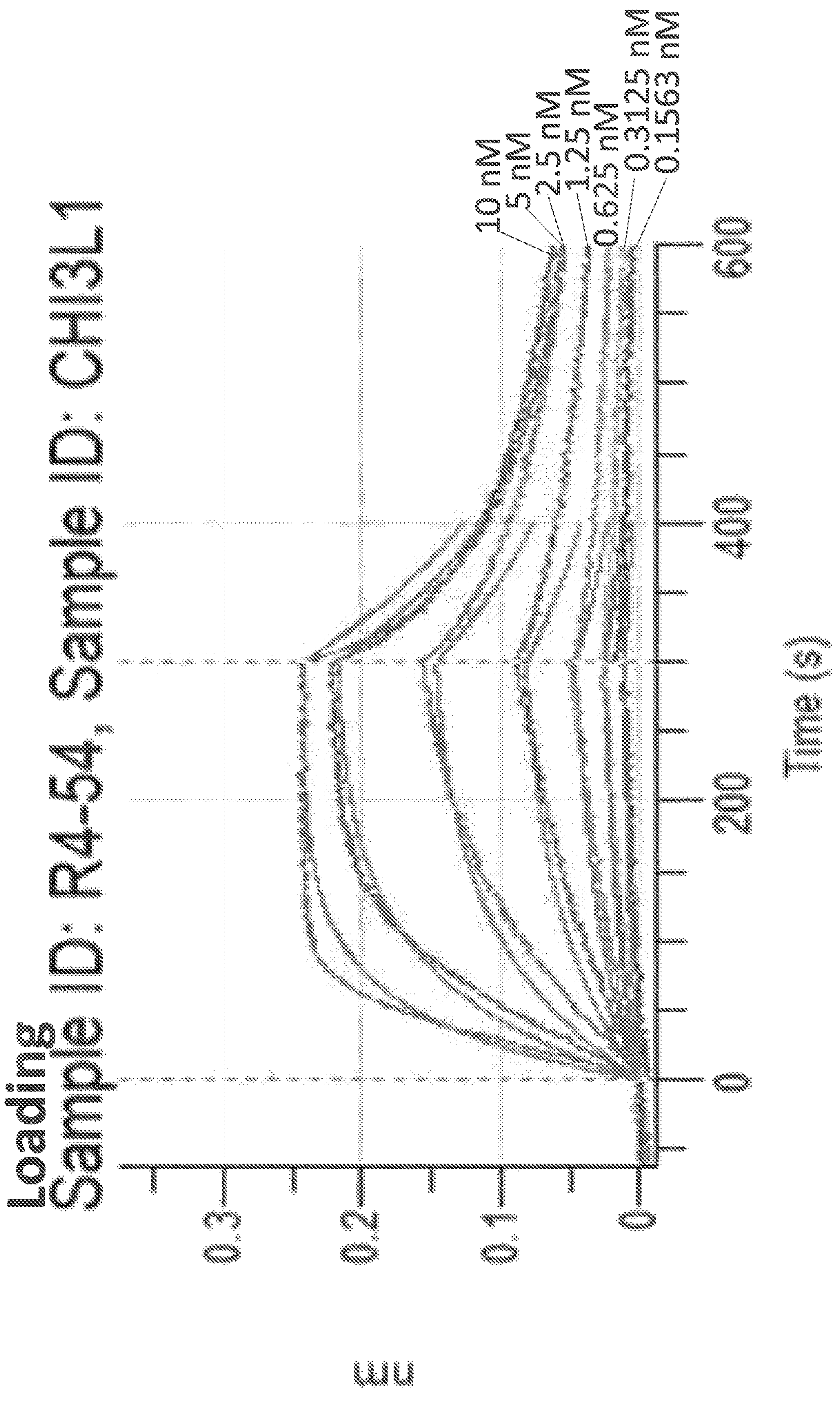

Since pancreatic patients often suffer from cachexia, the cancer-related muscle loss disorder (Henderson et al. 2018; Yoo et al. 2021), we further performed the mouse muscle fiber area analysis in IgG and R4-4 (10 mg/kg) groups. The muscle fiber area measurement, although were heterogeneous (FIG. 15A shows each relative frequency, and FIG. 15B shows mean frequency), showed larger muscle fiber area in R4-4 compared to IgG (FIG. 15C). The value of the cross-sectional cutoff area was set to 1800, representing severe muscle loss (FIG. 15D). An average of 58.3% of muscle fibers in the IgG control group was below the cut off value, while muscle loss was reduced in the R4-4 (10 mg/kg) treated group (30.4% of muscle fibers were below the cutoff value). The R4-4 treatment prevented muscle wasting by preserving the larger fibers (those greater than 1800% of fibers), indicating the anti-CHI3L1 mAbs potentially exert anti-cachexia effects.

ForteBio binding analysis between anti-CHI3L1 mAbs and rCHI3L1.

In addition to the functionality validation is important during the early stages of antibody discovery. It is also important to have an efficient and accurate way to assess the success or failure of a particular discovery effort. First, binding affinity to the target is a critical criterion for the success of the antibody. Second, epitopic coverage is also important during the very early stages of discovery, for without targeting the relevant epitope.

Here, four candidates as showed above were conducted for affinity determination by biolayer interferometry analysis (ForteBio, USA). Anti-CHI3L1 mAbs were loaded at 5 μg/mL on AHC (Anti-Human IgG Fc Capture, ForteBio, Cat #18-5060) for signal reach to approximate 0.5 nm. Sensors then were exposed to human CHI3L1 extracellular domain fused with flag and His tag recombinant protein, hCHI3L1/flag-His, solutions at 10 nM with 2 time serial dilution for 7 concentrations. Measurement were performed as follows: 1 min baseline in kinetic buffer, 5 minute association in 7 different concentrations hCHI3L1/flag-His and 5 minute dissociation into kinetic buffer. The kinetic parameters were calculated and produced by Octet Data Acquisition and Analysis Software. In this assay, the binding affinity of anti-CHI3L1 antibodies against recombinant hCHI3L1 fused with flag-His tag were around 1.13 E-09 M to 4.22E-09 M (FIG. 16A, FIG. 16B, FIG. 16C, FIG. 16D and Table 3). Although all mAbs have the similar affinity, R4-4 has different binding kinetics profile with slower on-rate (kon) and off-rate (koff) compare to other mAbs that indicates there has a different molecular interaction mechanism of R4-4 against CHI3L1.

TABLE 3

| No. | Analyte | Loading Sample ID | KD (M) | kon (1/Ms) | koff (1/s) | Full X^2 | Full R^2 |
|---|---|---|---|---|---|---|---|
| 1 | hCHI3L1 | R4-4 | 1.13E−09 | 3.13E+06 | 3.53E−04 | 0.0673 | 0.9990 |
| 2 | hCHI3L1 | 293R3-2 | 2.79E−09 | 1.08E+06 | 3.02E−03 | 0.1620 | 0.9981 |
| 3 | hCHI3L1 | 293R3-4 | 3.94E−09 | 1.83E+06 | 7.22E−03 | 1.2196 | 0.9832 |
| 4 | hCHI3L1 | R4-54 | 4.22E−09 | 1.54E+06 | 6.50E−03 | 1.1511 | 0.9868 |

Mapping/Binning of the epitopes of the four monoclonal antibodies.

In order to know the epitopic coverage for those four antibodies to increase the success of therapeutic CHI3L1 antibody development, epitope binning is used to characterize the binding site of mAbs to the corresponding antigen and summarized in the Table 4. In epitope binning, mAbs specific to the same target protein are tested pairwise against all mAbs in a set to assess whether they block one another's binding to a specific site of the antigen or not. The mAbs that block binding to the same epitope are "binned" together. mAbs within the same bin often function similarly, so epitope bins can narrow down the choices to fewer candidates for investigators to choose from. The in tandem epitope binning assay conducted on Octet Red96 comprised a five-step binding cycle; 1) a buffer baseline was established for 30 sec, 2) 100 nM hCHI3L1/flag-His was captured for 5 min, 3) 100 nM mAb array was loaded to saturate the captured antigen for 10 min, 4) 100 nM of the test mAb was bound for 5 min, and 5) the capture surfaces were regenerated for 30 sec. Anti-His surfaces were regenerated with 10 mM glycine pH 1.7. Raw data was processed using ForteBio's Data Analysis HT Software 11.1 and the antibody pairs were assessed for competitive binding. Additional binding by the second antibody indicates an unoccupied epitope (non-competitor, marked as *c in Table 4), while no binding indicates epitope blocking (competitor, marked as *b in Table 4) and self-competing antibodies were marked as *a in Table 4. Among four anti-CHI3L1 mAbs, there are two epitope clusters. R4-4 was identified as an exclusive epitope. R4-54, 293R3-2 and 293R3-4 had unidirectional blocking results which occur with disparate-affinity antibodies of closely adjacent or minimally overlapping epitopes.

TABLE 4

Epitope Binning Heat Map

| Ab# | CHI3L1 293R3-2 | CHI3L1 293R3-4 | CHI3L1 R4-4 | CHI3L1 R4-54 |
|---|---|---|---|---|
| CHI3L1 293R3-2 | 0.2110*[a] | 0.6303*[c] | 0.7478*[c] | 0.7349*[c] |
| CHI3L1 293R3-4 | 0.1221*[b] | 0.3014*[a] | 1.1089*[c] | 0.4217*[c] |
| CHI3L1 R4-4 | 0.5680*[c] | 1.1305*[c] | 0.1232*[a] | 1.3845*[c] |
| CHI3L1 R4-54 | 0.1002*[b] | 0.1425*[b] | 1.1166*[c] | 0.2160*[a] |

While the disclosure has been described by way of example(s) and in terms of the preferred embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. An antibody or an antigen-binding portion thereof binding to chitinase-3 like-protein-1 (CHI3L1), comprising:

a heavy chain variable (VH) region comprising a heavy chain complementarity determining region (CDR-H1), a CDR H2, and a CDR H3 and a light chain variable (VL) region comprising a light chain complementarity determining region 1 (CDR L1), a CDR L2, and a CDR L3, wherein the CDR-H1 comprises SEQ ID NO: 3, the CDR-H2 comprises SEQ ID NO: 4, and the CDR-H3 comprises SEQ ID NO: 5; and the CDR-L1 comprises SEQ ID NO: 6, the CDR-L2 comprises SEQ ID NO: 7, and the CDR-L3 comprises SEQ ID NO: 8, wherein the CDR-H1 comprises SEQ ID NO: 11, the CDR-H2 comprises SEQ ID NO: 12, and the CDR-H3 comprises SEQ ID NO: 13; and the CDR-L1 comprises SEQ ID NO: 14, the CDR-L2 comprises SEQ ID NO: 15, and the CDR-L3 comprises SEQ ID NO: 16, wherein the CDR-H1 comprises SEQ ID NO: 19, the CDR-H2 comprises SEQ ID NO: 20, and the CDR-H3 comprises SEQ ID NO: 21; and the CDR-L1 comprises SEQ ID NO: 22, the CDR-L2 comprises SEQ ID NO: 23, and the CDR-L3 comprises SEQ ID NO: 24, wherein the CDR-H1 comprises SEQ ID NO: 27, the CDR-H2 comprises SEQ ID NO: 28, and the CDR-H3 comprises SEQ ID NO: 29; and the CDR-L1 comprises SEQ ID NO: 30, the CDR-L2 comprises SEQ ID NO: 31, and the CDR-L3 comprises SEQ ID NO: 32, wherein the CDR-H1 comprises SEQ ID NO: 35, the CDR-H2 comprises SEQ ID NO: 36, and the CDR-H3 comprises SEQ ID NO: 37; and the CDR-L1 comprises SEQ ID NO: 38, the CDR-L2 comprises SEQ ID NO: 39, and the CDR-L3 comprises SEQ ID NO: 40, wherein the CDR-H1 comprises SEQ ID NO: 43, the CDR-H2 comprises SEQ ID NO: 44, and the CDR-H3 comprises SEQ ID NO: 45; and the CDR-L1 comprises SEQ ID NO: 46, the CDR-L2 comprises SEQ ID NO: 47, and the CDR-L3 comprises SEQ ID NO: 48, wherein the CDR-H1 comprises SEQ ID NO: 51, the CDR-H2 comprises SEQ ID NO: 52, and the CDR-H3 comprises SEQ ID NO: 53; and the CDR-L1 comprises SEQ ID NO: 54, the CDR-L2 comprises SEQ ID NO: 55, and the CDR-L3 comprises SEQ ID NO: 56, wherein the CDR-H1 comprises SEQ ID NO: 59, the CDR-H2 comprises SEQ ID NO: 60, and the CDR-H3 comprises SEQ ID NO: 61; and the CDR-L1 comprises SEQ ID NO: 62, the CDR-L2 comprises SEQ ID NO: 63, and the CDR-L3 comprises SEQ ID NO: 64, wherein the CDR-H1 comprises SEQ ID NO: 67, the CDR-H2 comprises SEQ ID NO: 68, and the CDR-H3 comprises SEQ ID NO: 69; and the CDR-L1 comprises SEQ ID NO: 70, the CDR-L2 comprises SEQ ID NO: 71, and the CDR-L3 comprises SEQ ID NO: 72, wherein the CDR-H1 comprises SEQ ID NO: 75, the CDR-H2 comprises SEQ ID NO: 76, and the CDR-H3 comprises SEQ ID NO: 77; and the CDR-L1 comprises SEQ ID NO: 78, the CDR-L2 comprises SEQ ID NO: 79, and the CDR-L3 comprises SEQ ID NO: 80, or wherein the CDR-H1 comprises SEQ ID NO: 83, the CDR-H2 comprises SEQ ID NO: 84, and the CDR-H3 comprises SEQ ID NO: 85; and the CDR-L1 comprises SEQ ID NO: 86, the CDR-L2 comprises SEQ ID NO: 87, and the CDR-L3 comprises SEQ ID NO: 88.

2. The antibody or the antigen-binding portion thereof binding to CHI3L1 of claim 1, further comprising:

the VH region comprising SEQ ID NO: 1 or at least 90% amino acid sequence identity to SEQ ID NO: 1; and the VL region comprising SEQ ID NO: 2, or at least 90% amino acid sequence identity to SEQ ID NO: 2;

the VH region comprising SEQ ID NO: 9, or at least 90% amino acid sequence identity to SEQ ID NO: 9; and the VL region comprising SEQ ID NO: 10, or at least 90% amino acid sequence identity to SEQ ID NO: 10;

the VH region comprising SEQ ID NO: 17, or at least 90% amino acid sequence identity to SEQ ID NO: 17; and the VL region comprising SEQ ID NO: 18, or at least 90% amino acid sequence identity to SEQ ID NO: 18;

the VH region comprising SEQ ID NO: 25, or at least 90% amino acid sequence identity to SEQ ID NO: 25; and the VL region comprising SEQ ID NO: 26, or at least 90% amino acid sequence identity to SEQ ID NO: 26;

the VH region comprising SEQ ID NO: 33, or at least 90% amino acid sequence identity to SEQ ID NO: 33; and the VL region comprising SEQ ID NO: 34, or at least 90% amino acid sequence identity to SEQ ID NO: 34;

the VH region comprising SEQ ID NO: 41, or at least 90% amino acid sequence identity to SEQ ID NO: 41; and the VL region comprising SEQ ID NO: 42, or at least 90% amino acid sequence identity to SEQ ID NO: 42;

the VH region comprising SEQ ID NO: 49, or at least 90% amino acid sequence identity to SEQ ID NO: 49; and the VL region comprising SEQ ID NO: 50, or at least 90% amino acid sequence identity to SEQ ID NO: 50;

the VH region comprising SEQ ID NO: 57, or at least 90% amino acid sequence identity to SEQ ID NO: 57; and the VL region comprising SEQ ID NO: 58, or at least 90% amino acid sequence identity to SEQ ID NO: 58;

the VH region comprising SEQ ID NO: 65, or at least 90% amino acid sequence identity to SEQ ID NO: 65; and the VL region comprising SEQ ID NO: 66, or at least 90% amino acid sequence identity to SEQ ID NO: 66;

the VH region comprising SEQ ID NO: 73, or at least 90% amino acid sequence identity to SEQ ID NO: 73; and the VL region comprising SEQ ID NO: 74, or at least 90% amino acid sequence identity to SEQ ID NO: 74; or the VH region comprising SEQ ID NO: 81, or at least 90% amino acid sequence identity to SEQ ID NO: 81; and the VL region comprising SEQ ID NO: 82, or at least 90% amino acid sequence identity to SEQ ID NO: 82.

3. The antibody or the antigen-binding portion thereof binding to CHI3L1 of claim 1, wherein the antibody is a human antibody.

4. The antibody or the antigen-binding portion thereof binding to CHI3L1 of claim 1, wherein the antibody or the antigen-binding portion thereof is a single chain Fv (scFv), fragment-antigen binding (Fab), (Fab')2, or (scFv')2.

5. The antibody or the antigen-binding portion thereof binding to CHI3L1 of claim 1, wherein the antibody is an IgG, IgE, IgM, IgD, IgA, or IgY antibody.

6. The antibody or the antigen-binding portion thereof binding to CHI3L1 of claim 5, wherein the IgG antibody is an IgG1, IgG2, IgG3, or IgG4 antibody.

7. A pharmaceutical composition, comprising:

the antibody or the antigen-binding portion thereof of claim 1, and at least one pharmaceutically acceptable carrier.

8. The pharmaceutical composition of claim 7, further comprising a therapeutic agent.

9. The pharmaceutical composition of claim 8, wherein the therapeutic agent comprises gemcitabine.

10. An antibody-drug conjugate comprising:

a therapeutic agent; and the antibody or the antigen-binding portion thereof of claim 1, wherein the therapeutic agent is covalently conjugated to the antibody or the antigen-binding portion thereof by a linker.

11. A nucleic acid molecule encoding the antibody or the antigen-binding portion thereof of claim 1.

12. A method of treating cancer comprising administering to a patient in need thereof an effective amount of the antibody or the antigen-binding portion thereof of claim 1, wherein the cancer is a CHI3L1 expressing tumor.

13. The method of claim 12, wherein the cancer is pancreatic cancer, colon cancer, lung cancer, prostate cancer, melanoma, lymphoma, breast cancer, head and neck cancer, kidney cancer, urinary bladder cancer, uterine cancer, cervical cancer, ovarian cancer, liver cancer, stomach cancer, rectal cancer, thyroid cancer, skin cancer, brain cancer, bone cancer, or hematopoietic cancer.

14. The method of claim 12, wherein the antibody or the antigen-binding portion thereof is administered in combination with a therapeutic agent.

15. The method of claim 14, wherein the therapeutic agent comprises gemcitabine.

16. The method of claim 12, wherein a treatment of the antibody or the antigen-binding portion thereof reduces activated AKT signal, reduces activated extracellular signal-regulated kinase (ERK) signal, reduces cancer cells migration, reduces tumor progression, reduces tumor fibrosis, reduces angiogenesis, reduces cachexia, modulates tumor microenvironment (TME) toward an immunostimulatory phenotype, or a combination thereof.

17. The method of claim 13, wherein the lung cancer is non-small cell lung cancer (NSCLC).

18. The method of claim 13, wherein the head and neck cancer is esophageal cancer, oral cavity cancer, or pharynx cancer.

19. The method of claim 13, wherein the kidney cancer is renal cell carcinoma (RCC), or the hematopoietic cancer is leukemia.

* * * * *

SEQUENCE LISTING

```
Sequence total quantity: 88
SEQ ID NO: 1            moltype = AA  length = 127
FEATURE                 Location/Qualifiers
source                  1..127
                        mol_type = protein
                        organism = Homo sapiens
SEQUENCE: 1
QVQLVQSGAE VKKPGSSVKV SCKASGGTFS SYAISWVRQA PGQGLEWMGG IIPIFGTANY  60
AQKFQGRVTI TADESTSTAY MELSSLRSED TAVYYCARGD IEYYDILTGY YYYFDYWGQG  120
TLVTVSS                                                            127

SEQ ID NO: 2            moltype = AA  length = 214
FEATURE                 Location/Qualifiers
source                  1..214
                        mol_type = protein
                        organism = Homo sapiens
SEQUENCE: 2
SYVLTQPPSV SVAPGKAARV TCGGNDIGSK SVQWYQQKPG QAPVLVISYD NDRPSGIPER  60
FSGSNSGNTA TLTISRVEAG DEADYYCQVW DSTSDHYVFG TGTKVTVQGQ PKANPTVTLF  120
PPSSEELQAN KATLVCLISD FYPGAVTVAW KADSSPVKAG VETTTPSKQS NNKYAASSYL  180
SLTPEQWKSH RSYSCQVTHE GSTVEKTVAP TECS                              214

SEQ ID NO: 3            moltype = AA  length = 6
FEATURE                 Location/Qualifiers
source                  1..6
                        mol_type = protein
                        organism = Homo sapiens
SEQUENCE: 3
SSYAIS                                                             6
```

```
SEQ ID NO: 4            moltype = AA  length = 17
FEATURE                 Location/Qualifiers
source                  1..17
                        mol_type = protein
                        organism = Homo sapiens
SEQUENCE: 4
GIIPIFGTAN YAQKFQG                                              17

SEQ ID NO: 5            moltype = AA  length = 18
FEATURE                 Location/Qualifiers
source                  1..18
                        mol_type = protein
                        organism = Homo sapiens
SEQUENCE: 5
GDIEYYDILT GYYYYFDY                                             18

SEQ ID NO: 6            moltype = AA  length = 11
FEATURE                 Location/Qualifiers
source                  1..11
                        mol_type = protein
                        organism = Homo sapiens
SEQUENCE: 6
GGNDIGSKSV Q                                                    11

SEQ ID NO: 7            moltype = AA  length = 6
FEATURE                 Location/Qualifiers
source                  1..6
                        mol_type = protein
                        organism = Homo sapiens
SEQUENCE: 7
DNDRPS                                                          6

SEQ ID NO: 8            moltype = AA  length = 11
FEATURE                 Location/Qualifiers
source                  1..11
                        mol_type = protein
                        organism = Homo sapiens
SEQUENCE: 8
QVWDSTSDHY V                                                    11

SEQ ID NO: 9            moltype = AA  length = 118
FEATURE                 Location/Qualifiers
source                  1..118
                        mol_type = protein
                        organism = Homo sapiens
SEQUENCE: 9
EVQLLESGGG LLQPGGSLRL SCAASGLTFR NYAMTWVRQA PGKGLEWVST ISGNGDETFY  60
ADSVKGHFTI SRDNSKDTVY LQMNSLRAED TAVYYCAKGG HYSFFDSWGQ GSPVTVSS    118

SEQ ID NO: 10           moltype = AA  length = 216
FEATURE                 Location/Qualifiers
source                  1..216
                        mol_type = protein
                        organism = Homo sapiens
SEQUENCE: 10
NFMLTQPHSV SESPGKTVTI SCTRSSGSIA SNYVQWYQQR PGSSPTTVIY EDNQRPSGVP  60
DRFSGSIDSS SNSASLTISG LKTEDEADYY CQSYDSSNYV FGTGTKVTVL GQPKANPTVT  120
LFPPSSEELQ ANKATLVCLI SDFYPGAVTV AWKADGSPVK AGVETTKPSK QSNNKYAASS  180
YLSLTPEQWK SHRSYSCQVT HEGSTVEKTV APAECS                          216

SEQ ID NO: 11           moltype = AA  length = 5
FEATURE                 Location/Qualifiers
source                  1..5
                        mol_type = protein
                        organism = Homo sapiens
SEQUENCE: 11
NYAMT                                                           5

SEQ ID NO: 12           moltype = AA  length = 17
FEATURE                 Location/Qualifiers
source                  1..17
                        mol_type = protein
                        organism = Homo sapiens
SEQUENCE: 12
TISGNGDETF YADSVKG                                              17

SEQ ID NO: 13           moltype = AA  length = 9
FEATURE                 Location/Qualifiers
source                  1..9
```

```
                          mol_type = protein
                          organism = Homo sapiens
SEQUENCE: 13
GGHYSFFDS                                                             9

SEQ ID NO: 14             moltype = AA  length = 13
FEATURE                   Location/Qualifiers
source                    1..13
                          mol_type = protein
                          organism = Homo sapiens
SEQUENCE: 14
TRSSGSIASN YVQ                                                        13

SEQ ID NO: 15             moltype = AA  length = 7
FEATURE                   Location/Qualifiers
source                    1..7
                          mol_type = protein
                          organism = Homo sapiens
SEQUENCE: 15
EDNQRPS                                                               7

SEQ ID NO: 16             moltype = AA  length = 9
FEATURE                   Location/Qualifiers
source                    1..9
                          mol_type = protein
                          organism = Homo sapiens
SEQUENCE: 16
QSYDSSNYV                                                             9

SEQ ID NO: 17             moltype = AA  length = 127
FEATURE                   Location/Qualifiers
source                    1..127
                          mol_type = protein
                          organism = Homo sapiens
SEQUENCE: 17
EVQLVQSGAE VRKPGESLKI SCKASGYRFT NYWIGWVRQM PGKGLEWMGI IYPDDSNTKY  60
SPSFQGQVTI SVDKPITTAY LQWSSLKASD TAMYYCVRLD TYYYDSSGFP FDAFDIWGQG  120
TMVTVSS                                                             127

SEQ ID NO: 18             moltype = AA  length = 214
FEATURE                   Location/Qualifiers
source                    1..214
                          mol_type = protein
                          organism = Homo sapiens
SEQUENCE: 18
DIQMTQSPSS LSAFVGDRVT ITCQASQDIS TFLSWYQQKP GKAPKLLIYD ATNLETGVPS  60
RFSGRGSGTD FTFTISSLQP EDVATYFCQQ YDFLPLSFGG GTKVEIRRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LNSPVTKSFN RGEC                                214

SEQ ID NO: 19             moltype = AA  length = 5
FEATURE                   Location/Qualifiers
source                    1..5
                          mol_type = protein
                          organism = Homo sapiens
SEQUENCE: 19
NYWIG                                                                 5

SEQ ID NO: 20             moltype = AA  length = 17
FEATURE                   Location/Qualifiers
source                    1..17
                          mol_type = protein
                          organism = Homo sapiens
SEQUENCE: 20
IIYPDDSNTK YSPSFQG                                                    17

SEQ ID NO: 21             moltype = AA  length = 18
FEATURE                   Location/Qualifiers
source                    1..18
                          mol_type = protein
                          organism = Homo sapiens
SEQUENCE: 21
LDTYYYDSSG FPFDAFDI                                                   18

SEQ ID NO: 22             moltype = AA  length = 11
FEATURE                   Location/Qualifiers
source                    1..11
                          mol_type = protein
                          organism = Homo sapiens
```

```
SEQUENCE: 22
QASQDISTFL S                                                 11

SEQ ID NO: 23          moltype = AA  length = 7
FEATURE                Location/Qualifiers
source                 1..7
                       mol_type = protein
                       organism = Homo sapiens
SEQUENCE: 23
DATNLET                                                      7

SEQ ID NO: 24          moltype = AA  length = 9
FEATURE                Location/Qualifiers
source                 1..9
                       mol_type = protein
                       organism = Homo sapiens
SEQUENCE: 24
QQYDFLPLS                                                    9

SEQ ID NO: 25          moltype = AA  length = 117
FEATURE                Location/Qualifiers
source                 1..117
                       mol_type = protein
                       organism = Homo sapiens
SEQUENCE: 25
QVQLVQSGAE VKKPGASVKV SCKASGYTFT SYYMHWVRQA PGQGLEWMGI INPSGGSTSY  60
AQKFQGRVTM TRDTSTSTVY MELSSLRSED TAVYYCASDI GDYGDYWGQG TTVTVSS     117

SEQ ID NO: 26          moltype = AA  length = 214
FEATURE                Location/Qualifiers
source                 1..214
                       mol_type = protein
                       organism = Homo sapiens
SEQUENCE: 26
SYVLTQPPSV SVALGQTARI TCGGNNIESK IVSWYQQKPG QAPVLVIFYD TDRPSGISER  60
FSGSNSGNTA TLTISRVEAG DEADYYCQVW DSNSDHVIFG GGTKLTVLGQ PKAAPSVTLF  120
PPSSEELQAN KATLVCLISD FYPGAVTVAW KADSSPVKAG VETTTPSKQS NNKYAASSYL  180
SLTPEQWKSH RSYSCQVTHE GSTVEKTVAP TECS                              214

SEQ ID NO: 27          moltype = AA  length = 5
FEATURE                Location/Qualifiers
source                 1..5
                       mol_type = protein
                       organism = Homo sapiens
SEQUENCE: 27
SYYMH                                                        5

SEQ ID NO: 28          moltype = AA  length = 17
FEATURE                Location/Qualifiers
source                 1..17
                       mol_type = protein
                       organism = Homo sapiens
SEQUENCE: 28
IINPSGGSTS YAQKFQG                                           17

SEQ ID NO: 29          moltype = AA  length = 8
FEATURE                Location/Qualifiers
source                 1..8
                       mol_type = protein
                       organism = Homo sapiens
SEQUENCE: 29
DIGDYGDY                                                     8

SEQ ID NO: 30          moltype = AA  length = 11
FEATURE                Location/Qualifiers
source                 1..11
                       mol_type = protein
                       organism = Homo sapiens
SEQUENCE: 30
GGNNIESKIV S                                                 11

SEQ ID NO: 31          moltype = AA  length = 6
FEATURE                Location/Qualifiers
source                 1..6
                       mol_type = protein
                       organism = Homo sapiens
SEQUENCE: 31
DTDRPS                                                       6
```

-continued

```
SEQ ID NO: 32          moltype = AA  length = 11
FEATURE                Location/Qualifiers
source                 1..11
                       mol_type = protein
                       organism = Homo sapiens
SEQUENCE: 32
QVWDSNSDHV I                                                       11

SEQ ID NO: 33          moltype = AA  length = 120
FEATURE                Location/Qualifiers
source                 1..120
                       mol_type = protein
                       organism = Homo sapiens
SEQUENCE: 33
QVQLVESGGG VVQPGRSLRL SCAASGFTFS SYGMHWVRQA PGKGLEWVAV ISYDGSDKDY  60
ADSVKGRFTI SRDNSKNTLF LQMNSLRAED TAVYYCARDD YDSTYYFDNW GQGTTVTVSS  120

SEQ ID NO: 34          moltype = AA  length = 213
FEATURE                Location/Qualifiers
source                 1..213
                       mol_type = protein
                       organism = Homo sapiens
SEQUENCE: 34
SYELTQPPSV SVSPGQTASI TCSGDILADQ YASWYQQKPG QSPVLVIYHD TKRPSGVPER  60
FSGSTSGNTA TLTISGTQAM DEAAYYCQAW DINTAWVFGG GTQLTVLGQP KAAPSVTLFP  120
PSSEELQANK ATLVCLISDF YPGAVTVAWK ADSSPVKAGV ETTTPSKQSN NKYAASSYLS  180
LTPEQWKSHR SYSCQVTHEG STVEKTVAPT ECS                               213

SEQ ID NO: 35          moltype = AA  length = 5
FEATURE                Location/Qualifiers
source                 1..5
                       mol_type = protein
                       organism = Homo sapiens
SEQUENCE: 35
SYGMH                                                              5

SEQ ID NO: 36          moltype = AA  length = 17
FEATURE                Location/Qualifiers
source                 1..17
                       mol_type = protein
                       organism = Homo sapiens
SEQUENCE: 36
VISYDGSDKD YADSVKG                                                 17

SEQ ID NO: 37          moltype = AA  length = 11
FEATURE                Location/Qualifiers
source                 1..11
                       mol_type = protein
                       organism = Homo sapiens
SEQUENCE: 37
DDYDSTYYFD N                                                       11

SEQ ID NO: 38          moltype = AA  length = 11
FEATURE                Location/Qualifiers
source                 1..11
                       mol_type = protein
                       organism = Homo sapiens
SEQUENCE: 38
SGDILADQYA S                                                       11

SEQ ID NO: 39          moltype = AA  length = 7
FEATURE                Location/Qualifiers
source                 1..7
                       mol_type = protein
                       organism = Homo sapiens
SEQUENCE: 39
HDTKRPS                                                            7

SEQ ID NO: 40          moltype = AA  length = 10
FEATURE                Location/Qualifiers
source                 1..10
                       mol_type = protein
                       organism = Homo sapiens
SEQUENCE: 40
QAWDINTAWV                                                         10

SEQ ID NO: 41          moltype = AA  length = 118
FEATURE                Location/Qualifiers
source                 1..118
```

```
                         mol_type = protein
                         organism = Homo sapiens
SEQUENCE: 41
EVQLVESGGG LVQPGGSLRL SCAASGLTFP NFAMTWVRQT PGKGLQWVST ISGRGDEPFY  60
ADSVKGRFTI SRDNSKNMVY LHMNSLRAED TAIYYCAKGG HFSSWDYWGQ GTLVTVSS    118

SEQ ID NO: 42            moltype = AA  length = 216
FEATURE                  Location/Qualifiers
source                   1..216
                         mol_type = protein
                         organism = Homo sapiens
SEQUENCE: 42
NFMLTQPHSV SESPGKTVTI SCTRSSGSIA SNYVQWYQQR PDSAPTTVIY EDIERPSGVP  60
DRFSGAIDSS ANSASLTISG LQTEDEADYY CQSYDSSSYV FGTGTKVTVL GQPKANPTVT  120
LFPPSSEELQ ANKATLVCLI SDFYPGAVTV AWKADGSPVK AGVETTKPSK QSNNKYAASS  180
YLSLTPEQWK SHRSYSCQVT HEGSTVEKTV APTECS                            216

SEQ ID NO: 43            moltype = AA  length = 5
FEATURE                  Location/Qualifiers
source                   1..5
                         mol_type = protein
                         organism = Homo sapiens
SEQUENCE: 43
NFAMT                                                              5

SEQ ID NO: 44            moltype = AA  length = 17
FEATURE                  Location/Qualifiers
source                   1..17
                         mol_type = protein
                         organism = Homo sapiens
SEQUENCE: 44
TISGRGDEPF YADSVKG                                                 17

SEQ ID NO: 45            moltype = AA  length = 9
FEATURE                  Location/Qualifiers
source                   1..9
                         mol_type = protein
                         organism = Homo sapiens
SEQUENCE: 45
GGHFSSWDY                                                          9

SEQ ID NO: 46            moltype = AA  length = 13
FEATURE                  Location/Qualifiers
source                   1..13
                         mol_type = protein
                         organism = Homo sapiens
SEQUENCE: 46
TRSSGSIASN YVQ                                                     13

SEQ ID NO: 47            moltype = AA  length = 7
FEATURE                  Location/Qualifiers
source                   1..7
                         mol_type = protein
                         organism = Homo sapiens
SEQUENCE: 47
EDIERPS                                                            7

SEQ ID NO: 48            moltype = AA  length = 9
FEATURE                  Location/Qualifiers
source                   1..9
                         mol_type = protein
                         organism = Homo sapiens
SEQUENCE: 48
QSYDSSSYV                                                          9

SEQ ID NO: 49            moltype = AA  length = 116
FEATURE                  Location/Qualifiers
source                   1..116
                         mol_type = protein
                         organism = Homo sapiens
SEQUENCE: 49
EVQLVQSGAE VKKPGATVKI SCKVSGYTFT DYYMHWVQQA PGKGLEWMGL VDPEDGETIY  60
AEKFQGRVTI TADTSTDTAY MELSSLRSED TAVYYCATIG RPPDYWGQGT TVTVSS      116

SEQ ID NO: 50            moltype = AA  length = 216
FEATURE                  Location/Qualifiers
source                   1..216
                         mol_type = protein
                         organism = Homo sapiens
```

```
SEQUENCE: 50
QSVLTQPPSV SAAPGQKVTI SCSGSSSNIG NNYVSWYQQL PGTAPKLLIY DNNKRPSGIP  60
DRFSGSKSGT SATLGITGLQ TGDEADYYCG TWDSSLSVWV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHKSYSCQVT HEGSTVEKTV APTECS                           216

SEQ ID NO: 51          moltype = AA  length = 5
FEATURE                Location/Qualifiers
source                 1..5
                       mol_type = protein
                       organism = Homo sapiens
SEQUENCE: 51
DYYMH                                                             5

SEQ ID NO: 52          moltype = AA  length = 17
FEATURE                Location/Qualifiers
source                 1..17
                       mol_type = protein
                       organism = Homo sapiens
SEQUENCE: 52
LVDPEDGETI YAEKFQG                                                17

SEQ ID NO: 53          moltype = AA  length = 7
FEATURE                Location/Qualifiers
source                 1..7
                       mol_type = protein
                       organism = Homo sapiens
SEQUENCE: 53
IGRPPDY                                                           7

SEQ ID NO: 54          moltype = AA  length = 13
FEATURE                Location/Qualifiers
source                 1..13
                       mol_type = protein
                       organism = Homo sapiens
SEQUENCE: 54
SGSSSNIGNN YVS                                                    13

SEQ ID NO: 55          moltype = AA  length = 7
FEATURE                Location/Qualifiers
source                 1..7
                       mol_type = protein
                       organism = Homo sapiens
SEQUENCE: 55
DNNKRPS                                                           7

SEQ ID NO: 56          moltype = AA  length = 11
FEATURE                Location/Qualifiers
source                 1..11
                       mol_type = protein
                       organism = Homo sapiens
SEQUENCE: 56
GTWDSSLSVW V                                                      11

SEQ ID NO: 57          moltype = AA  length = 123
FEATURE                Location/Qualifiers
source                 1..123
                       mol_type = protein
                       organism = Homo sapiens
SEQUENCE: 57
QVQLVESGGG VVQPGRSLRL SCAASGFTFS SYAMHWVRQA PGKGLEWVAV ISYDGSNKYY  60
ADSVKGRFTI SRDNSKNTLY LQMNSLRAED TAVYYCARDT ELQLWSGGYF DYWGQGTLVT  120
VSS                                                               123

SEQ ID NO: 58          moltype = AA  length = 216
FEATURE                Location/Qualifiers
source                 1..216
                       mol_type = protein
                       organism = Homo sapiens
SEQUENCE: 58
NFMLTQPHSV SESPGKTVII SCTRSSGSIA HNYVQWYQLR PGSAPTTVIS DDDQRPSGVP  60
DRFSGSIDSS SNSASLTISG LRTEDEADYY CQSFDDSNWV FGGGTRLTVL GQPKAAPSVT  120
LFPPSSEELQ ANKATLVCLI SDFYPGAVTV AWKADSSPVK AGVETTTPSK QSNNKYAASS  180
YLSLTPEQWK SHKSYSCQVT HEGSTVEKTV APTECS                           216

SEQ ID NO: 59          moltype = AA  length = 5
FEATURE                Location/Qualifiers
source                 1..5
                       mol_type = protein
```

```
                        organism = Homo sapiens
SEQUENCE: 59
SYAMH                                                                   5

SEQ ID NO: 60           moltype = AA  length = 17
FEATURE                 Location/Qualifiers
source                  1..17
                        mol_type = protein
                        organism = Homo sapiens
SEQUENCE: 60
VISYDGSNKY YADSVKG                                                      17

SEQ ID NO: 61           moltype = AA  length = 14
FEATURE                 Location/Qualifiers
source                  1..14
                        mol_type = protein
                        organism = Homo sapiens
SEQUENCE: 61
DTELQLWSGG YFDY                                                         14

SEQ ID NO: 62           moltype = AA  length = 13
FEATURE                 Location/Qualifiers
source                  1..13
                        mol_type = protein
                        organism = Homo sapiens
SEQUENCE: 62
TRSSGSIAHN YVQ                                                          13

SEQ ID NO: 63           moltype = AA  length = 7
FEATURE                 Location/Qualifiers
source                  1..7
                        mol_type = protein
                        organism = Homo sapiens
SEQUENCE: 63
DDDQRPS                                                                 7

SEQ ID NO: 64           moltype = AA  length = 9
FEATURE                 Location/Qualifiers
source                  1..9
                        mol_type = protein
                        organism = Homo sapiens
SEQUENCE: 64
QSFDDSNWV                                                               9

SEQ ID NO: 65           moltype = AA  length = 120
FEATURE                 Location/Qualifiers
source                  1..120
                        mol_type = protein
                        organism = Homo sapiens
SEQUENCE: 65
QVQLQESGPG LVEPSGTLSL TCAVSGGSIS SSNWWSWVRQ HPGKGLEWIG EIYHSGSTNY  60
NPSLRSRVTI SVDKSKNQFS LELSSVTAAD TAVYYCAGDQ RMEDDAFDIW GQGTMVTVSS  120

SEQ ID NO: 66           moltype = AA  length = 217
FEATURE                 Location/Qualifiers
source                  1..217
                        mol_type = protein
                        organism = Homo sapiens
SEQUENCE: 66
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTLY VFGTGTKVTV LGQPKANPTV  120
TLFPPSSEEL QANKATLVCL ISDFYPGAVT VAWKADGSPV KAGVETTKPS KQSNNKYAAS  180
SYLSLTPEQW KSHRSYSCQV THEGSTVEKT VAPTECS                            217

SEQ ID NO: 67           moltype = AA  length = 6
FEATURE                 Location/Qualifiers
source                  1..6
                        mol_type = protein
                        organism = Homo sapiens
SEQUENCE: 67
SSNWWS                                                                  6

SEQ ID NO: 68           moltype = AA  length = 16
FEATURE                 Location/Qualifiers
source                  1..16
                        mol_type = protein
                        organism = Homo sapiens
SEQUENCE: 68
EIYHSGSTNY NPSLRS                                                       16
```

```
SEQ ID NO: 69           moltype = AA  length = 11
FEATURE                 Location/Qualifiers
source                  1..11
                        mol_type = protein
                        organism = Homo sapiens
SEQUENCE: 69
DQRMEDDAFD I                                                          11

SEQ ID NO: 70           moltype = AA  length = 14
FEATURE                 Location/Qualifiers
source                  1..14
                        mol_type = protein
                        organism = Homo sapiens
SEQUENCE: 70
TGTSSDVGGY NYVS                                                       14

SEQ ID NO: 71           moltype = AA  length = 7
FEATURE                 Location/Qualifiers
source                  1..7
                        mol_type = protein
                        organism = Homo sapiens
SEQUENCE: 71
DVSNRPS                                                               7

SEQ ID NO: 72           moltype = AA  length = 11
FEATURE                 Location/Qualifiers
source                  1..11
                        mol_type = protein
                        organism = Homo sapiens
SEQUENCE: 72
SSYTSSSTLY V                                                          11

SEQ ID NO: 73           moltype = AA  length = 123
FEATURE                 Location/Qualifiers
source                  1..123
                        mol_type = protein
                        organism = Homo sapiens
SEQUENCE: 73
EVQLVQSGAE VKKPGATVKI SCKVSGYSFT DYYIHWVQQA PGKGLEWMGF VDPENGETIY  60
AEKFQGRVTI TADTSTDTAY MELSSLRSDD TAVYYCATDR DYDDSSGNAF DIWGQGTMVT  120
VSS                                                                123

SEQ ID NO: 74           moltype = AA  length = 214
FEATURE                 Location/Qualifiers
source                  1..214
                        mol_type = protein
                        organism = Homo sapiens
SEQUENCE: 74
SYELTQPPSV SVSTGQTATI TCSGDILGDE YAFWYQQKAG QSPVLVIYLD TRRPSGIPER  60
FSGSNSGDTA TLTISETQPV DEAVYFCQGW DSSTALYVFG TGTKVTVLGQ PKANPTVTLF  120
PPSSEELQAN KATLVCLISD FYPGAVTVAW KADGSPVKAG VETTKPSKQS NNKYAASSYL  180
SLTPEQWKSH RSYSCQVTHE GSTVEKTVAP TECS                              214

SEQ ID NO: 75           moltype = AA  length = 5
FEATURE                 Location/Qualifiers
source                  1..5
                        mol_type = protein
                        organism = Homo sapiens
SEQUENCE: 75
DYYIH                                                                 5

SEQ ID NO: 76           moltype = AA  length = 17
FEATURE                 Location/Qualifiers
source                  1..17
                        mol_type = protein
                        organism = Homo sapiens
SEQUENCE: 76
FVDPENGETI YAEKFQG                                                    17

SEQ ID NO: 77           moltype = AA  length = 14
FEATURE                 Location/Qualifiers
source                  1..14
                        mol_type = protein
                        organism = Homo sapiens
SEQUENCE: 77
DRDYDDSSGN AFDI                                                       14

SEQ ID NO: 78           moltype = AA  length = 11
```

```
FEATURE                Location/Qualifiers
source                 1..11
                       mol_type = protein
                       organism = Homo sapiens
SEQUENCE: 78
SGDILGDEYA F                                                       11

SEQ ID NO: 79          moltype = AA  length = 7
FEATURE                Location/Qualifiers
source                 1..7
                       mol_type = protein
                       organism = Homo sapiens
SEQUENCE: 79
LDTRRPS                                                            7

SEQ ID NO: 80          moltype = AA  length = 11
FEATURE                Location/Qualifiers
source                 1..11
                       mol_type = protein
                       organism = Homo sapiens
SEQUENCE: 80
QGWDSSTALY V                                                       11

SEQ ID NO: 81          moltype = AA  length = 122
FEATURE                Location/Qualifiers
source                 1..122
                       mol_type = protein
                       organism = Homo sapiens
SEQUENCE: 81
EVQLVQSGAG VKKPGATVKI SCKVSGYTFT DYYMHWVQQA PGKGLEWMGL VDPEDGETIY  60
AEKFQGRVTI TADTSTDTAY MELSSLRSED TAVYYCATAS PREEMPYYFD YWGQGTLVTV  120
SS                                                                 122

SEQ ID NO: 82          moltype = AA  length = 213
FEATURE                Location/Qualifiers
source                 1..213
                       mol_type = protein
                       organism = Homo sapiens
SEQUENCE: 82
SYELTQPPSV SVSPGQTASI TCSGDILADQ YASWYQQKPG QSPVLVIYHD TKRPSGVPER  60
FSGSTSGNTA TLTISGTQAM DEAAYYCQAW DINTAWVFGG GTQLTVLGQP KAAPSVTLFP  120
PSSEELQANK ATLVCLISDF YPGAVTVAWK ADSSPVKAGV ETTTPSKQSN NKYAASSYLS  180
LTPEQWKSHR SYSCQVTHEG STVEKTVAPT ECS                               213

SEQ ID NO: 83          moltype = AA  length = 5
FEATURE                Location/Qualifiers
source                 1..5
                       mol_type = protein
                       organism = Homo sapiens
SEQUENCE: 83
DYYMH                                                              5

SEQ ID NO: 84          moltype = AA  length = 17
FEATURE                Location/Qualifiers
source                 1..17
                       mol_type = protein
                       organism = Homo sapiens
SEQUENCE: 84
LVDPEDGETI YAEKFQG                                                 17

SEQ ID NO: 85          moltype = AA  length = 13
FEATURE                Location/Qualifiers
source                 1..13
                       mol_type = protein
                       organism = Homo sapiens
SEQUENCE: 85
ASPREEMPYY FDY                                                     13

SEQ ID NO: 86          moltype = AA  length = 11
FEATURE                Location/Qualifiers
source                 1..11
                       mol_type = protein
                       organism = Homo sapiens
SEQUENCE: 86
SGDILADQYA S                                                       11

SEQ ID NO: 87          moltype = AA  length = 7
FEATURE                Location/Qualifiers
source                 1..7
```

-continued

```
                    mol_type = protein
                    organism = Homo sapiens
SEQUENCE: 87
HDTKRPS                                                             7

SEQ ID NO: 88       moltype = AA  length = 10
FEATURE             Location/Qualifiers
source              1..10
                    mol_type = protein
                    organism = Homo sapiens
SEQUENCE: 88
QAWDINTAWV                                                          10
```